United States Patent [19]

Matsumoto et al.

[11] Patent Number: 5,420,126
[45] Date of Patent: May 30, 1995

[54] 3,4-DIHYDRO-2H-1,4-BENZOXAZINE DERIVATIVES AND PHARMACEUTICAL COMPOSITIONS CONTAINING THE SAME

[75] Inventors: Yuzo Matsumoto; Ryuji Tsuzuki; Akira Matsuhisa; Kazuhisa Takayama; Wataru Uchida, all of Ibaraki; Masaharu Asano; Isao Yanagisawa, both of Tokyo; Toru Yoden, Ibaraki, all of Japan

[73] Assignee: Yamanouchi Pharmaceutical Co., Ltd., Tokyo, Japan

[21] Appl. No.: 982,034

[22] Filed: Nov. 24, 1992

Related U.S. Application Data

[63] Continuation of Ser. No. 823,256, Jan. 21, 1992, abandoned, which is a continuation-in-part of Ser. No. 607,291, Oct. 30, 1990, abandoned.

[30] Foreign Application Priority Data

| Nov. 8, 1989 | [JP] | Japan | 1-290727 |
| Dec. 5, 1989 | [JP] | Japan | 1-315926 |
| Dec. 28, 1989 | [JP] | Japan | 1-342937 |
| Aug. 6, 1990 | [JP] | Japan | 2-208548 |

[51] Int. Cl.$^6$ ............... C07D 273/01; C07D 413/02
[52] U.S. Cl. ................... 514/230.5; 544/105
[58] Field of Search ................. 544/105; 514/230.5

[56] References Cited

U.S. PATENT DOCUMENTS

| 3,879,522 | 4/1975 | Pesson | 514/230.5 |
| 4,721,784 | 1/1988 | Combs | 544/105 |
| 4,798,620 | 1/1989 | Kume et al. | 544/105 |
| 4,826,985 | 5/1989 | Mitscher et al. | 544/105 |
| 4,962,200 | 10/1990 | Kihara et al. | 544/105 |
| 5,055,110 | 10/1991 | Lim et al. | 544/105 |

FOREIGN PATENT DOCUMENTS 196570 10/1986 European Pat. Off. .
1137796 12/1968 United Kingdom .

OTHER PUBLICATIONS

E. I. Du Pont de Nemours & Co, Chem. Abstract vol. 85:144672y, (1976).
Ge et al, Chem. Abstract vol. 110:192749k (1988), and Stn Printout.
Bigg et al., Chem. Abstract vol. 105: 133897f (1986).
Teulon, Chem. Abstract vol. 104: 109668r (1984).

Primary Examiner—Mukund J. Shah
Assistant Examiner—Philip I. Datlow
Attorney, Agent, or Firm—Burgess, Ryan & Wayne

[57] ABSTRACT

Novel benzoxazine derivatives of the formula (I):

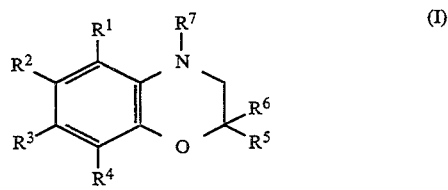

are provided as well as their pharmaceutically acceptable salts and a method for their use as potassium channel activating agents 2-(3,4-Dihydro-2, 2-dimethyl-6-phenylsulfonyl-2H-1,4-benzoxazin-4-yl)pyridine N-oxide is illustrative of a benzoxazine derivative of formula (I). Also provided are intermediate compounds such as those of formula (II):

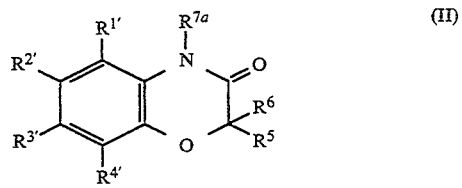

9 Claims, No Drawings

3,4-DIHYDRO-2H-1,4-BENZOXAZINE DERIVATIVES AND PHARMACEUTICAL COMPOSITIONS CONTAINING THE SAME

CROSS-REFERENCE TO RELATED APPLICATIONS

This application is a continuation of application Ser. No. 823,256, filed Jan. 21, 1992, now abandoned which application is a continuation-in-part of application Ser. No. 607,291, filed Oct. 30, 1990, now abandoned.

BACKGROUND OF THE INVENTION

1. Field of the Invention

This invention relates to novel benzoxazine derivatives and pharmaceutically acceptable salts thereof, which are useful as drugs, in particular as potassium channel ($K^+$ channel) activating agents, and pharmaceutical compositions containing the same as well as to intermediates for the production of these derivatives and salts.

The benzoxazine derivatives and salts thereof according to the present invention are compounds of a novel type which activate $K^+$ channels and thereby exhibit antispasmodic activity, namely smooth muscle relaxant activity.

2. Background of the Related Art

As smooth muscle relaxants, those acting on the contractile process and those acting on the relaxing process are known. Among drugs in the former category are various excitatory chemical transmitter receptor blockers and calcium antagonists, while inhibitory chemical transmitter receptor stimulants and nitrates are representative of the latter type of drugs.

Recently, a drug which relaxes smooth muscles by activating the $K^+$ channels has been reported as a new smooth muscle relaxant.

In the thick arteries (particularly the coronary and cerebral arteries) and tracheal smooth muscles in contrast with the general excitable tissues, the $K^+$ channels function in such a manner that these tissues will not be excited to an unnecessary extent by premature and excessive activation (maintenance of lumen size) but if the physiological function of the $K^+$ channels is impaired, an electric excitation takes place as intensely as in the general excitable tissues to elicit intense local contractions, viz. spasms. It is acknowledged that spasms of the coronary or cerebral arteries and tracheal smooth muscles induce various diseases such as angina pectoris, cerebrovascular disorder and asthma. It is, therefore, believed that a $K^+$ channel activating agent should be useful for the prevention and treatment of these diseases.

Among the compounds known to have $K^+$ channel activating activity, there are 4-(2-oxo-1-pyrrolidinyl)-2H-benzo[b]pyran-3-ol derivatives as disclosed in EP 76075, for instance. The compounds according to the present invention are novel 2H-1,4-benzoxazine derivatives differing in structure from such known compounds.

SUMMARY OF THE INVENTION

As a result of intensive investigations made in an attempt to find out potent $K^+$ channel activating compounds, the present inventors found that novel benzoxazine derivatives of general formula (I) given below and salts thereof are potent $K^+$ channel activators and that compounds of General Formula (II) or (III) shown below are useful as intermediates for the production of said benzoxazine compounds and salts thereof. The present invention has been completed on the basis of such findings.

The present invention thus provides benzoxazine derivatives of the General Formula (I):

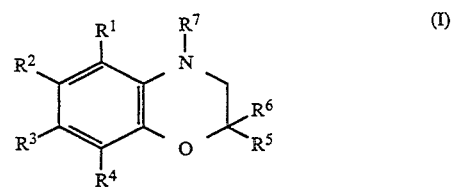

and pharmaceutically acceptable salts thereof, wherein, in the above formula, $R^1$, $R^2$, $R^3$ and $R^4$ which may be the same or different, each independently represents a hydrogen or halogen atom or a lower alkyl, halo-substituted lower alkyl, lower alkoxy, cyano, nitro, amino, lower alkanoylamino, loweralkylsulfonylamino, lower alkylsulfonyl, or arylsulfonyl group;

$R^5$ and $R^6$, which may be the same or different, each independently represents a hydrogen atom or a lower alkyl group;

$R^7$ represents a hydroxy-lower alkyl group, a carbocylic group substituted by at least one substituent selected from the group consisting of a lower alkyl group, a hydroxy group, an oxo group, a lower alkoxycarbonyl group, a hydroxyimino group, and a lower alkoxyimino group, a heterocyclic group which may optionally be substituted, a group of the formula -$A^1$-$R^8$ (in which $A^1$ represents a lower alkylene or hydroxy-lower alkylene group and $R^8$ represents an aryl group which may optionally be substituted, a heterocyclic group which may optionally be substituted, or a lower alkenyloxy group, when $A^1$ represents a non-substituted lower alkylene, $R^8$ does not represent a phenyl group), a group of the formula

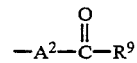

(in which $A^2$ represents a lower alkylene group and $R^9$ represents a lower alkyl group, an aryl group which may optionally be substituted, a heterocyclic group which may optionally be substituted, or a hydroxy, lower alkoxy, amino, mono- or di-lower alkylamino, hydroxy-lower alkyamino, aralkylamino or arylamino group), a group of the formula

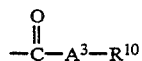

(in which $A^3$ represents a single bond, a lower alkylene group which may optionally be substituted by an amino group or a mono- or di-lower alkylamino group, or a lower alkenylene group and $R^{10}$ represents a heterocyclic group which may optionally be substituted, or a carboxyl, lower alkoxycarbonyl, carbamoyl, mono- or di-lower alkylaminocarbonyl), or a group of the formula

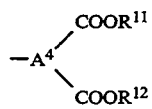

(in which $A^4$ represents a lower alkylene group which may optionally be substituted by a hydroxy or lower alkoxy group, and $R^{11}$ and $R^{12}$, which may be the same or different, each independently represents a hydrogen atom or a lower alkyl group).

In the benzoxazine derivatives of the above formula (I), when $R^7$ is a group of the formula $-A^1-R^8$ and $A^1$ is an unsubstituted lower alkylene group, then $R^8$ is not a phenyl group. Additionally, when $R^7$ is a group of the formula $-A^1-R^8$ and $A^1$ is an unsubstituted lower alkylene group and $R^8$ is a heterocyclic group, then $R^5$ and $R^6$ are not both hydrogen atoms.

The compounds (I) according to the present invention are characterized, from the chemical structure viewpoint, in that a specific heterocycle, namely, the 3,4-dihydro-2H-1,4-benzoxazine ring, is substituted at a specific position, namely the 4-position of the ring, by a specific substituent represented by $R^7$.

Known in the art as similar 3,4-dihydro-2H-1,4-benzoxazine derivatives are 4-acyl-3,4-dihydro-2H-1,4-benzoxazine derivatives [C. B. Chapleo et al., J. Med. Chem., 32 (7), 1627-30 (1989)] and 4-benzyl-3,4-dihydro-2H-1,4-benzoxazine derivatives [JP1034982 (CA111(11):97257k), C. B. Chapleo et al., J. Med. Chem., 32(7), 1627-30 (1989)], for instance. However, it has never been reported that such known compounds have $K^+$ channel activating activity.

The valuable intermediates provided by the present invention are compounds of-the general formula (II) or (III) given below.

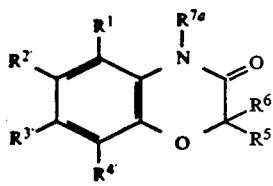

In formula (II), $R^5$ and $R^6$ are as defined above and $R^{1'}$, $R^{2'}$, $R^{3'}$ and $R^{4'}$, which may be the same or different, each indpendently represents a hydrogen atom, a halogen atom, a cyano group, or a nitro group; $R^{7a}$ represents a carbocyclic group substituted by an oxo group, or a group of the formula

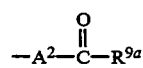

(in which $A^2$ is as defined above and $R^{9a}$ represents a lower alkyl group, an unsubstituted or halo- or nitro-substituted aryl group or a nitrogen-containing heterocyclic group which may optionally be substituted by at least one of an oxo group and a lower alkyl group, inclusive of the N-oxide form thereof, an amino, a mono- or di-lower alkylamino, hydroxy-lowe alkylamino, aralkylamino or arylamino group). In formual (II)-above, when $R^{7a}$ is a group of the formula

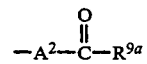

and $R^{9a}$ is an amino group or a mono-or di-lower alkylamino group, then $R^5$ and $R^6$ are lower alkyl groups.

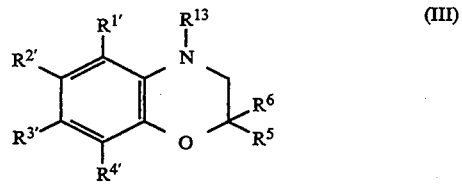

In formula (III), $R^{1'}$, $R^{2'}$, $R^{3'}$, $R^{4'}$, $R^5$ and $R^6$ are as defined above and $R^{13}$ represents a nitroso or amino group.

The intermediates (II) according to the present invention are novel compounds that have not been described in the literature and are useful in the manufacture of those compounds of the general formula (I), including salts thereof, which have the group $R^{7a}$ as the group $R^7$. The intermediates (III) are useful in the production of those compounds of general formula (I) in which a nitrogen-containing heterocyclic group (as $R^7$) is bound, via the nitrogen atom thereof, to the 4-position nitrogen atom of the benzoxazine ring. In formula (III), when $R^{13}$ is an amino group, then $R^5$ and $R^6$ are not both hydrogen atoms.

It is an object of the present invention to provide the above-mentioned compounds (I) and pharmaceutically acceptable salts thereof, which are useful as $K^+$ channel activating agents.

Another object of the present invention is to provide pharmaceutical compositions comprising any of the above-mentioned compounds (I) and pharmaceutically acceptable salts thereof in admixture with a pharmaceutically acceptable carrier therefor.

A further object of the present invention is to provide the compounds (II) and compounds (III), inclusive of salts thereof, which are useful as intermediates for the production of the above-mentioned compounds (I) and salts thereof.

DETAILED DESCRIPTION OF THE INVENTION

The compounds of the present invention are described in more detail.

In the definitions given herein in relation to the general formulas shown hereinbefore and hereinlater, the term "lower" means, unless otherwise specified, that the relevant group includes a straight or branched carbon chain containing 1 to 6 carbon atoms.

Accordingly, the "lower alkyl group" includes, among others, methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The "lower alkoxy group" includes, among others, methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy and hexyloxy.

The "lower alkenyloxy group" contains 2 to 6 carbon atoms and may be straight or branched, more specifically including, among others, vinyloxy, allyloxy, 1-propenyloxy, isopropenyloxy, 1-butenyloxy, 2-butenyloxy, 3-butenyloxy, 2-methyl-1-propenyloxy, 2-methylallyloxy, 1-methyl-1-propenyloxy, 1-methylallyloxy, 1,1-dimethylvinyloxy, 1-pentenyloxy, 2-pentenyloxy, 3-pentenyloxy, 4-pentenyloxy, 3-methyl-1-butenyloxy, 1-hexenyloxy, 2-hexenyloxy, 3-hexenyloxy, 4-hexenyloxy and 5-hexenyloxy.

The "lower alkoxycarbonyl group", which is a group resulting from ester formation between a carobxy group and a straight or branched lower alcohol, includes, among others, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl and hexyloxycarbonyl.

The "lower alkanoyl-group" includes, among others, formyl, acetyl, propionyl, butyryl, isobutyryl, valeryl, isovaleryl, pivaloyl and hexanoyl.

The "mono- or di-lower alkylamino group" means a group derived from an amino group by substitution of one or two hydrogen atoms thereof by the above-mentioned "lower alkyl" group or groups and, more specifically, includes monoalkylamino groups in which the alkyl moiety is a straight or branched lower alkyl group, for example methylamino, ethylamino, propylamino, isopropylamino, butylamino, isobutylamino, pentylamino, isopentylamino and hexylamino; symmetric dialkylamino groups in which the two alkyl moieties are the same and each is a straight or branched lower alkyl group, for example dimethylamino, diethylamino, dipropylamino, diisopropylamino, dibutylamino, dipentylamino and dihexylamino; and asymmetric dialkylamino groups in which the alkyl moieties are different from each other and each is a straight or branched lower alkyl group, for example ethylmethylamino, methylpropylamino, ethylpropylamino, butylmethylamino, butylethylamino and butylpropylamino.

The "mono- or di-lower alkylaminocarbonyl group" is a group resulting from binding of a carbonyl group to the above-mentioned "mono- or di-lower alkylamino group" and more specifically, includes, among others, methylaminocarbonyl, ethylaminocarbonyl, propylaminocarbonyl, isopropylaminocarbonyl, butylaminocarbonyl, isobutylaminocarbonyl, sec-butylaminocarbonyl, tert-butylaminocarbonyl, pentylaminocarbonyl, isopentylaminocarbonyl, hexylaminocarbonyl, isohexylaminocarbonyl, dimethylaminocarbonyl, diethylaminocarbonyl, dipropylaminocarbonyl, diisopropylaminocarbonyl, dibutylaminocarbonyl, dipentylaminocarbonyl, dihexylaminocarbonyl, methylethylaminocarbonyl, methylpropylaminocarbonyl, ethylpropylaminocarbonyl, methylbutylaminocarbonyl, ethylbutylaminocarbonyl and propylbutylaminocarbonyl.

The "lower alkanoylamino group" may be straight or branched and includes, among others, formylamino, acetylamino, propionylamino, butyrylamino, isobutyryl amino, valerylamino, isovalerylamino, pivaloylamino and hexanoylamino.

The "lower alkylsulfonyl group" includes, among others, methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, sec-pentylsulfonyl, neopentylsulfonyl, tert-pentylsulfonyl, hexylsulfonyl and isohexylsulfonyl.

The "lower alkylsulfonylamino group" is a group derived from an amino group by substitution of one hydrogen atom thereof by the "lower alkylsulfonyl group" mentioned above and, more specifically, includes such straight or branched lower alkylsulfonylamino groups as methylsulfonylamino, ethylsulfonylamino, propylsulfonylamino, isopropylsulfonylamino, butylsulfonylamino, isobutylsulfonylamino, sec-butylsulfonylamino, tert-butylsulfonylamino, pentylsulfonylamino and hexylsulfonylamino.

The "lower alkylene group", which preferably contains 1 to 6 carbon atoms, includes, among others, methylene, ethylene, methylmethylene, trimethylene, 2-methylethylene, 1-methylethylene, dimethylmethylene, tetramethylene, 1-methyltrimethylene, 2-methyltrimethylene, 3-methyltrimethylene, 1-ethylethylene, 2-ethylethylene, 2,2-dimethylethylene, 1,1-dimethylethylene, ethylmethylmethylene, pentamethylene, 1-methyltetramethylene, 2-methyltetramethylene, 3-methyltetramethylene, 4-methyltetramethylene, 1,1-dimethyltrimethylene, hexamethylene, 1-methyipentamethylene, 4-methylpentamethylene and 1,1-dimethyltetramethylene.

The "lower alkenylene group", which preferably contains 2 to 6 carbon atoms, includes, among others, vinylene, propenylene, 2-propenylene, 1-methylvinylene, 2-methylvinylene, butenylene, 2-butenylene, 3-butenylene, 1-methylpropenylene, 1-methyl-2-propenylene, pentenylene and 1-methyl-1-butenylene.

The "halogen atom" is not limited to any particular species but includes fluorine, chlorine, bromine and iodine.

The "halo-substituted lower alkyl group" is a group derived from the above-mentioned "lower alkyl group" by substitution of one or more hydrogen atoms thereof by the above-mentioned "halogen" atom or atoms. When the halogen atom is fluorine, for instance, fluoromethyl, difluoromethyl, trifluoromethyl, 2-fluoroethyl, 2,2,2-trifluoroethyl, 3-fluoropropyl, 3,3,3-trifluoropropyl and 2-fluoro-1-methylethyl may be mentioned as typical examples.

The "hydroxy-lower alkyl group" menas a group derived from the above-mentioned "lower alkyl group" by substitution of one hydrogen atom thereof by a hydroxy .group and, more specifically, includes, among others, hydroxymethyl, 2-hydroxyethyl, 3-hydroxypropyl, 2-hydroxypropyl, 2-hydroxy-1-methylethyl, 4-hydroxybutyl, 3-hydroxybutyl, 2-hydroxybutyl, 3-hydroxy-2-methylpropyl, 5-hydroxypentyl and 6-hydroxyhexyl.

The "hydroxy-lower alkylene group" includes, among others, hydroxymethylene, 1-hydroxyethylene, 2-hydroxyethylene, hydroxymethylmethylene, 1-hydroxytrimethylene, 2-hydroxytrimethylene, 3-hydroxytrimethylene, 2-hydroxytetramethylene, 2-hydroxypentamethylene and 2-hydroxyhexamethylene.

The "lower alkylene group which may optionally be substituted by a hydroxy or lower alkoxy group" includes lower alkylene groups such as those mentioned above, hydroxy-lower alkylene groups such as those mentioned above, and lower alkoxy-lower alkylene groups such as those mentioned above, and lower alkoxy-lower alkylene groups which, when a methoxy group is taken as an example of the substituent lower alkoxy group, include, among others, methoxymethylene, 1-methoxyethylene, 2-methoxyethylene, methoxymethylmethylene, 1-methoxytrimethylene, 2-methoxytrimethylene, 3-methoxytrimethylene, 1-methoxytetramethylene, 4-methoxytetramethylene, 1-methoxypentamethylene, 5-methoxypentamethylene, 1-methoxyhexamethylene and 6-methoxyhexamethylene.

The "hydroxy-lower alkylamino group" means a group derived from an amino group by substitution of one hydrogen atom thereof by the above-mentioned "hydroxy-lower alkyl group" and, more specifically, includes, among others, hydroxymethylamino, 2-hydroxyethylamino, 3-hydroxypropylamino, 2-hydroxy-1-methylethylamino, 4-hydroxybutylamino, 5-hydroxypentylamino and 6-hydroxyhexylamino.

The "lower alkylene group which may optionally be substituted", when substituted, preferably has an amino or mono- or di-lower alkylamino group as the substituent. Typical examples of the mono- or di-lower alkylamino group have already been mentioned hereinabove.

The "carbocylic group" means a nonaromatic carbocyclic group, cycloalkyl or cycloalkenyl group, which in itself is not an aromatic carbocyclic ring but may preferably be condensed with a benzene ring, and, more specifically, includes, among others, cyclopropyl, cyclobutyl, cyclopentyl, cyclohexyl, cycloheptyl, cyclopentenyl, cyclohexenyl and indenyl.

The carbocyclic group may have one or more substituents preferably selected from among lower alkyl groups such as those mentioned above, a hydroxy group, an oxo group, lower alkoxycarbonyl groups such as those mentioned above, a hydroxyimino group and lower alkoxyimino groups such as methoxyimino, ethoxyimino, propoxyimino, isopropoxyimino, butoxyimino, pentyloxyimino and hexyloxyimino.

The "aryl group" means an aromatic hydrocarbon group and includes, as preferred species, phenyl and naphthyl. The aryl group may have one or more substituents each independently selected from among halogen atoms such as those mentioned hereinabove, a nitro group, etc.

The "aralkyl group" means a group derived from the above-mentioned "lower alkyl group" by substitution of at least one hydrogen atom thereof by the above-mentioned "aryl group". More specifically, when a phenyl group is taken as an example of said aryl group, said aralkyl group includes, among others, benzyl, phenethyl, 3-phenylpropyl, 2-phenylpropyl, 2-phenyl-1-methylpropyl, 4-phenylbutyl, 3-phenylbutyl, 3-phenyl-2-methyl propyl, 5-phenylpentyl, 6-phenylpentyl, benzhydryl and trityl.

The aralkyl group may have one or more substituents, for example a halogen atom or atoms such as those mentioned hereinabove and/or a nitro group or groups on the aryl ring and/or a hydroxy group on the alkyl chain.

The aryl moiety of the "arylamino group" and of the "arylsulfonyl group" includes phenyl and naphthyl as preferred species, as in the case of the above-mentioned "aryl group". Preferred examples of the arylamino group and arylsulfonyl group are thus phenylamino, 1-naphthylamino, 2-naphthylamino, phenylsulfonyl, 1-naphthylsulfonyl and 2-naphthylsulfonyl.

The "aralkylamino group" is a group derived from an amino group by substitution of one hydrogen atom thereof by the above-mentioned "aralkyl group". Benzylamino may be mentioned as a typical example when a benzyl group is taken as an example of the aralkyl group.

The "heterocyclic group" includes, among others, 5- or 6-membered heterocyclic groups which may optionally be condensed with a benzene ring, for example furyl, thienyl, pyrrolyl, pyrrolidinyl, pyranyl, pyridyl, oxazolyl, isoxazolyl, thiazolyl, isothiazolyl, thiazolinyl, imidazolyl, imidazolinyl, pyrazolyl, oxadiazolyl, thiadiazolyl, triazolyl, tetrazolyl, pyrimidyl, pyrazinyl, pyridazinyl, thiazinyl, benzofuranyl, isobenzofuranyl, benzothienyl, indolyl, isoindolyl, chromenyl, quinolyl, isoquinolyl, phthalazinyl and quinoxalinyl.

Preferred among them are those nitrogen-containing monocyclic or bicyclic heteroaromatic groups which can be converted to the N-oxide form, for example pyridyl, pyrimidinyl, pyrazinyl, pyridazinyl, quinolyl, isoquinolyl, phthalazinyl and quinoxalinyl, these nitrogen-containing nonaromatic monocyclic or bicyclic heterocyclic groups which are available for bonding through the nitrogen atom thereof and can be substituted by an oxo group to form a lactam ring, for example pyrrolidinyl, piperidinyl, indolyl and isoindolyl, such nitrogen-containing heterocyclic groups as benzimidazolyl and such oxygen-containing heterocyclic groups as furyl, oxolanyl and pyranyl.

These heterocyclic groups may have one or more substituents each independently selected from among halogen atoms, lower alkyl groups, a hydroxy group, lower alkoxy groups, an oxo group, a carbamoyl group, mono- or di-lower alkylaminocarbonyl groups, etc. Nitrogen-containing heteroaromatic groups may further have an M-oxide forming oxygen as a substituent thereon. Typical examples of these substituents are as mentioned hereinabove.

Particularly preferred among the compounds (I) according to the invention are those compounds in which one of $R^2$ and $R^3$ is a nitro or cyano group or a halogen atom and the other is a hydrogen atom or a nitro group, those compounds in which $R^7$ is a nitrogen-containing heterocyclic group which may optionally be in the N-oxide form and/or substituted by a lower alkyl group or groups, for example oxo-2-pyridil group or 6-methyl-1-oxo-2-pyridyl group, an oxo-substituted nitrogen-containing heterocyclic group, such as 2-oxo-1-pyrrolidinyl, an oxo-substituted carbocyclic group, such as 2-oxocyclopentyl or 5-oxo-1-cyclopenten-1-yl, a group of the formula -$A^1$-$R^8$ ($A^1$ and $R^8$ being as defined above), for example (1-oxo-2-pyridyl)methyl, or a group of the formula

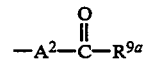

($A^2$ and $A^9$ being as defined above), for example acetonyl, phenacyl, carbamoylmethyl, N-methylaminocarbonylmethyl or N,N-dimethylaminocarbonylmethyl.

The compounds (I) according to the present invention may form salts with acids, as the case may be. They may form salts with bases depending on the substituent or substituents. Such salts include addition salts with inorganic acids such as hydrochloric acid, hydrobromic acid, hydroiodic acid, sulfuric acid, nitric acid and phosphoric acid, and with organic acids such as formic acid, acetic acid, propionic acid, oxalic acid, malonic acid, succinic acid, fumaric acid, maleic acid, malic acid, tartaric acid, methanesulfonic acid and ethanesulfonic acid, addition salts with acidic amino acids such as aspartic acid and glutamic acid, salts with inorganic bases such as sodium, potassium, magnesium, calcium and aluminum, with organic bases such as methylamine, ethylamine and ethanolamine, and with basic amino acids such as lysine and ornithine, and the ammonium salt.

The compounds according to the present invention may have a double bond and/or an asymmetric carbon atom or atoms depending on the substituent or substituents. Accordingly, the compounds according to the present invention include within the scope thereof the resulting various isomers, for example geometric isomers, tautomers and optical isomers, either in an each individual isolated isomer form or in a mixture form.

The compounds (I) according to the present invention can be produced by applying various synthetic methods taking advantage of the characteristics of the skeletal structure and/or various substituents. Typical examples of applicable production processes are given below.

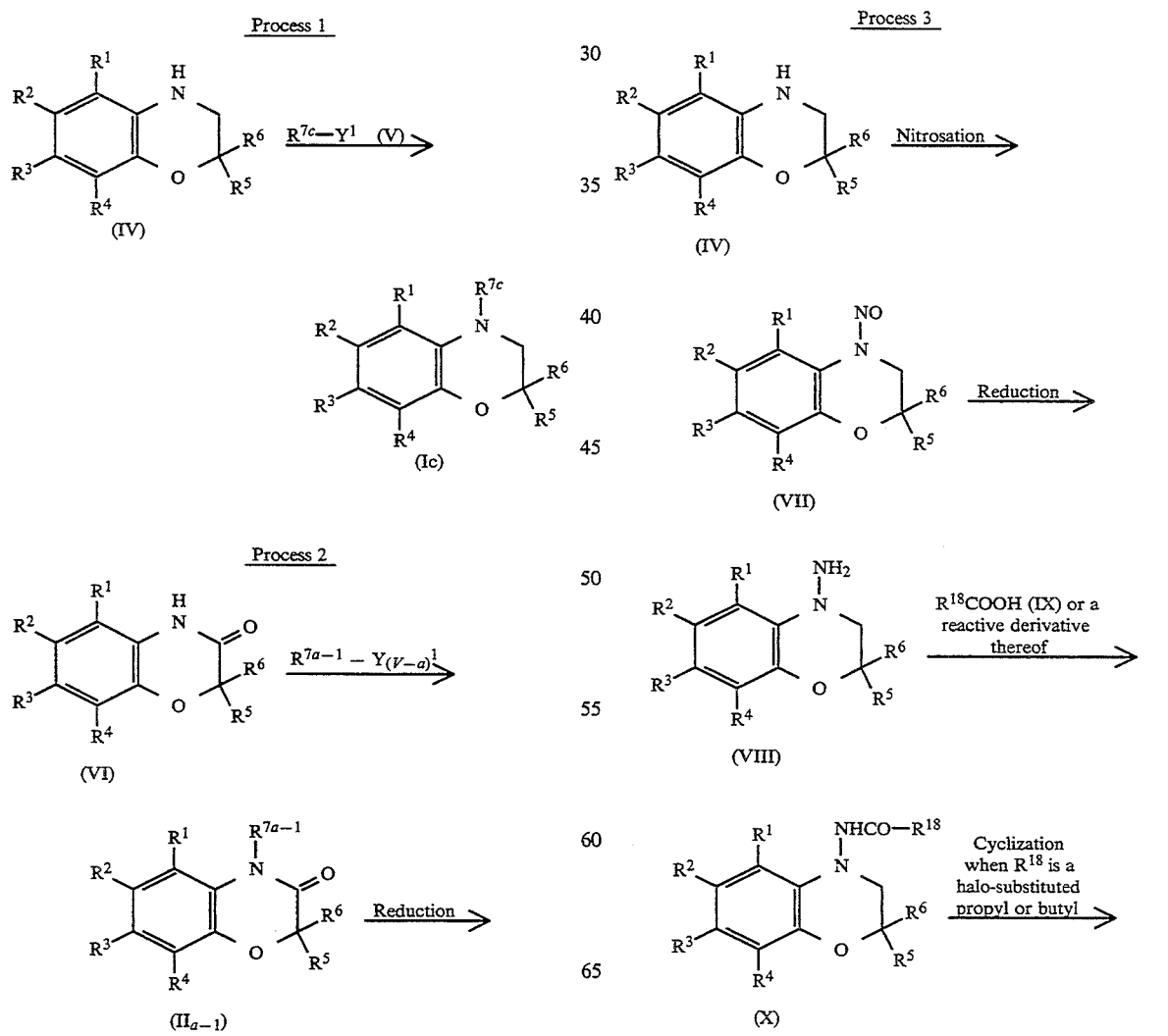

-continued

Process 3

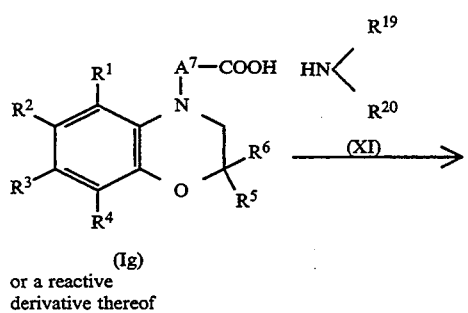
(If)

Process 4

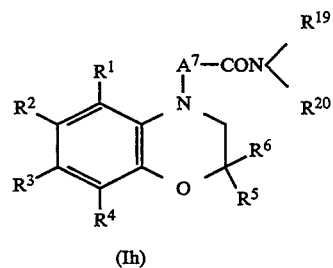
(Ig)
or a reactive derivative thereof

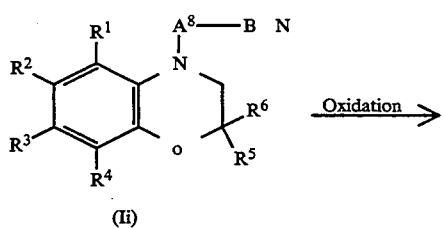
(Ih)

Process 5

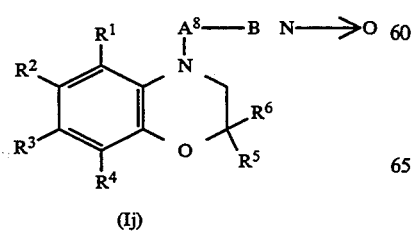
(Ii)

↓ Oxidation

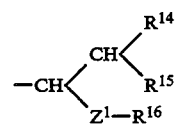
(Ij)

Process 6

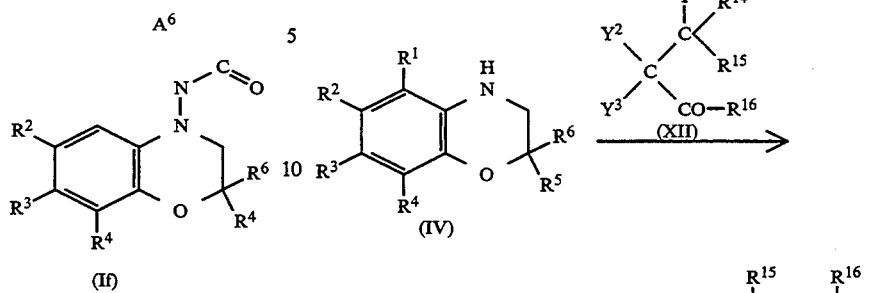

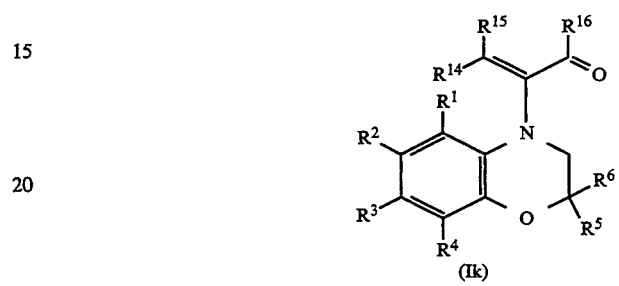
(Ik)

In the above formulas, $R^1$, $R^2$, $R^3$, $R^4$, $R^{1'}$, $R^{2'}$, $R^{3'}$, $R^{4'}$, $R^5$, $R^6$, $R^7$, $A^1$, $R^8$, $A^2$, $R^9$, $A^3$, $R^{10}$, $A^4$, $R^{11}$ and $R^{12}$ are as defined above and the other symbols are defined as follows:

$R^{7c}$ represents a heterocyclic group which is available for bonding through a ring-forming carbon atom (not a hetero atom) and may optionally have a substituent or substituents, a group of the formula $-A^{1c}-R^{8c}$ (in which $A^{1c}$ is a lower alkylene group and $R^{8c}$ is an aryl group which may optionally be substituted, a heterocyclic group which may optionally be substituted, or a lower alkenyloxy group, when $A^{1c}$ represents a non substituted lower alkylene, $R^8$ does not represent a phenyl group), a group of the formula

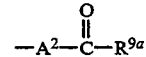

(in which $A^2$ and $R^9$ are as defined above), a group of the formula

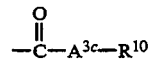

(in which $R^{10}$ are as defined above and $A^{3c}$ is a single bond or a lower alkylene or lower alkenylene group) or a group of the formula $$-CH\begin{matrix}CH\begin{matrix}R^{14}\\R^{15}\end{matrix}\\Z^1-R^{16}\end{matrix}$$

(in which $R^{14}$ is a hydrogen atom or a lower alkyl or lower alkoxycarbonyl group, $R^{15}$ and $R^{16}$ which may be the same or different, each independently is a lower alkyl group or combinedly represent a lower alkylene, o-phenylene or carbonyl group to form a ring, and $Z^1$ is a carbonyl, methylene or carbinol group;

$Y^1$ represents a halogen atom or an alkyl or aryl sulfonyloxy group or ester residue;

$R^{7a-1}$ represents a group of the formula

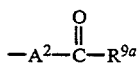

($A^2$ and $R^9$ being as defined above) or a group of the formula

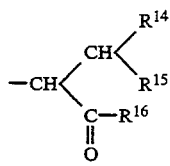

($R^{14}$, $R^{15}$ and $R^{16}$ being as defined above);

$A^5$ represents a group represented by $A^2$ or a group of the formula

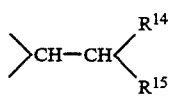

($R^{14}$ and being as defined above);

$R^{17}$ is a group represented by $R^9$ or $R^{16}$ (each being as defined above);

represents a halo-substituted propyl or halo-substituted butyl;

$A^6$ represents a trimethylene or tetramethylene group;

$A^7$ represents a lower alkylene group or a group of the formula

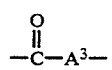

($A^3$ being as defined above);

$R^{19}$ and $R^{20}$ are the same or different and each independently is a hydrogen atom or a lower alkyl group or combinedly, together with the adjacent nitrogen atom, form a heterocyclic group which may have a substituent or substituents;

$A^8$ represents a single bond. A group represented by $A^1$ or $A^2$ or a group of the formula

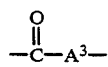

($A^3$ being as defined above);

——B N represents a nitrogen-containing monocyclic or bicyclic heteroaromatic group which may optionally be substituted;

$Y^2$ represents a halogen atom or, when taken together with $Y^3$, represents a carbonyl oxygen atom;

$Y^3$ represents a halogen atom or, when taken together with $Y^2$ represents a carbonyl oxygen atom, or a hydrogen atom when $Y^4$ is a halogen atom; and $Y^4$ represents a hydrogen atom when $Y^2$ and $Y^3$ are both halogen atoms or combinedly represent a carbonyl oxygen atom, or represents a halogen atom when $Y^2$ is a halogen atom and $Y^3$ is a hydrogen atom.

The halogen atom represented by $Y^1$, $Y^2$, $Y^3$ or $Y^4$ or $R^{18}$ is preferably an iodine, bromine or chlorine atom while an alkyl or aryl sulfonyloxy group represented by $Y^1$ is preferably methanesulfonyloxy, benzenesulfonyloxy or toulenesulfonyloxy (in particular p-toluenesulfonyloxy). The ester residue represented by $Y^1$ is, for example, a lower alkoxy group, such as methoxy or ethoxy, or the residue of an active ester with N-hydroxybenzotriazole, N-hydroxysuccinimide or the like.

In the following, the above processes are described in further detail.

Process 1

Among the compounds according to the invention, the compounds of general formula (Ic) can be synthesized by the so-called N-alkylation or N-acylation which comprises reacting a benzoxazine derivative of the formula (IV), which has a free nitrogen atom, with a halide, sulfonate or ester of the formula (V).

This reaction is carried out generally in an organic solvent inert to the reaction, for example N,N-dimethylformamide, dimethyl sulfoxide, hexamethylphosphoramide, ether, dioxane, tetrahydrofuran, methylene chloride, dichloroethane, chloroform, benzene, toluene or xylene, although the reaction may proceed in the absence of a solvent.

In carrying out the reaction, it is advantageous to use a base, such as trimethylamine, triethylamine, sodium hydride, potassium hydride, an alkali metal alcoholate (e.g. potassium tert-butoxide) or potassium carbonate, or a copper catalyst, such as copper, copper iodide or copper sulfate.

The reaction temperature is not critical but may suitably be selected depending on the reactants. Thus the reaction is carried out with cooling, at room temperature, or under heating.

Process 2

Those benzoxazine derivatives of the formula (Id) which have a hydroxyalkyl group can be produced by the so-called N-alkylation or N-acylation which comprises reacting an 3-oxobenzoxazine derivative of the formula (VI) with a halide, sulfonate or ester of the formula (V-a), followed by reduction of the resulting 3-oxo-4-substituted carbonylalkylbenzoxazine derivative of the formula (IIa-1).

Those compounds of the formula (Ie) which have a carbonyl group can be produced by oxidizing the compounds (Id) obtained in the above manner.

The N-alkylation or N-acylation in the first step can be conducted in the same manner as in Process 1.

The second-step reduction is advantageously effected by adding a compound (IIa-1) or the reaction mixture from the first step to a reducing agent, such as borane, preferably borane-tetrahydrofuran complex (which is commercially available), followed by heating or by heating under refluxing.

The third step oxidation is advantageously carried out in the manner of Swern oxidation or Jones oxidation although any other method for oxidizing a carbinol group to a carbonyl group cab be employed. In the case of Swern oxidation, for instance, the reaction is carried out in an organic solvent inert to the reaction, such as methylene chloride, preferably in an inert gas atmosphere and with cooling (about −60° C.). Under such conditions, the intermediate (Id) is treated with activated DMSO (which is prepared from oxalyl chloride and dimethyl sulfoxide), and then with triethylamine.

Process 3

Among the compounds according to the present invention, those compounds of the formula (If) which have a lactam ring bound, via the nitrogen atom thereof, to the benzoxazine ring at the 4-position thereof can be produced by subjecting the corresponding halobutyrylamino or halovalerylamino compounds (X) to cyclization.

The cyclization (ring formation) reaction is carried out under substantially the Same conditions as used in the N-alkylation in Process 1 using an acid halide. An alkali metal alcoholate, such as potassium tert-butoxide, is advantageously used as the base.

The intermediates (X) can be prepared by nitrosating a compound (IV), reducing the resulting nitroso compound (VII) and reacting the resulting amino compound (VIII) with a carboxylic acid of the formula (IX) or a reactive derivative thereof.

For the nitrosation, the compound (IV) is reacted with a nitrosating agent, such as sodium nitrite, nitrous acid or a nitrite ester, in an inert solvent, such as an alcohol (e.g. methanol, ethanol, isopropanol) or acetic acid-water, under acidic conditions with cooling to maintain a temperature not higher than 20° C., preferably not higher than 10° C. and then after heat generation has subsided, at room temperature.

The reduction is generally carried out in an organic solvent inert to the reaction, for example an alcohol such as methanol, ethanol or isopropanol, in the presence of a base, such as sodium hydroxide, with cooling or at room temperature, using an appropriate reducing agent, for example formamidinesulfinic acid or a boron hydride compound such as diborane or sodium borohydride. In some instances, the reduction may be performed in the manner of catalytic hydrogenation using Raney nickel, palladium-carbon, platinum black or palladium as the catalyst or in the manner of chemical reduction using iron, tin or zinc in combination with an acid such as hydrochloric acid, sulfuric acid or acetic acid.

The amidation is carried out in a conventional manner. As the reactive derivative of the compound (IX), there may be mentioned an ester, such as methyl ester or ethyl ester, an acid chloride, such as acid chloride or acid bromide, an acid azide, an active ester, such as N-hydroxybenzotriazole ester or N-hydroxysuccinimide ester, the symmetric acid anhydride and a mixed acid anhydride with an alkylcarbonic acid, p-toluenesulfonic acid, diphenylphosphoryl chloride or the like. When the compound (IX) is subjected to amidation in its free form, a condensing agent, such as dicyclohexylcarbodiimide, 1,1'-carbonyldiimidazole, diphenylphosphoryl azide or diethylphosphoryl cyanide. The reaction is carried out in an organic solvent inert to the reaction, for example an alcohol such as methanol, ethanol or isopropanol, N,N-dimethylformamide, pyridine, tetrahydrofuran, dioxane, ether, benzene, toluene, xylene, methylene chloride, dichloroethane, chloroform, ethyl acetate or acetonitrile, generally at room temperature or with warming or, for certain reactive derivatives, with cooling, in the presence of a base, for example an organic base, such as pyridine, picoline, lutidine, dimethylaniline or N-methylmorpholine, or an inorganic base, such as potassium carbonate, sodium carbonate, sodium hydrogen carbonate, sodium hydroxide or potassium hydroxide, using the compound (IX) or a reactive derivative thereof in an equimolar or excessive amount relative to compound (VIII).

Process 4

Among the compounds according to the invention, the compounds of the formula (Ih) can be produced by reacting (amidating) a carboxylic acid of the formula (Ig) or a reactive derivative thereof with an amine of the formula (IX) or a salt thereof.

The amidation reaction can be conducted in the same manner and under the same reaction conditions as in the amidation for preparing intermediates (X) in Process 3 mentioned above.

When an ester compound corresponding to compound (Ig) is available, the ester compound may be subjected to hydrolysis and the resulting compound (Ig) to the above-mentioned amidation. The hydrolysis is preferably carried out in a conventional manner in the presence of an acid, such as trifluoroacetic acid, or a base, such as sodium hydroxide or potassium hydroxide.

Process 5

The N-oxide compounds of the formula (Ij) can be produced by oxidizing the corresponding nitrogen-containing heterocyclic compounds (Ii).

The oxidation Can be carried out in-an organic solvent inert to the reaction, for example methylene chloride, dichloroethane, chloroform, carbon tetrachloride, an alcohol such as methanol, or ether, at room temperature or with warming, using an oxidizing agent, for example hydrogen peroxide, an inorganic peracid, such as perphosphoric acid, chromic anhydride, persulfuric acid or potassium persulfate, or an organic peracid, such as perbenzoic acid, m-chloroperbenzoic acid, performic acid, trifluoroperacetic acid, perphthalic acid, permaleic acid or peracetic acid.

Process 6

Among the compounds according to the present invention, the compounds of the formula (Ik) can be produced by reacting a compound (IV) with a dihalide or diketone of the formula (XII).

The dihalide compound can be prepared by reacting the corresponding carbonyl compound having active hydrogen in the position alpha to carbonyl with a halogenating agent, such as a halogen gas, N-bromosuccinimide, sulfuryl chloride or copper chloride, in an inert organic solvent, such as dichloromethane, dichloroethane, chloroform, carbon tetrachloride, N,N-dimethylformamide, ether, dioxane, benzene or acetic acid, in the presence of an acid catalyst or radical initiator, such as benzoyl peroxide, azobisisobutyronitrile or a hydrogen halide, at room temperature or under heating, as illustrated by the reaction formula shown below.

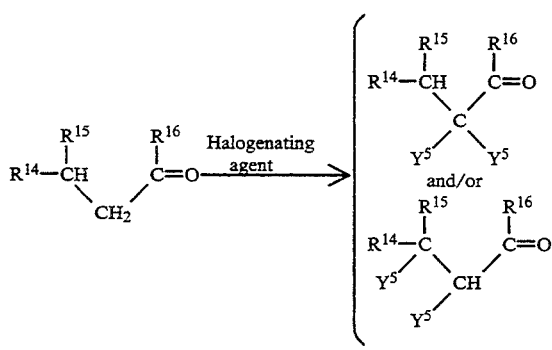

(In the above reaction formula, $R^{14}$, $R^{15}$ and $R^{16}$ are as defined above and $Y^5$ represents a halogen atom.)

The reaction of the compound (IV) with the dihalide or diketone is advantageously carried out in an organic solvent inert to the reaction, such as methylene chloride, dichloroethane, chloroform, carbon tetrachloride, ether, dioxane, tetrahydrofuran, benzene, toluene or xylene, in the presence of an acid catalyst, for example an organic acid such as p-toluenesulfonic acid or methanesulfonic acid or a Lewis acid such as titanium tetrachloride, when the compound (IV) is reacted with the diketone, or in the presence of a base such as trimethylamine, triethylamine, pyridine, picoline, lutidine, N,N-dimethylaniline or N-methylmorpholine when the compound (IV) is reacted with the dihalide, with heating, preferably with heating under refluxing, using the compound (XII) in an equimolar or excessive amount relative to the compound (IV).

The intermediates (II), which differ from the compounds according to the present invention in that they have an oxo group at the 3-position of the benzoxazine skeleton, can be produced by essentially the same methods as those mentioned above for the compounds according to the present invention unless the carbonyl group is reduced as in Process 2.

Thus, for instance, those compounds of formula (II) in which $R^{7a}$ is a nitrogen-containing heterocyclic group which may optionally be substituted by at least one of an oxo group and a lower alkyl group and may be in the form of an N-oxide can be produced by applying the above-mentioned Process 1, 3 or 5. Those compounds of formula (II) in which $R^{7a}$ is a carbocylic group which may optionally be substituted by an oxo group can be produced by applying Process 6. Those compounds of formula (II) which have a group represented by the formula -$A^1$-$R^{8a}$ can be produced by Process 1 or 5 and those compounds of formula (II) which have a group of the formula

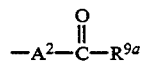

can be produced by Process 1 or 4.

To give the final products, namely the compounds (I) according to the invention, the intermediates (II) are subjected to Process 2 when their 4-position substituent contains a carbonyl group readily reducible with such a reducing agent as borane. When the 4-position substituent is an unreducible one, the intermediates (II) can directly be reduced with borane to give the corresponding compounds (I).

The intermediates (III) can be produced by applying the methods (step 1 and step 2) involved in Process 3 and the compounds according to the invention can be derived therefrom by applying the subsequent steps of Process 3.

The reaction period to be employed in each reaction step in the processes mentioned above should suitably be determined depending on various reaction conditions.

The product given by each reaction can be easily isolated and purified.

For instance, after completion of the reaction, the reaction mixture is poured into an excessive amount of water or ice water, the organic matter is extracted with an appropriate organic solvent, such as methylene chloride, chloroform, benzene, diethyl ether or ethyl acetate, the extract layer is then dried, the solvent is evaporated, and the residue is purified by recrystallization or silica gel column chromatography on silica gel to give the desired intermediate or product in a purified form. The solvent for recrystallization and/or column chromatography may suitably be selected from among hexane, benzene, methylene chloride, chloroform, ethyl acetate, acetone, ethanol, methanol, etc., and mixtures of these.

In some instances, the reaction product may precipitate out as crystals with the progress of the reaction. In such cases, the product can be more readily isolated and purified by collecting the crystalline precipitate by filtration and recrystallizing the same from an appropriate organic solvent.

As mentioned above, be compounds according to the invention may include various types of stereoisomers. Geometric isomers and tautomers can be separated into individual isomers and each isomer can be purified by taking advantage of a difference or differences in physical properties between the isomers, for instance.

Optical isomers can be produced by using appropriate starting compounds or obtained in a purified form by a technique generally used for optical resolution of racemic mixtures, for example the technique of optical resolution which comprises the formation of diastereomer salts with an optically active acid (in particular tartaric acid) in general use for the above purpose.

The compounds provided by the present invention have K+ channel activating activity and are useful for the prevention and treatment of ischemic heart diseases such as angina pectoris and myocardial infarction as well as cardiovascular diseases such as hypertension and related diseases (arteriosclerosis, obesity, hyperlipemia, etc.), congestive heart failure, arrhythmia and peripheral vascular disorders (alopecia etc.), among others.

Furthermore, the compounds according to the present invention are useful as therapeutic agents for various disorders associated with smooth muscle contraction, such as cerebrovascular disorders (cerebrovascular spasms, migraine, dizziness, etc.), respiratory disorders (reversible airway obstruction, hypersensitive airway obstruction, asthma, etc.), gastrointestinal disorders (ulcer, nervous gastrointestinal disease, irritable colon syndrome, diverticulosis, biliary obstruction, etc.), visual and auditory disorders (disorders of inner ear, disorders of auditory organs, glaucoma, dysopia, ocular hypertension, etc.), urinary tract disorders (renal failure, disorders associated with passage of renal stones, pollakiuria, dysuria, incontinence, etc.), genital organ disorders (premature labor, dysmenorrhea, etc.)

and the like. In addition, the compounds of the present invention are of value as therapeutic agents for disorders due to abnormal blood sugar level (hypoglycemia, diabetes, etc.) and to abnormality of the cardiac conduction system (arrhythmia etc.).

These pharmacological actions of the compounds according to the present invention can be demonstrated using the test methods mentioned below. Thus, the K+ channel activating action of the compounds was demonstrated in the concentration range from $10^{-9}$ to $10^{-4}$ M in isolated tissue. The compounds, when given intravenously, reduced the blood pressure and increased the coronary blood flow in the dose range of 1 to 1,000 μg/kg and, when administered into the coronary artery, they dilated the coronary artery in the dose range of 0.3 to 100 μg. Furthermore, hypotensive and coronaryvasodilating activities of the some compounds according to the present invention were found to be effective for a long period of time.

The test methods for supporting the pharmacological effects of several typical compounds among the compounds according to the present invention are described below.

TEST METHODS (1) Effects on 3,4-diaminopyridine-induced rhythmic contractions The method of Uchida and Sugimoto (Myakkangaku, 24, 133-143, 1984) was used. Mongrel dogs of either sex were anesthetized with pentobarbital (30 mg/kg i.v.) and bled to death and, then, the heart was excised from each animal. In the Krebs-Henseleit solution, the left coronary circumflex branch or the anterior descending branch was isolated and cut into rings, about 2 mm in width. The ring segment was fixed to a stainless steel hook and suspended in a Krebs-Henseleit bath (37° C.) aerated with 95%O$_2$-5%CO$_2$ gas mixture under a tension load of 1.0 g, and isometric contractions were recorded.

After the specimen was stabilized for 30 minutes, rhythmic contractions were induced by addition of 3,4-diaminopyridine (10 mM). When the amplitude and frequency of rhythmic contractions became substantially steady, cumulative addition of the test compound to the organ bath was started. The concentration-response curves for the amplitude and frequency of contractions were constructed and the efficacy was evaluated.

The inhibitory effect on the frequency of contractions is shown in Column (1) in Table 1.

(2) Effects on the cardiovascular system

Mongrel dogs of either sex were anesthetized with pentobarbital, 30 mg/kg i.v. and, after tracheal intubation, the experiment was performed under artificial respiration. After thoracotomy, heart rate, blood pressure, left ventricular pressure, max dLVP/dt, pulmonary arterial pressure, central venous pressure, cardiac output and coronary blood flow were measured. The test compound was administered through a cannula indwelt in the femoral vein and the efficacy was evaluated.

Column (2) in Table 1 shows the mean blood pressure (MBP)-lowering effect in terms of the percent reduction (Δ%). (3) Coronary vasodilating effect Mongrel dogs of either sex were anesthetized with pentobarbital, 30 mg/kg i.v. and subjected to the experiment under artificial respiration with tracheal intubation. After thoracotomy, the left coronary circumflex branch was perfused with the autologous blood derived from the common carotid artery at a constant pressure through an extracorporeal circuit. Coronary blood flow was measured with an electromagnetic flow probe installed in the extracorporeal circuit. The test compound is administered directly into the coronary artery through the extracorporeal circuit and the coronary vasodilating effect was assessed.

As the indicator of the coronary vasodilative effect of the test compound, the percentage of the response was determined with the response to coronary arterial administration of 300 μg of papaverine being taken as 100% and the dose sufficient to produce a blood flow increase of 100% (ED$_{100\,pap}$) was calculated.

TEST RESULTS

TABLE 1

| Example No. | (1) IC$_{50}$ (μM) | (2) MBP [μg/kg i.v. (Δ%)] |
|---|---|---|
| 1 | 0.01 | 3 (−16) |
| 2 | 0.24 | 10 (−20) |
| 38 | 0.07 | 10 (−23) |
| 41(4) | 0.05 | 3 (−20) |
| 56 | 0.02 | 3 (−11) |
| 70 | 0.01 | 10 (−9) |
| Cromakalim | 0.39 | 10 (−28) |

Then, in connection with Examples 1 and 2, the hypotensive effect of the test compound given orally in conscious spontaneously hypertensive rats (SHR) and the intravenous acute toxicity in mice were determined.

TEST METHOD (1) Hypotensive effect

Spontaneously hypertensive rats (SHR) of Okamoto-Aoki strain were anesthetized with pentobarbital, 60 mg/kg i.p. Then, a cannula for blood pressure measurement was indwelt in the left common carotid artery and the other end of the cannula was led out extracorporeally from the posterior neck. After a stabilization period of 4-5 postoperative days, the blood pressure and heart rate were measured without restraint under no anesthesia. The test compound was suspended in 0.5% methylcellulose solution and the suspension was orally administered in a volume of 5 ml/kg and the efficacy was evaluated.

Table 2 shows the mean blood pressure (MBP)-lowering effect in terms of Δ%.

(2) Acute toxic effect

The acute toxic dose (LD$_{50}$) of the test compound administered into the caudal vein was determined by the up and down method in male mice.

Table 3 shows acute toxic doses (LD$_{50}$).

TEST RESULTS

TABLE 2

| Example No. | Dose (μg/kg p.o.) | MBP (Δ%) |
|---|---|---|
| 1 | 30 | −25 |
| 2 | 300 | −40 |
| Cromakalim | 300 | −35 |

TABLE 3

| Example No. | LD$_{50}$ (mg/kg i.v.) |
| --- | --- |
| 1 | 50.4 |
| 2 | >60 |
| Cromakalim | 49.7 |

The compounds (I) according to the present invention or salts thereof can be used as potassium channel activators in the form of conventional pharmaceutical preparations containing one or more of said compounds or salts thereof as active ingredients, together with the usual carrier, excipient and/or other additives, and suited for oral or nonoral administration, for example in the form of tablets, buccal tablets, powders, fine granules, granules, capsules, pills, liquid preparations for oral administration (inclusive of syrups), injections, inhalants, suppositories, liquid preparations for percutaneous administration, ointments, transdermal therapeutic systems or transmucosal therapeutic systems (e.g. for intraoral use), liquid preparations for permucosal administration (e.g. liquid nasal preparations) and so on.

The carriers or excipients for use in said various preparations are pharmaceutically acceptable and nontoxic solid or liquid substances, for example lactose, magnesium stearate, starch, talc, gelatin, agar, pectin, gum arabic, olive oil, sesame oil, cacao butter, ethylene glycol and other substances in common pharmaceutical use.

The clinical dose of the compounds according to the present invention should suitably be decided depending on the disease to be treated, symptom, patient's body weight, age and sex, route of administration and other factors. Generally, however, the daily dose for human adults lies within the range of 0.1 to 300 mg per adult in the case of oral administration and 0.06 to 100 mg per adult in the case of intravenous administration. Such dose is administered in a single dose or in two to four divided doses.

The following examples and dosage form examples are further illustrative of the present invention. The starting compounds include some novel compounds. Typical processes for preparing such novel compounds from known compounds are described in the reference examples which follow. Unless otherwise indicated, the ratios used hereinafter are by volume.

REFERENCE EXAMPLE 1

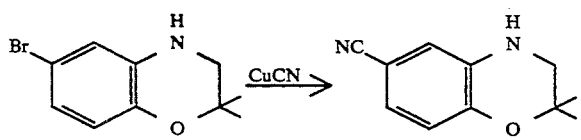

A mixture of 480 mg of 6-bromo-3,4-dihydro-2,2-dimethyl-2H-1,4-benzoxazine, 206 mg of cuprous cyanide and 5 ml of N,N-dimethylformamide was stirred at 130° C. for 4 hours and further at 150° C. for 5 hours. This reaction mixture was diluted with 0.5 ml of ethylenediamine and 10 ml of water and extracted with benzene. The organic layer was washed with water and dried over anhydrous magnesium sulfate and the solvent was distilled off. The residue was chromatographed on a silica gel column and elution was carried out with ethyl acetate-hexane (10:1). The crude crystals from the eluate were washed with hexane and dried to give 160 mg of 6-cyano-3,4-dihydro-2,2-dimethyl-2H-1,4-benzoxazine. This compound has the following physicochemical properties.

i) Melting point: 102°–103.5° C.

ii) NMR spectrum (CDCl$_3$)

δ(ppm): 1.37 (6H, s), 1.5–2.5 (1H, s), 3.12 (2H, s), 6.77 (1H, d), 6.86 (1H, d), 6.97 (1H, dd)

REFERENCE EXAMPLE 2

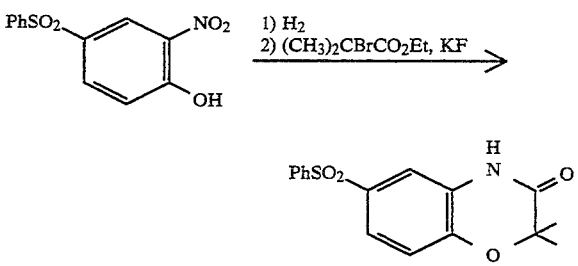

In 120 ml of dehydrated ethanol was suspended 11.05 g of 2-nitro-4-phenylsulfonylphenol followed by addition of a catalytic amount of Raney nickel for reduction in a hydrogen stream at atmospheric temperature and pressure. After completion of the reduction reaction, the catalyst was filtered off and the solvent was distilled off. The residue was dried under reduced pressure to give 9.73 g-of crude 2-amino-4-phenylsulfonylphenol. This product was dissolved in 19 ml of N,N-dimethylformamide and the solution was added dropwise to a mixture of 5.89 g of potassium fluoride, 7.61 g of ethyl 2-bromoisobutyrate and 11 ml of N,N-dimethylformamide. The mixture was then stirred at 60° C. overnight. The reaction mixture was poured in ice-water and extracted with ethyl acetate. The organic layer was washed with water and dried over anhydrous magnesium sulfate and the solvent was distilled off. The residue was chromatographed on a silica gel column and elution was carried out with hexane-ethyl acetate (2:1). The crude crystals from the eluate were recrystallized from 15 ml of ethanol to recover 4.706 g of 3,4-dihydro-2,2-dimethyl-3-oxo-6-phenylsulfonul-2H-1,4-benzoxazine.

This compound has the following physicochemical properties.

i) Melting point: 153°–157° C.

ii) Elemental analysis (for C$_{16}$H$_{15}$NO$_4$S)

|  | C (%) | H (%) | N (%) | S (%) |
| --- | --- | --- | --- | --- |
| Calcd.: | 60.55 | 4.76 | 4.41 | 10.10 |
| Found: | 60.62 | 4.79 | 4.25 | 10.13 | iii) NMR spectrum (CDCl$_3$)

δ(ppm): 1.52 (6H, s), 6.99 (1H, d), 7.3–7.6 (5H, 7.8–8.0 (2H, m), 9.27 (1H, s)

REFERENCE EXAMPLE 3

The following compound was synthesized generally in the same manner as Reference Example 2.

3,4-Dihydro-2,2-dimethyl-6-methylsulfonyl-3-oxo-2H-1,4-benzoxazine

Physicochemical properties:

i) Melting point: 241°–243° C.

ii) Elemental analysis (for C$_{11}$H$_{13}$NO$_4$S)

|  | C (%) | H (%) | N (%) | S (%) |
|---|---|---|---|---|
| Calcd.: | 51.75 | 5.13 | 5.49 | 12.56 |
| Found: | 51.74 | 5.13 | 5.43 | 12.56 | iii) NMR spectrum ( DMSO-d$_6$)
δ(ppm): 1.43 ( 6H, s ), 3.15 (3H, s), 7.15 (.1H, d) 7.3–7.6 (2H, m), 10.54 (1H, s)

REFERENCE EXAMPLE 4

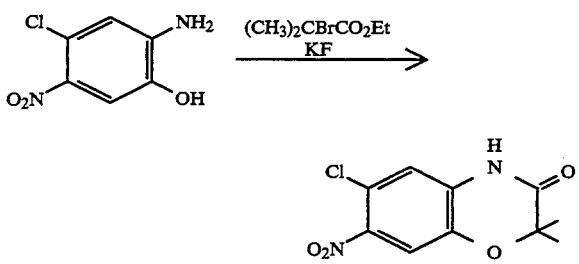

To a mixture of 40 g of potassium fluoride, 40 ml of ethyl 2-bromoisobutyrate and 200 ml of N,N-dimethylformamide was added 49.1 g of 2-amino-4-chloro-5-nitrophenol and the whole mixture was stirred at 60° for 4 days. The reaction mixture was then poured in ice-water and the resulting solid was recrystallized from 800 ml of isopropyl alcohol to give 37.03 g of 6-chloro-3,4-dihydro-2,2-dimethyl-7-nitro-3-oxo-H-1,4-benzoxazine. A 0.51 g portion of the above product was recrystallized from 14 ml of ethanol to give 0.31 g of a sample for elemental analysis.

This compound has the following physicochemical properties.
i) Melting point: 243°–245° C.
ii) Elemental analysis (for C$_{10}$H$_9$ClN$_2$O$_4$)

|  | C (%) | H (%) | N (%) | Cl (%) |
|---|---|---|---|---|
| Calcd.: | 46.80 | 3.53 | 10.92 | 13.81 |
| Found: | 46.84 | 3.46 | 10.90 | 13.91 | iii) NMR spectrum (DMSO-d$_6$)
δ(ppm): 1.43 (6H, s), 7.04 (1H, s), 7.68 (1H, s), 11.23 (1H, s)

REFERENCE EXAMPLE 5

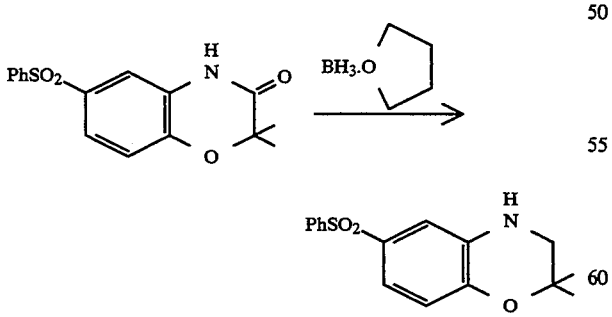

To 35 ml of a solution of borane-tetrahydrofuran complex in tetrahydrofuran (1M) was added 4.625 g of 3,4-dihydro-2,2-dimethyl-3-oxo-6-phenylsulfonyl-2H-1,4-benzoxazine with ice-cooling and the mixture was refluxed under heating with constant stirring for 2 hours. This reaction mixture was diluted with 4.3 ml of methanol and further refluxed for 45 minutes. Then, 3.6 ml of concentrated hydrochloric acid was added and the mixture was further refluxed for 45 minutes. The reaction mixture was then concentrated and the resulting solid was pulverized in ether and filtered. The pulverizate was suspended in a dilute aqueous solution of sodium hydroxide and extracted with ethyl acetate. The organic layer was washed with water and dried over anhydrous magnesium sulfate and the solvent was distilled off. The residue was recrystallized from 15 ml of ethanol to recover 3.76 g of 3,4-dihydro-2,2-dimethyl-6-phenylsulfonyl-2H-1,4-benzoxazine.

This compound has the following physicochemical properties.
i) Melting point: 138°–140.5° C.
ii) Elemental analysis (for C$_{16}$H$_{17}$NO$_3$S)

|  | C (%) | H (%) | N (%) | S (%) |
|---|---|---|---|---|
| Calcd.: | 63.34 | 5.65 | 4.62 | 10.57 |
| Found: | 63.36 | 5.65 | 4.54 | 10.65 | iii) NMR spectrum (CDCl$_3$)
δ(ppm): 1.28 (6H, s), 3.04 (3H, s), 3.2–4.2 (1H), 6.76 (1H, dd), 7.1–7.3 (2H, m), 7.3–7.6 (3H, m), 7.8–8.0 (2H, m)

REFERENCE EXAMPLE 6–8

The following compound was synthesized in the same manner as Reference Example 5.

REFERENCE EXAMPLE 6

3,4-Dihydro-2,2-dimethyl-6-methylsulfonyl-2H-1,4-benzoxazine
Physicochemical-properties:
i) Melting point: 137°–142° C.
ii) Elemental analysis (for C$_{11}$H$_{15}$NO$_3$S)

|  | C (%) | H (%) | N (%) | S (%) |
|---|---|---|---|---|
| Calcd.: | 54.75 | 6.27 | 5.80 | 13.29 |
| Found: | 54.86 | 6.29 | 5.78 | 13.30 | iii) NMR spectrum (CDCl$_3$)
δ(ppm): 1.32 (6H, s), 3.50 (3H, s), 3.09 (2H, d), 6.80 (1H, dd), 7.1–7.3 (2H, 4.33 (1H, s), m)

REFERENCE EXAMPLE 7

6-Chloro-3,4-dihydro-2,2-dimethyl-7-nitro-2H-1,4-benzoxazine
Physicochemical properties:
i) Melting point: 139°–140.5° C.
ii ) Elemental analysis ( for C$_{10}$H$_{12}$ClN$_2$O$_3$)

|  | C (%) | H (%) | N (%) | Cl (%) |
|---|---|---|---|---|
| Calcd.: | 49.50 | 4.57 | 11.54 | 14.61 |
| Found: | 49.45 | 4.53 | 11.52 | 14.57 | iii) NMR spectrum (CDCl$_3$)
δ(ppm): 1.32 (6H, s), 3.18 (2H, d), 4.72 (1H, s), 6.57 (1H, s), 7.54 (1H, s)

REFERENCE EXAMPLE 8

3,4-Dihydro-2,2-dimethyl-6-nitro-2H-1,4-benzoxazine
Physicochemical properties:

i) Melting point: 151°–153° C.
ii) Elemental analysis (for $C_{10}H_{12}N_2O_3$)

|  | C (%) | H (%) | N (%) |
| --- | --- | --- | --- |
| Calcd.: | 57.69 | 5.81 | 13.45 |
| Found: | 57.59 | 5.88 | 13.48 | iii) NMR spectrum ($CDCl_3$)
δ(ppm): 1.37 (6H, s), 3.15 (2H, d), 6.78 (1H, d), 7.50(1H, d), 7.59 (1H, dd)

REFERENCE EXAMPLE 9

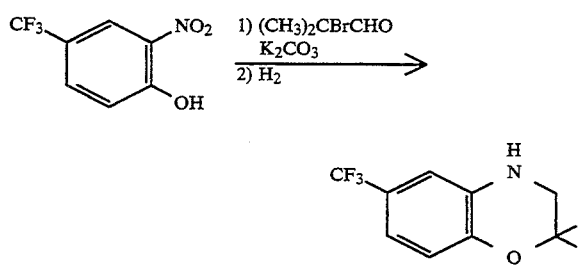

(1) To a mixture of 10 g of 2-nitro-4-trifluoromethylphenol, 8.0 g of anhydrous calcium carbonate and 30 ml of N,N-dimethylformamide was added dropwise a solution of 8.8 g of 2-bromoisobutyraldehyde in 23 ml of N,N-dimethylformamide and the mixture was stirred at room temperature for 4 days. The reaction mixture was then poured in ice-water and extracted with toluene. The organic layer was washed with 0.5 N aqueous sodium hydroxide solution and water in that order and dried over anhydrous magnesium sulfate and the solvent was distilled off. The residue was chromatographed on a silica gel column and elution was carried out with hexane-ethyl acetate (3:1). The Crystals from the eluate were recrystallized from 15 ml of hexane twice to give 4.428 g of 2-(2-nitro-4-trifluoromethylphenoxy)isobutyraldehyde.

(2) In 40 ml of ethanol was dissolved 4.408 g of the above aldehyde and after addition of a catalytic amount of Raney nickel, reduction was carried out in a hydrogen stream at atmospheric temperature and pressure. The catalyst was then filtered off and the solvent was distilled off. The residue was chromatographed on a silica gel column and elution was carried out with hexane-benzene (3:2) to recover 2.294 g of 3,4-dihydro-2,2-dimethyl-6-trifluoromethyl-2H-1,4-benzoxazine. A 1 g portion of this product was recrystallized from 2 ml of hexane to give 908 mg of a sample for elemental analysis.

This compound has the following physicochemical properties.

i) Melting point: 81°–82° C.
ii) Elemental analysis (for $C_{11}H_{12}F_3NO$)

|  | C (%) | H (%) | N (%) | F (%) |
| --- | --- | --- | --- | --- |
| Calcd.: | 57.14 | 5.23 | 6.06 | 24.65 |
| Found: | 57.10 | 5.31 | 6.00 | 24.62 | iii) NMR spectrum ($CDCl_3$)
δ(ppm): 1.35 (6H, s), 3.10 (2H, s); 3.3–4.4 (1H, broad s), 6.7–7.1 (3H, m)

EXAMPLE 1

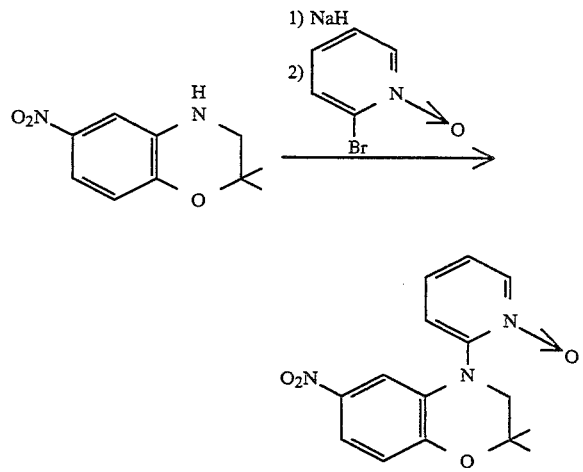

In 10 ml of N,N-dimethylformamide was dissolved 2.66 g of 3,4-dihydro-2,2-dimethyl-6-nitro-2H-1,4-benzoxazine followed by addition of 1.02 g of sodium hydride (60% in oil) and the mixture was stirred at room temperature for 30 minutes. Then, 2.77 g of 2-bromopyridine N-oxide hydrochloride was added with ice-cooling and, after the evolution of heat had subsided, the mixture was stirred at room temperature for 2 hours. The reaction mixture was then poured in water and extracted with ethyl acetate. The organic layer was separated and dried over anhydrous magnesium sulfate and filtered. The filtrate was concentrated under reduced pressure and the residue was chromatographed on a silica gel column using chloroform as the eluent to give crude 2-(3,4-dihydro-2,2-dimethyl-6-nitro-2H-1,4-benzoxazin-4-yl)pyridine N-oxide.

Recrystallization from chloroform-ethanol gave 2.0 g of the object compound.

Physicochemical properties:
i) Melting point: 224°–226° C.
ii) Elemental analysis (for $C_{15}H_{15}N_3O_4$)

|  | C (%) | H (%) | N (%) |
| --- | --- | --- | --- |
| Calcd.: | 59.80 | 5.02 | 13.95 |
| Found: | 59.73 | 5.20 | 13.80 | iii) NMR spectrum ($CDCl_3$)
δ(ppm): 1.42 (6H, s), 3.69 (2H, s), 6.94 (1H, d), 7.05–7.41 (3H,m), 7.49 (1H, d), 7.77 (1H, dd), 8.31 (1H, ddd)

EXAMPLE 2

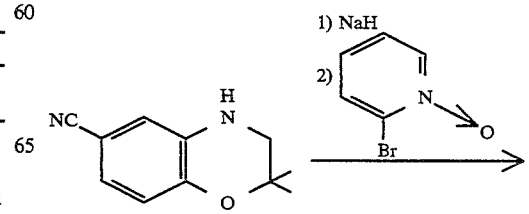

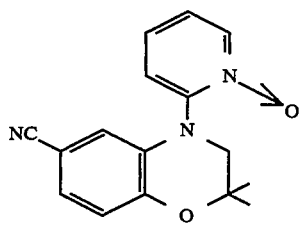

In 10 ml of N,N-dimethylformamide was dissolved 1.5 g of 6-cyano-3,4-dihydro-2,2-dimethyl-2H-1,4-benzoxazine and, then, 0.96 g of sodium hydride (60% in oil) was gradually added. After 10 minutes, 3.36 g of 2-bromopyridine N-oxide hydrochloride was added in several portions and after the evolution of heat had subsided, the mixture was stirred at room temperature for 3 hours. The reaction mixture was diluted with water and extracted with ethyl acetate. The organic layer was separated, dried over anhydrous magnesium sulfate and filtered. The filtrate was concentrated under reduced pressure and the residue was chromatographed on a silica gel column using ethyl acetate-methanol (5:1) as the eluent to give crude 2-(6-cyano-3,4-dihydro-2,2-dimethyl-2H-1,4-benzoxazin-4-yl)pyridine N-oxide. Crystallization from ethyl acetate gave 0.78 g of crude crystals. Finally the crystals were recrystallized from ethanol to recover 0.6 g of the desired compound.

This compound has the following physicochemical properties.

i) Melting point: 175°–177° C.
ii) Elemental analysis (for $C_{16}H_{15}N_3O_2$)

|  | C (%) | H (%) | N (%) |
|---|---|---|---|
| Calcd.: | 68.31 | 5.37 | 14.94 |
| Found: | 68.20 | 5.38 | 14.88 | iii) NMR spectrum (CDCl$_3$)
δ(ppm): 1.40 (6H, s), 3.67 (2H, s), 6.86–7.33 (6H, m), 8.26–8.33 (1H, m)

EXAMPLE 3 THROUGH 32

The compounds listed in the following table were synthesized by Process 1 as in Examples 1 and 2. It should be understood that where the reaction did not proceed well at room temperature, the reaction was conducted at elevated temperature. As the base, not only sodium hydride but also triethylamine or potassium carbonate was used. That is, in Examples 13 through 27, and 32, the reactions were conducted at 100° C. to 120° C., or with heating under refluxing. As the base, triethylamine was used in Examples 13, 14, 17 through 21, and 28 through 31, and anhydrous potassium carbonate was used in Example 15, 16 and 22.

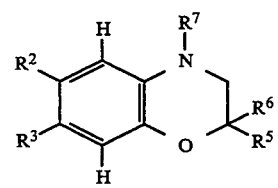

| Example No. | R$^2$ | R$^3$ | R$^5$ | R$^6$ | R$^7$ | Salt | Starting Compound (V) |
|---|---|---|---|---|---|---|---|
| 3 | PhSO$_2$ | H | CH$_3$ | CH$_3$ | (pyridine N-oxide) | free | (2-bromopyridine N-oxide) · HCl |
| 4 | NO$_2$ | H | H | H | (pyridine N-oxide) | free | (2-bromopyridine N-oxide) · HCl |
| 5 | Br | H | CH$_3$ | CH$_3$ | (pyridine N-oxide) | free | (2-bromopyridine N-oxide) · HCl |
| 6 | NO$_2$ | H | CH$_3$ | CH$_3$ | (3-methylpyridine N-oxide) | free | (2-chloro-3-methylpyridine N-oxide) · HCl |

-continued

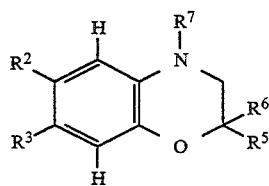

| Example No. | R² | R³ | R⁵ | R⁶ | R⁷ | Salt | Starting Compound (V) |
|---|---|---|---|---|---|---|---|
| 7 | MeSO₂ | H | CH₃ | CH₃ | [2-pyridyl N-oxide] | free | [2-bromopyridine N-oxide·HCl] |
| 8 | Cl | NO₂ | CH₃ | CH₃ | [2-pyridyl N-oxide] | free | [2-bromopyridine N-oxide·HCl] |
| 9 | CF₃ | H | CH₃ | CH₃ | [2-pyridyl N-oxide] | HCl free | [2-bromopyridine N-oxide·HCl] |
| 10 | NO₂ | H | CH₃ | CH₃ | [2-quinolyl N-oxide] | free | [2-chloroquinoline N-oxide·HCl] |
| 11 | NO₂ | H | CH₃ | CH₃ | [3-(Me₂NOC)pyrazin-2-yl] | free | [3-chloro-2-(Me₂NOC)pyrazine] |
| 12 | NO₂ | H | CH₃ | CH₃ | [3,4,5-trichloro-6-methyl-2-pyridyl] | free | [2,3,4,5,6-pentachloropyridine] |
| 13 | CN | H | CH₃ | CH₃ | —CH₂—[3-pyridyl] | free | Cl—CH₂—[3-pyridyl]·HCl |
| 14 | NO₂ | H | CH₃ | CH₃ | —CH₂—[2-pyridyl] | HCl salt | Cl—CH₂—[2-pyridyl]·HCl |
| 15 | NO₂ | H | CH₃ | CH₃ | —CH₂—[3-fluorophenyl] | free | Br—CH₂—[3-fluorophenyl] |

-continued

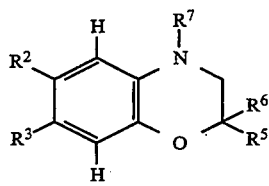

| Example No. | R² | R³ | R⁵ | R⁶ | R⁷ | Salt | Starting Compound (V) |
|---|---|---|---|---|---|---|---|
| 16 | NO₂ | H | CH₃ | CH₃ | —CH₂-(2-benzimidazolyl) | free | ClCH₂-(2-benzimidazolyl) |
| 17 | NO₂ | H | CH₃ | CH₃ | —CH₂-(2-nitrophenyl) | free | Br—CH₂-(2-nitrophenyl) |
| 18 | NO₂ | H | CH₃ | CH₃ | —CH₂-(3-nitrophenyl) | free | Br—CH₂-(3-nitrophenyl) |
| 19 | NO₂ | H | CH₃ | CH₃ | —CH₂-(3-pyridyl) | HCl salt | Cl—CH₂-(3-pyridyl)·HCl |
| 20 | NO₂ | H | CH₃ | CH₃ | —CH₂-phenyl | free | Cl—CH₂-phenyl |
| 21 | NO₂ | H | CH₃ | CH₃ | —CH₂-(4-nitrophenyl) | free | Br—CH₂-(4-nitrophenyl) |
| 22 | NO₂ | H | CH₃ | CH₃ | —CH₂-(2-fluorophenyl) | free | Br—CH₂-(2-fluorophenyl) |
| 23 | CN | H | CH₃ | CH₃ | —CH₂—N(phthalimidyl) | free | Br—CH₂—N(phthalimidyl) |
| 24 | NO₂ | H | CH₃ | CH₃ | —CH₂COOC₂H₅ | free | BrCH₂COOC₂H₅ |
| 25 | CN | H | CH₃ | CH₃ | —CH₂COOC₂H₅ | free | BrCH₂COOC₂H₅ |
| 26 | NO₂ | H | CH₃ | CH₃ | —CH(CH₃)COOC₂H₅ | free | Br—CH(CH₃)COOC₂H₅ |
| 27 | NO₂ | H | CH₃ | CH₃ | —CH₂CH₂OCH=CH₂ | free | BrCH₂CH₂OCH=CH₂ |
| 28 | NO₂ | H | CH₃ | CH₃ | —CO-(3-pyridyl) | HCl salt | ClCO-(3-pyridyl)·HCl |

-continued

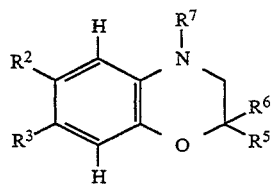

| Example No. | R² | R³ | R⁵ | R⁶ | R⁷ | Salt | Starting Compound (V) |
|---|---|---|---|---|---|---|---|
| 29 | NO₂ | H | CH₃ | CH₃ | —CO−(furan) | free | ClCO−(furan) |
| 30 | NO₂ | H | CH₃ | CH₃ | —COCH=CHCOOC₂H₅ | free *trans | ClCOCH=CHCOOC₂H₅ |
| 31 | NO₂ | H | CH₃ | CH₃ | —COCOOC₂H₅ | free | ClCOCOOC₂H₅ |
| 32 | CN | H | CH₃ | CH₃ | —(butyrolactone) | free | (bromo-butyrolactone) |

Physicochemical properties of these compounds are as follows.

EXAMPLE 3

2-(3,4-Dihydro-2,2-dimethyl-6-phenylsulfonyl-2H-1,4-benzoxazin-4-yl)pyridine N-oxide
Physicochemical properties:
i) Melting point: 123°–124° C.
ii) Elemental analysis (for $C_{21}H_{20}N_2O_4S$)

|  | C (%) | H (%) | N (%) | S (%) |
|---|---|---|---|---|
| Calcd.: | 63.62 | 5.08 | 7.07 | 8.09 |
| Found: | 63.42 | 5.09 | 7.05 | 8.09 | iii) NMR spectrum (CDCl₃)
δ(ppm): t.35 (6H, s), 3.69 (2H, t), 6.9–7.6 (9H, m), 7.8–7.9 (2H, m), 8.2–8.4 (1H, m)

EXAMPLE 4

2-(3,4-Dihydro-6-nitro-2H-1,4-benzoxazin-4-yl)pyridine N-oxide
Physicochemical properties:
i) Melting point: 139°–141° C.
ii) Elemental analysis (for $C_{13}H_{11}N_3O_4 \cdot 0.1H_2O$)

|  | C (%) | H (%) | N (%) |
|---|---|---|---|
| Calcd.: | 56.77 | 4.10 | 15.28 |
| Found: | 56.74 | 4.10 | 15.17 | iii) NMR spectrum (CDCl₃)
δ(ppm): 3.96 (2H, t), 4.44 (2H, t), 7.02 (1H, d), 7.2–7.4 (3H, m), .7.52 (1H, d), 7.78 (1H, dd), 8.36 (1H, d)

EXAMPLE 5

2-(6-Bromo-3,4-dihydro-2,2-dimethyl-2H-1,4-benzoxazin-4-yl)pyridine N-oxide
Physicochemical properties:
i) Melting point: 149°–151° C.
ii) Elemental analysis (for $C_{15}H_{15}N_2O_2Br$)

|  | C (%) | H (%) | N (%) | Br (%) |
|---|---|---|---|---|
| Calcd.: | 53.75 | 4.51 | 8.36 | 23.84 |
| Found: | 53.74 | 4.49 | 8.39 | 23.83 | iii) NMR spectrum (CDCl₃)
δ(ppm): 1.34 (6H, s), 3.65 (2H, s), (6H, m), 8.19–8.28 (1H, m)

EXAMPLE 6

2-(3,4-Dihydro-2,2-dimethyl-6-nitro-2H-1,4-benzoxazin-4-yl)-6-methylpyridine N-oxide
Physiochemical properties:
i) Melting point: 161°–163° C.
ii) Elemental analysis (for $C_{16}H_{17}N_3O_4$)

|  | C (%) | H (%) | N (%) |
|---|---|---|---|
| Calcd.: | 60.94 | 5.43 | 13.33 |
| Found: | 60.97 | 5.48 | 13.21 |

NMR spectrum (CDCl₃)
δ(ppm): 1.43 (6H, s), 2.5.7 (3H, s), 3.65 (2H, s), 6.89 (1H, d), 7.13–7.28 (3H, m), 7.40 (1H, d), 7.70 (1H, dd)

EXAMPLE 7

2-(3,4-Dihydro-2,2-dimethyl-6-methylsulfonyl-2H-1,4-benzoxazin-4-yl)pyridine N-oxide
Physicochemical properties:
i) Melting point: 220°–222° C.
ii) Elemental analysis (for $C_{16}H_{18}N_2O_4S$)

|  | C (%) | H (%) | N (%) | S (%) |
|---|---|---|---|---|
| Calcd.: | 57.47 | 5.43 | 8.38 | 9.59 |
| Found: | 57.51 | 5.49 | 8.30 | 9.59 | iii) NMR spectrum (CDCl₃)
δ(ppm): 1.38 (6H, s), 2.86 (3H, s)-, 3.65 (2H, s), 6.9–7.5 (6H, m), 8.2–8.3 (mH, m)

EXAMPLE 8

2-(6-Chloro-3,4-dihydro-2,2-dimethyl-7-nitro-2H-1,4-benzoxazin-4-yl)pyridine N-oxide
Physicochemical properties:
i) Melting point: 179°–180.5° C.
ii) Elemental analysis ( for $C_{15}H_{14}N_3O_4Cl$)

|         | C (%) | H (%) | N (%) | Cl (%) |
|---------|-------|-------|-------|--------|
| Calcd.: | 53.66 | 4.20  | 12.52 | 10.56  |
| Found:  | 53.58 | 4.25  | 12.39 | 10.61  | iii) NMR spectrum ($CDCl_3$)
δ(ppm): 1.40 (6H, s), 3.6.0 (2H, broad s), 6.46 (1H, s), 7.1–7.5 (3H, m), 7.60 (1H, s), 8.2–8.4 (1H, m)

EXAMPLE 9

2-(3,4-Dihydro-2,2-dimethyl-6-trifluoromethyl-2H-1,4-benzoxazin-4-yl)pyridine N-oxide hydrochloride
Physicochemical properties:
i) Melting point: 144°–166° C.
ii) Elemental analysis (for $C_{16}H_{15}N_2O_2F_3 \cdot HCl$)

|         | C (%) | H (%) | N (%) | Cl (%) | F (%) |
|---------|-------|-------|-------|--------|-------|
| Calcd.: | 53.27 | 4.47  | 7.77  | 9.83   | 15.80 |
| Found:  | 53.08 | 4.38  | 7.68  | 9.86   | 15.67 | iii) NMR spectrum ($CDCl_3$)
δ(ppm): 1.37 (6H, s), 3.97 (2H, s), 7.03 (1H, d), 7.2–7.5 (3H, m), 7.64 (1H, dd), 7.8–8.1 (1H, m), 8.76 (1H, dd), 11.85 (1H, broad s)

EXAMPLE 10

2-(3,4-Dihydro-2,2-dimethyl-6-nitro-2H-1,4-benzoxazin-4-yl)quinoline 1-oxide
Physicochemical properties:
i) Melting point: 183°–184° C.
ii) Elemental analysis (for $C_{19}H_{17}N_3O_4$)

|         | C (%) | H (%) | N (%) |
|---------|-------|-------|-------|
| Calcd.: | 64.95 | 4.88  | 11.96 |
| Found:  | 64.92 | 4.90  | 11.92 | iii) NMR spectrum ($CDCl_3$)
δ(ppm): 1.43 (6H, s), 3.84 (2H, s), 6.94 (1H, d), 7.24–7.90 (7H, m), 8.71 (1H, d of t)

EXAMPLE 11

3-(3,4-Dihydro-2,2-dimethyl-6-nitro-2H-1',4-benzoxazin-4-yl)-N,N-dimethylpyrazine-2-carboxamide
Physicochemical properties:
i) Melting point: 134°–135° C. (ethanol)
ii) Elemental analysis (for $C_{17}H_{19}N_5O_4$)

|         | C (%) | H (%) | N (%) |
|---------|-------|-------|-------|
| Calcd.: | 57.14 | 5.36  | 19.60 |
| Found:  | 57.19 | 5.47  | 19.52 | iii) NMR spectrum ($CDCl_3$)
δ(ppm): 1.48 (6H, s), 2.82 (3H, s), 3.19 (3H, s), 3.80 (2H, s), 6.95 (1H, d), 7.66 (1H, d), 7.84 (1H, dd), 8.26 (1H, d), 8.37 (1H, d)

EXAMPLE 12

3,4-Dihydro-2,2-dimethyl-6-nitro-4-(3,4,5,6-tetrachloro-2-pyridyl)-2H-1,4-benzoxazine
Physicochemical properties:
i) Melting point: 117°–119° C.
ii) Elemental analysis (for $C_{15}H_{11}N_3O_3Cl_4$)

|         | C (%) | H (%) | N (%) | Cl (%) |
|---------|-------|-------|-------|--------|
| Calcd.: | 42.58 | 2.62  | 9.93  | 33.52  |
| Found:  | 42.14 | 2.56  | 9.76  | 33.40  | iii) NMR spectrum ($CDCl_3$)
δ(ppm): 1.51 (6H, s), 3.49 (2H, s), 6.92–7.04 (2H, m), 7.77 (1H, dd)

EXAMPLE 13

3-(6-Cyano-3,4-dihydro-2,2-dimethyl-2H-1,4-benzoxazin-4-yl )methylpyridine
Physicochemical properties:
i) Melting point: 107°–108° C. (ethanol-hexane)
ii ) Elemental analysis (for $C_{17}H_{17}N_3O$).

|         | C (%) | H (%) | N (%) |
|---------|-------|-------|-------|
| Calcd.: | 73.10 | 6.13  | 15.04 |
| Found:  | 73.01 | 6.19  | 15.02 | iii) NMR spectrum ($CDCl_3$)
δ(ppm): 1.35 (6H, s), 3.07 (2H, s), 4.46 (2H, s), 6.74–7.04 (3H, m), 7.20–7.33 (1H, m), 7.51–7.65 (1H, m), 8.50–8.58 (2H, m)

EXAMPLE 14

3,4-Dihydro-2,2-dimethyl-6-nitro-4-(2-pyridylmethyl)-H-1,4-benzoxazine hydrochloride
Physicochemical properties:
i) Melting point: 174°–178° C. (ethanol)
ii) Elemental analysis (for $C_{16}H_{17}N_3O_3 \cdot HCl$)

|         | C (%) | H (%) | N (%) | Cl (%) |
|---------|-------|-------|-------|--------|
| Calcd.: | 57.23 | 5.40  | 12.51 | 10.56  |
| Found:  | 57.36 | 5.39  | 12.59 | 10.77  | iii) NMR spectrum (DMSO-$d_6$)
δ(ppm): 1.34 (6H, s), 3.37 (2H, s), 5.04 (2H, s), 6.84–6.96 (1H, m), 7.48–7.61 (2H, m), 7.72–7.91 (2H, m), 8.37 (1H, d of t), 8.80–8.90 (1H, m)

EXAMPLE 15

4-(3-Fluorobenzyl)-3,4-dihydro-2,2-dimethyl-6-nitro-2H-1,4-benzoxazine
Physicochemical properties:
i) Melting point: 68°–69° C. (ethanol)
ii) Elemental analysis (for $C_{17}H_{17}N_2O_3F$)

|         | C (%) | H (%) | N (%) | F (%) |
|---------|-------|-------|-------|-------|
| Calcd.: | 64.55 | 5.42  | 8.86  | 6.01  |
| Found:  | 64.68 | 5.43  | 8.78  | 6.08  | iii) NMR spectrum ($CDCl_3$)
δ(ppm): 1.38 (6H, s), 3.11 (2H, s), 4.52 (2H, s), 6.7–7.7 (7H, m)

EXAMPLE 16

4-(2-Benzimidazolylmethyl)-3,4-dihydro-2,2-dimethyl-2H-nitro-2H-1,4-benzoxazine
Physicochemical properties:
i) Melting point: 213°–214° C.
ii) Elemental analysis (for $C_{18}H_{18}N_4O_3$)

|        | C (%) | H (%) | N (%) |
|--------|-------|-------|-------|
| Calcd.:| 63.89 | 5.36  | 16.56 |
| Found: | 63.87 | 5.39  | 16.55 | iii) Mass spectrum (EI): m/z 338 (M+)

EXAMPLE 17

3,4-Dihydro-2,2-dimethyl-6-nitro-4-(2-nitrobenzyl)-2H-1,4-benzoxazine
Physicochemical properties:
i) Melting point: 116°–118° C.
ii) Elemental analysis (for $C_{17}H_{17}N_3O_5$)

|        | C (%) | H (%) | N (%) |
|--------|-------|-------|-------|
| Calcd.:| 59.47 | 4.99  | 12.24 |
| Found: | 59.31 | 4.98  | 12.26 | iii) NMR spectrum ($CDCl_3$)
δ(ppm): 1.39 (6H, s), 3.18 (2H, s), 4.93 (2H, s), 6.90 (1H, d), 7.4–7.7 (5H, m), 8.1–8.2 (1H, m)

EXAMPLE 18

3,4-Dihydro-2,2-dimethyl-6-nitro-4-(3-nitrobenzyl)-2H-1,4-benzoxazine
Physicochemical properties:
i) Melting point: 125°–127° C.
ii) Elemental analysis (for $C_{17}H_{17}N_3O_5 \cdot 0.1H_2O$)

|        | C (%) | H (%) | N (%) |
|--------|-------|-------|-------|
| Calcd.:| 59.16 | 5.02  | 12.17 |
| Found: | 59.04 | 4.93  | 12.10 | iii) NMR spectrum ($CDCl_3$)
δ(ppm): 1.20 (6H, s), 3.12 (2H, s), 4.60 (2H, s), 6.81 (1H, d), 7.4–7.7 (4H, m), 8.0–8.2 (2H, m)

EXAMPLE 19

3-(3,4-Dihydro-2,2-dimethyl-6-nitro-2H-1,4-benzoxazin-4-yl)methylpyridine hydrochloride
Physicochemical properties:
i) Melting point: 186°–189° C.
ii) Elemental, analysis (for $C_{16}H_{18}N_3O_3Cl$)

|        | C (%) | H (%) | N (%) | Cl (%) |
|--------|-------|-------|-------|--------|
| Calcd.:| 57.23 | 5.40  | 12.51 | 10.56  |
| Found: | 57.21 | 5.26  | 12.70 | 10.78  | iii) NMR spectrum (DMSO-$d_6$)
δ(ppm): 1.33 (6H, s), 3.29 (2H, s), 4.84 (2H, s), 6.84–6.93 (1H, m), 7.48–7.59 (2H, m), 7.91–8.06 (1H, m), 8.36–8.50 (1H, m), 8.77–8.89 (2H, m)

EXAMPLE 20

4-Benzyl-3,4-dihydro-2,2-dimethyl-6-nitro-2H-1,4-benzoxazine
Physicochemical properties:
i) Melting point: 92°–93° C.
ii) Elemental analysis (for $C_{17}H_{18}N_2O_3$)

|        | C (%) | H (%) | N (%) |
|--------|-------|-------|-------|
| Calcd.:| 68.44 | 6.08  | 9.39  |
| Found: | 68.57 | 6.13  | 9.30  | iii) NMR spectrum ($CDCl_3$)
δ(ppm): 1.36 (6H, s), 3.06 (2H, s), 4.28 (2H, s), 6.78 (1H, d), 7.2–7.4 (5H, m), 7.5–7.7 (2H, m)

EXAMPLE 21

3,4-Dihydro-2,2-dimethyl-6-nitro-4-(4-nitrobenzyl)-2H-1,4-benzoxazine
Physicochemical properties:
i) Melting point: 118°–119° C.
ii) Elemental analysis (for $C_{17}H_{17}N_3O_5$)

|        | C (%) | H (%) | N (%) |
|--------|-------|-------|-------|
| Calcd.:| 59.47 | 4.99  | 12.24 |
| Found: | 59.47 | 4.90  | 12.32 | iii) NMR spectrum ($CDCl_3$)
δ(ppm): 1.39 (6H, s), 3.13 (2H, s), 4.61 (2H, s), 6.82 (1H, d), 7.40–7.67 (4s, m), 8.13–8.28 (2H, m)

EXAMPLE 22

4-(2-Fluorobenzyl)-3,4-dihydro-2,2-dimethyl-6-nitro-2H-1,4-benzoxazine
Physicochemical properties:
i) Melting point: oil
ii) NMR spectrum ($CDCl_3$)
δ(ppm): 1.32 (6H, s), 3.11 (2H, s), 4.54 (2H, s), 6.77 (1H, dd), 6.9–7.4 (4H, m), 7.5–7.7 (2H, m)
iii) Mass spectrum (FAB) : m/z 316 (M+)

EXAMPLE 23

6-Cyano-3,4-dihydro-2,2-dimethyl-4-(phthalimidomethyl)-2H-1,4-benzoxazine
Physicochemical properties:
i) Melting point: 147°–148° C.
ii) Elemental analysis (for $C_{20}H_{17}N_3O_3$)

|        | C (%) | H (%) | N (%) |
|--------|-------|-------|-------|
| Calcd.:| 69.15 | 4.93  | 12.10 |
| Found: | 69.21 | 4.96  | 12.06 | iii) NMR spectrum ($CDCl_3$)
δ(ppm): 1.32 (6H, s), 3.44 (2H, 5.23 (2H, s), 6.76 (1H, d), 7.01 (1H, dd), 7.67–7.96 (5H, m)

EXAMPLE 24

Ethyl (3,4,dihydro-2,2-dimethyl-6-nitro-2H-1,4-benzoxazin-4-yl)acetate
Physicochemical properties:
i) Melting point: 95°–96° C. (ethyl acetate-n-hexane)
ii) Elemental analysis (for $C_{14}H_{18}N_2O_5$)

|        | C (%) | H (%) | N (%) |
|--------|-------|-------|-------|
| Calcd.:| 57.14 | 6.16  | 9.52  |
| Found: | 57.16 | 6.15  | 9.43  | iii) NMR spectrum ($CDCl_3$)

δ(ppm): 1.27 (3H, t), 1.36 (6H, s), 3.21 (2H, s), 4.10 (2H, s), 4.20 (2H, q), 6.77 (1H, d), 7.37 (1H, d), 7.59 (1H, dd)

EXAMPLE 25

Ethyl (6-cyano-3,4-dihydro-2,2-dimethyl-2H-1,4-benzoxazin-4-yl)acetate
Physicochemical properties:
i) Melting point: 52°–53° C.
ii) Elemental analysis (for $C_{15}H_{18}N_2O_3$)

|  | C (%) | H (%) | N (%) |
|---|---|---|---|
| Calcd.: | 65.68 | 6.61 | 10.21 |
| Found: | 65.81 | 6.65 | 10.20 | iii) NMR spectrum (CDCl$_3$)
δ(ppm): 1.28 (3H, t), 1.36 (6H, s), 3.20 (2H, s), 4.01 (2H, s), 4.20 (2H, q), 6.67 (1H, d), 6.75 (1H, d), 6.95 (1H, dd)

EXAMPLE 26

Ethyl 2-(3,4-dihydro-2,2-dimethyl-6-nitro-2H-1,4-benzoxazin-4-yl)propionate
Physicochemical properties:
i) Melting point: 77°–78° C.
ii) Elemental analysis (for $C_{15}H_{20}N_2O_5$)

|  | C (%) | H (%) | N (%) |
|---|---|---|---|
| Calcd.: | 58.43 | 6.54 | 9.09 |
| Found: | 58.41 | 6.47 | 9.13 | iii) NMR spectrum (CDCl$_3$)
δ(ppm): 1.15–1.75 (12H, m), 3.15 (2H, s), 4.20 (2H, q), 4.57 (1H, q), 6.80 (1H, dd), 7.50–7.75 (2H, m)

EXAMPLE 27

3,4-Dihydro-2,2-dimethyl-6-nitro-4-(2-vinyloxyethyl)-H-1,4-benzoxazine
Physicochemical properties:
i) Melting point: 56°–56.5° C.
ii) Elemental analysis (for $C_{15}H_{20}N_2O_4$)

|  | C (%) | H (%) | N (%) |
|---|---|---|---|
| Calcd.: | 60.42 | 6.52 | 10.07 |
| Found: | 60.37 | 6.44 | 10.00 | iii) NMR spectrum (CDCl$_3$)
δ(ppm): 1.35 (6H, s), 3.23 (2H, s), 3.68 (2H, t), 3.93 (2H, s), 4.q5 (1H, dd), 4.21 (1H, dd), 6.47 (1H, dd), 6.80 (1H, d), 7.47–7.84 (2H, m)

EXAMPLE 28

3,4-Dihydro-2,2-dimethyl-4-nicotinoyl-6-nitro-2H-1,4-benzoxazine hydrochloride
Physicochemical properties:
i) Melting point: 158°–199° C. (ethanol)
ii) Elemental analysis (for $C_{16}H_{15}N_3O_4 \cdot HCl$)

|  | C (%) | H (%) | N (%) | Cl (%) |
|---|---|---|---|---|
| Calcd.: | 54.94 | 4.61 | 12.01 | 10.14 |
| Found: | 55.01 | 4.64 | 12.04 | 10.16 | iii) NMR spectrum (DMSO-d$_6$)
δ(ppm): 1.28 (6H, s), 3.75 (2H, s), 7.13 (1H, d), 7.8–8.1 (2H, m), 8.4–8.8 (2H, m), 8.9–9.2 (2H, m), 11.1 (1H, broad s)

EXAMPLE 29

4-(2-Furoyl)-3,4-dihydro-2,2-dimethyl-6-nitro-2H-1,4-benzoxazine
Physicochemical properties:
i) Melting point: 112°–116.5° C. (ethanol)
ii) Elemental analysis (for $C_{15}H_{14}N_2O_5$)

|  | C (%) | H (%) | N (%) |
|---|---|---|---|
| Calcd.: | 59.60 | 4.67 | 9.27 |
| Found: | 59.56 | 4.62 | 9.31 | iii) NMR spectrum (CDCl$_3$)
δ(ppm): 2.42 (6H, s), 3.84 (2H, s), 6.53 (1H, dd), 6.94 (1H, d), 7.16 (1H, dd), 7.45 (1H, dd), 7.91 (1H, dd), 8.13 (1H, d)

EXAMPLE 30

Ethyl trans-4-(3,4-dihydro-2,2-dimethyl-6-nitro-2H-1,4-benzoxazine-4-yl)-4-oxo-2-butenoate
Physicochemical properties:
i) Melting point: 93°–95° C.
ii) Elemental analysis (for $C_{16}H_{18}N_2O_6$)

|  | C (%) | H (%) | N (%) |
|---|---|---|---|
| Calcd.: | 57.48 | 5.43 | 8.38 |
| Found: | 57.30 | 5.41 | 8.19 | iii) NMR spectrum (DMSO-d$_6$)
δ(ppm): 1.24 (3H, t), 1.32 (6H, s), 3.86 (2H, s), 4.21 (2H, q), 6.74 (1H, d), 7.08 (1H, d), 7.56 (1H, d), 7.97 (1H, dd), 8.5–8.0 (1H, broad s)

EXAMPLE 31

3,4-Dihydro-2,2-dimethyl-6-nitro-4-ethyloxalyl-2H-1,4-benzoxazine
Physicochemical properties:
i) Melting point: 80°–81° C.
ii) Elemental analysis (for $C_{14}H_{16}N_2O_6$)

|  | C (%) | H (%) | N (%) |
|---|---|---|---|
| Calcd.: | 54.54 | 5.23 | 9.09 |
| Found: | 54.51 | 5.19 | 9.05 | iii) NMR spectrum (CDCl$_3$)
δ(ppm): 1.37–1.41 (3H, m), 1.42 (3H, 1.45 (3H, s), 3.57 (2H x 2/5, s), 3.83 (2H ,x 3/5, s), 4.36–4.46 (2H, m), 6.99 (1H, d), 8.02 (1H, m), 9.11 (1H, broad s)

EXAMPLE 32

6-Cyano-3,4-dihydro-2,2-dimethyl-4-(2-oxo-3-oxolanyl)-2H-1,4-benzoxazine
Physicochemical properties:
i) Melting point: 144°–146° C. (ethanol)
ii) Elemental analysis (for $C_{15}H_{16}N_2O_3$)

|  | C (%) | H (%) | N (%) |
|---|---|---|---|
| Calcd.: | 66.16 | 5.92 | 10.29 |
| Found: | 66.03 | 5.93 | 10.21 | iii) NMR spectrum (CDCl$_3$)

δ(ppm): 1.38 (3H, s), 1.41 (3H, s), 2.2–2.7 (2H, m), 2.99 (2H, d), 4.2–4.8 (3H, m), 6.82 (1H, d), 6.89 (1H, d), 7.05 (1H, dd)

EXAMPLE 33

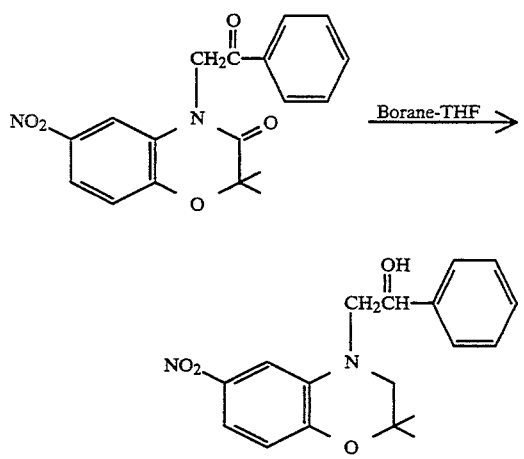

In an argon gas stream, 1.5 g of 3,4-dihydro-2,2-dimethyl-6-nitro-3-oxo-4-phenacyl-2H-1,4-benzoxazine was added to 30 ml of a 1.0 M solution of borane in tetrahydrofuran at 0°–10° C. The above solution was stirred at 70° C. for 1 hour, at the end of which time 5.6 ml of methanol was gradually added. After stirring at 70° C. for 15 minutes, 5.6 ml of concentrated hydrochloric acid was added and the mixture was further stirred at 70° C. for 1 hour. The solvent was then distilled off and the residue was diluted with 30 ml of water, made alkaline with potassium carbonate, and extracted with ethyl acetate. The extract was dried over anhydrous magnesium sulfate and the solvent was distilled off. The residue was purified by silica gel column chromatography (eluent: ethyl acetate-n-hexane) to give 1.67 g of 3,4-dihydro-4-(2-hydroxy-2-phenylethyl)-2,2-dimethyl-6-nitro-2H-1,4-benzoxazine as oil.

Mass spectrum (EI): m/z 328 (M+)

EXAMPLE 34

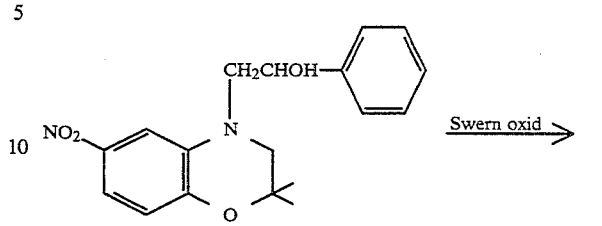

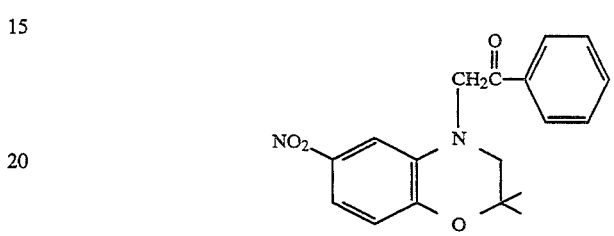

In an argon gas stream, 0.7 ml of dry dimethyl sulfoxide was added gradually to a solution of 0.41 ml of oxalyl chloride in 10 ml of dry methylene chloride previously cooled from −50° to −60° C. and the mixture was stirred at the same temperature for 2 minutes.

Then, 20 ml of a solution of 1.5 g of 3,4-dihydro-4-(2-hydroxy-2-phenylethyl)-2,2-dimethyl-6-nitro-2H-1,4-benzoxazine in dry methylene chloride was added over a period of 5 minutes and the mixture was stirred at the same temperature as above for 15 minutes.

To this reaction mixture was added 1.3 ml of triethylamine and, at room temperature, the mixture was diluted with 30 ml of water and extracted with methylene chloride. The extract was dried over anhydrous magnesium sulfate and the solvent was distilled off. The residue was recrystallized from ether to give 1.31 g of 3,4-dihydro-2,2-dimethyl-6-nitro-4-phenacyl-2H-1,4-benzoxazine melting at 125°–128° C.

Physicochemical properties:

Elemental analysis (for $C_{18}H_{18}N_2O_4$)

|  | C (%) | H (%) | N (%) |
| --- | --- | --- | --- |
| Calcd.: | 66.25 | 5.56 | 8.58 |
| Found: | 66.16 | 5.62 | 8.47 |

Mass spectrum (EI) : m/z 326 (M+)

EXAMPLE 35–40

The compounds listed in the following table were synthesized by Process 2 as in Examples 33 and 34.

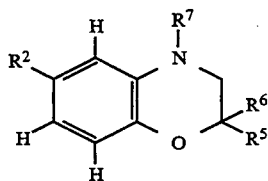

| Example No. | R² | R⁵ | R⁶ | R⁷ | Starting Compound |
|---|---|---|---|---|---|
| 35 | NO₂ | CH₃ | CH₃ | —CH₂—CH(OH)-(2-pyridyl) | (2-pyridyl-CO-CH₂)-N-aryl compound |
| 36 | NO₂ | CH₃ | CH₃ | —CH₂—CH(OH)—CH₃ | CH₃-CO-CH₂-N-aryl compound |
| 37 | NO₂ | CH₃ | CH₃ | —CH₂—C(O)-(2-pyridyl) | The compound of Example 35 |
| 38 | NO₂ | CH₃ | CH₃ | —CH₂—C(O)—CH₃ | The compound of Example 36 |
| 39 | NO₂ | CH₃ | CH₃ | 2-methylcyclopentanol | cyclopentanone-N-aryl compound |
| 40 | NO₂ | CH₃ | CH₃ | 2-methylcyclopentanone | The compound of Example 39 |

These compounds have the following physicochemical properties.

EXAMPLE 35

3,4-Dihydro-4-[2-hydroxy-2-(2-pyridyl)ethyl]-2,2-dimethyl-6-nitro-2H-1,4-benzoxazine Mass spectrum(EI) : m/z 329 (M+)

EXAMPLE 36

3,4-Dihydro-4-(2-hydroxypropyl)-2,2-dimethyl-6-nitro-2H-1,4-benzoxazine

Mass spectrum (EI) : m/z 266 (M+)

EXAMPLE 37

3,4-Dihydro-2,2-dimethyl-6-nitro-4-[(2-pyridylcarbonyl)methyl]-2H-1,4-benzoxazine Melting point: 106°–107° C.

Elemental analysis ( for C₁₇H₁₇N₃O₄)

|  | C (%) | H (%) | N (%) |
|---|---|---|---|
| Calcd.: | 62.38 | 5.23 | 12.84 |
| Found: | 62.38 | 5.23 | 12.76 |

Mass spectrum (GC-MS) : m/z 327 (M+)

EXAMPLE 38

4-Acetonyl-3,4-dihydro-2,2-dimethyl-6-nitro-2H-1,4-benzoxazine

Melting point: 98°–99° C.

Elemental analysis (for C₁₃H₁₆N₂O₄)

|  | C (%) | H (%) | N (%) |
|---|---|---|---|
| Calcd.: | 59.08 | 6.10 | 10.60 |
| Found: | 58.92 | 6.21 | 10.52 |

Mass spectrum (GC-MS) : m/z 264 (M+)

EXAMPLE 39

3,4-Dihydro-2,2-dimethyl-4-(2-hydroxycyclopentyl)-6-nitro-2H-1,4-benzoxazine
Physicochemical properties:
i) Elemental, analysis (for $C_{15}H_{20}N_2O_4$)

|         | C (%) | H (%) | N (%) |
|---------|-------|-------|-------|
| Calcd.: | 61.63 | 6.90  | 9.58  |
| Found:  | 61.60 | 7.00  | 9.53  | ii) Melting point: 87°–88° C. (n-hexane)
iii) Mass spectrum (m/z): 292 (M+) (EI)
iv) NMR spectrum (CDCl$_3$)
δ(ppm): 1.32 (3H, s), 1.39 (3H, s), 1.58–2.22 (6Hr m), 3.26 (2H, s), 3.80 (1H, m), 4.50–4.68 (1H, m), 6.79 (1H, d), 7.59 (1H, d), 7.60 (1H, dd)

EXAMPLE 40

3,4-Dihydro-2,2-dimethyl-6-nitro-4-(2-oxocyclopentyl)-2H-1,4-benzoxazine
Physicochemical properties:
i) Elemental analysis (for $C_{15}H_{18}N_2O_4$)

|         | C (%) | H (%) | N (%) |
|---------|-------|-------|-------|
| Calcd.: | 62.06 | 6.25  | 9.65  |
| Found:  | 61.84 | 6.38  | 9.52  | ii) Melting point: 118°–119° C. (ether-n-hexane)
iii) Mass spectrum (m/z): 290 (M+) (EI)
iv) NMR spectrum (CDCl$_3$)
δ(ppm): 1.34 (3H, s), 1.41 (3H, s), 1.75–2.60 (6H, m), 2.83(1H, d), 2.99 (1H, d), 4.22–4.44 (1H, m), 6.79 (1H, d), 7.51 (1H, d), 7.61 (1H, dd)

EXAMPLE 41

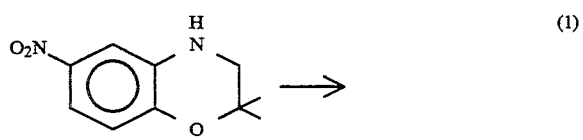

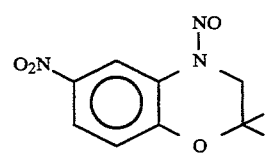

(1) In a mixture of 34 ml of methanol and 2.07 ml of acetic acid was dissolved 3 g of 3,4-dihydro-2,2-dimethyl-6-nitro-2H-1,4-benzoxazine. Then, a solution of 2.0 g of sodium nitrite in 6.6 ml of water was added dropwise and the mixture was stirred at room temperature overnight. The reaction mixture was neutralized with aqueous sodium hydroxide solution, concentrated under reduced pressure and extracted with chloroform. The organic layer was washed with saturated aqueous sodium chloride solution, dried over anhydrous magnesium sulfate and filtered. The filtrate was concentrated under reduced pressure to give 3.2 g of 3,4-dihydro-2,2-dimethyl-6-nitro-4-nitroso-2H-1,4-benzoxazine.

This compound has the following physicochemical properties.

i) Melting point: 104°–105° C.
ii) Elemental analysis (for $C_{10}H_{11}N_3O_4$)

|         | C (%) | H (%) | N (%) |
|---------|-------|-------|-------|
| Calcd.: | 50.63 | 4.67  | 17.71 |
| Found:  | 50.36 | 4.63  | 17.71 | iii) NMR spectrum (CDCl$_3$)
67 (ppm): 1.37 (6H, s), 3.87 (2H, s), 7.06 (1H, d), 8.08 (1H, dd), 8.90 (1H, d)

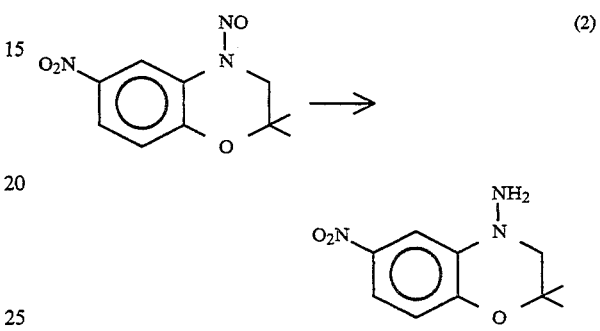

(2) In 69 ml of methanol was dissolved 2.29 g of 3,4-dihydro-2,2-dimethyl-6-nitro-4-nitroso-2H-1,4-benzoxazine and the solution was cooled on an ice bath. After addition of a solution of 1.16 g of sodium hydroxide in 8.1 ml of water to the above solution, 3.13 g of formamidinosulfinic acid was gradually added. The mixture was stirred at room temperature overnight and, then, concentrated. The concentrate was subjected to column chromatography (eluent: hexane;ethyl acetate=9:1) to give 0.4 g of 4-amino-3,4-dihydro-2,2-dimethyl-6-nitro-2H-1,4-benzoxazine.

Recrystallization from ether-hexane gave 0.28 g of the object compound.

This compound has the following physicochemical properties.

i) Melting point: 83°–85° C.
ii) Elemental analysis (for $C_{10}H_{13}N_3O_3$)

|         | C (%) | H (%) | N (%) |
|---------|-------|-------|-------|
| Calcd.: | 53.81 | 5.87  | 18.82 |
| Found:  | 53.75 | 5.80  | 18.93 | iii) NMR spectrum (CDCl$_3$)
δ(ppm): 1.41 (6H, s), 3.18 (2H, s), 6.77 (1H, d), 7.66 (1H, dd), 8..06 (1H, d)

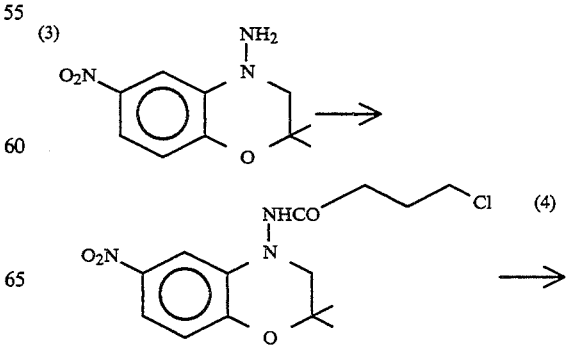

-continued

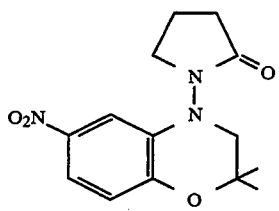

(3) In 4 ml of methylene chloride was dissolved 0.35 g of 4-amino-3,4-dihydro-2,2-dimethyl-6-nitro-2H-1,4-benzoxazine and the solution was cooled on an ice bath. To this solution was added 0.16 g of triethylamine followed by dropwise addition of a solution of 0.18 ml of 4-chlorobutyryl chloride in 1.4 ml of methylene chloride. After 30 minutes, the reaction mixture was diluted with water and extracted with chloroform. The organic layer was dried over anhydrous magnesium sulfate and concentrated under reduced pressure. The concentrate was crystallized from ether to give 0.43 g of crude crystals of 4-chloro-N-(3,4-dihydro-2,2-dimethyl-6-nitro- 2H-1,4-benzoxazin-4-yl)butyrylamide. The crude crystals were used without purification in the next reaction. (4) In 8 ml of N,N-dimethylformamide was dissolved 0.41 g of the above amide and the solution was cooled on an ice bath. Then, 0.14 g of potassium tert-butoxide was gradually added. The mixture was stirred with ice-cooling for 1 hour, after which it was diluted with water and extracted with ethyl acetate. The organic layer was washed with saturated aqueous sodium chloride solution, dried over anhydrous magnesium sulfate and filtered. The filtrate was concentrated under reduced pressure and crystallized from ether. The crude crystals were recrystallized from ethanol to give 0.16 g of 3,4-dihydro-2,2-dimethyl-4-(2-oxo-1-pyrrolidinyl)-6-nitro-2H-1,4-benzoxazine.

This compound has the following physicochemical properties.

i) Melting point: 141°–143° ii) Elemental analysis (for $C_{14}H_{17}N_3O_4$)

|  | C (%) | H (%) | N (%) |
|---|---|---|---|
| Calcd.: | 57.72 | 5.88 | 14.42 |
| Found: | 57.61 | 5.89 | 14.40 | iii) NMR spectrum (CDCl$_3$)

δ(ppm): 1.41 (3H, s), 1.49 (3H, s), 2.1–2.7 (4H, m), 3.15 (1H, d), 3.4–3.8 (3H, m), 6.84 (1H, d), 7.46 (1H, d), 7.70 (1H, dd)

EXAMPLE 42–44

The following compounds were synthesized by Process 3 as in Example 41.

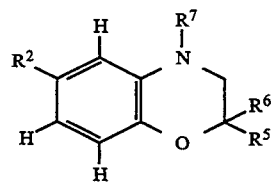

| Example No. | R² | R³ | R⁴ | R⁷ | Starting Compound |
|---|---|---|---|---|---|
| 42 | CN | CH₃ | CH₃ | (pyrrolidinone) | NC-aryl-NHCOCH₂CH₂CH₂Cl |
| 43 | Br | CH₃ | CH₃ | —NHCOCH₃ | Br-aryl-NH₂ |
| 44 | H | CH₃ | CH₃ | (pyrrolidinone) | aryl-NHCOCH₂CH₂CH₂Cl |

These compounds have the following physicochemical properties.

EXAMPLE 42

6-Cyano-3,4-dihydro-2,2-dimethyl-4-(2-oxo-1-pyrrolidinyl)-2H-1,4-benzoxazine i) Melting point: 149°–150° C.

ii) Elemental analysis (for $C_{15}H_{17}N_3O_2$)

|  | C (%) | H (%) | N (%) |
|---|---|---|---|
| Calcd.: | 66.40 | 6.32 | 15.49 |
| Found: | 66.29 | 6.08 | 15.51 | iii) NMR spectrum (CDCl$_3$)

δ(ppm): 1.38 (3H, s), 1,45 (3H, s), 2.1–2.6 (4H, m), 3.11 (1H, d), 3.4–3.7 (3H, m), 6.74–6.84 (2H, m), 7.04 (1H, dd)

EXAMPLE 43

N-(6-Bromo-3,4-dihydro-2,2-dimethyl-2H-1,4-benzoxazin-4-yl)acetamide i) Melting point: 167°–168° C.
ii) Elemental analysis (for $C_{12}H_{15}N_2O_2Br$)

|  | C (%) | H (%) | N (%) | Br (%) |
|---|---|---|---|---|
| Calcd.: | 48.18 | 5.05 | 9.36 | 26.71 |
| Found: | 48.14 | 5.01 | 9.29 | 26.51 | iii) NMR spectrum (CDCl₃)

δ(ppm): 1.36–1.45 (6H, m), 2.06, 2.12 (3H, s x2), 3.16, 3.30 (2H, s x 2), 6.56–6.97 (3H, m)

EXAMPLE 44

3,4-Dihydro-2,2-dimethyl-4-(2-oxo-1-pyrrodinyl)-2H-1,4-benzoxazine i) Melting point: 139°–141° C.
ii) Elemental analysis (for $C_{14}H_{18}N_2O_2$)

|  | C (%) | H (%) | N (%) |
|---|---|---|---|
| Calcd.: | 68.27 | 7.37 | 11.37 |
| Found: | 67.75 | 7.44 | 11.26 | iii) NMR spectrum (CDCl₃)

δ(ppm): 1.38 (3H, s), 1.46 (3H, s), 2.04–2.58 (4H, m), 3.0–3.6 (4H, m), 6.51–6.84 (4H, m)

EXAMPLE 45

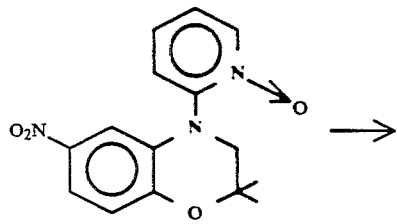

→

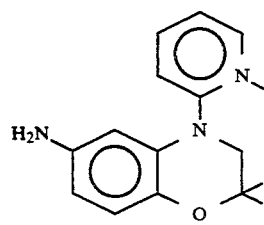

To a solution of 3.01 g of 2-(3,4-dihydro-2′,2-dimethyl-6-nitro-1,4-benzoxazin-4-yl)pyridine N-oxide in 50 ml of methanol was added an aqueous solution of 10.9 g of ammonium chloride (50 ml) at room temperature. Then, with ice-cooling, 13.1 g of zinc dust was added and the mixture was stirred at 3° C. for 15 hours. The insolubles were filtered off and the filtrate was concentrated, diluted with water and extracted with chloroform. The organic layer was dried and the solvent was distilled off. The residue was chromatographed on a silica gel column and elution was carried out with chloroform-methanol (50:1). The eluate gave 1.86 g of 2-(6-amino)-3,4-dihydro-2,2-dimethyl-2H-1,4-benzoxazin-4-yl)pyridine N-oxide. This compound has the following physicochemical properties.

i) Melting point: 200°–202° C.
ii) Elemental analysis (for $C_{15}H_{17}N_3O_2 \cdot 0.1H_2O$)

|  | C (%) | H (%) | N (%) |
|---|---|---|---|
| Calcd.: | 65.97 | 6.35 | 15.39 |
| Found: | 65.94 | 6.35 | 15.39 | iii) NMR spectrum (CDCl₃)

δ(ppm): 1.30 (6H, s), 3.28 (2H, broad s), 3.69 (2H, s), 6.19–7.49 (6H, m), 8.23 (1H, m)

EXAMPLE 46

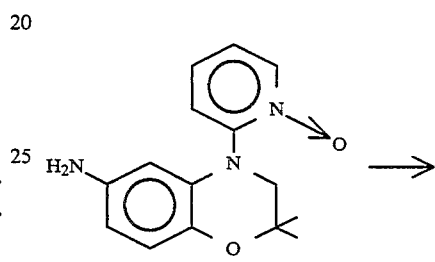

→

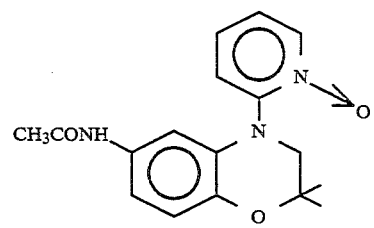

To a solution of 0.474 g of 2-(6-amino-3,4-dihydro-2,2-dimethyl-2H-1,4-benzoxazin-4-yl)pyridine N-oxide in 5 ml of acetic anhydride was added 3 drops of pyridine and the mixture was stirred at room temperature for 63 hours. After concentration, the residue was dissolved in chloroform, washed with saturated aqueous sodium hydrogen carbonate solution, dried and concentrated. The residue was recrystallized from chloroform-ether to give 0.285 g of 2-(6-acetamido-3,4-dihydro-2,2-dimethyl-2H-1,4-benzoxazin-4-yl)pyridine N-oxide.

This compound has the following physicochemical properties.

i) Melting point: 290°–295° C. (decompn.)
ii) Elemental, analysis (for $C_{17}H_{19}N_3O_3 \cdot 0.1H_2O$)

|  | C (%) | H (%) | N (%) |
|---|---|---|---|
| Calcd.: | 64.79 | 6.14 | 13.33 |
| Found: | 64.74 | 6.18 | 13.20 | iii) NMR spectrum (CDCl₃)

δ(ppm): 1.30 (6H, s), 2.04 (3H, s), 3.65 (2H, s), 6.68–7.64 (6H, m), 8.18 (1H, m)

EXAMPLE 47

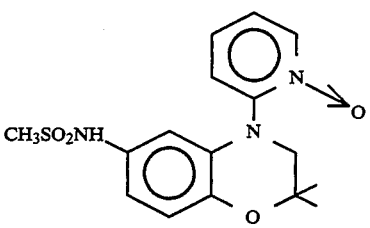

The following compound was synthesized in substantially the same manner as in Example 46.
2-(3,4-Dihydro-2,2-dimethyl-6-methanesulfonamido-2H-1,4-benzoxazin-4-yl)pyridine N-oxide.
i) Elemental analysis (for $C_6H_{19}N_3O_4 \cdot 0.5H_2O$)

|         | C (%) | H (%) | N (%) | S (%) |
|---------|-------|-------|-------|-------|
| Calcd.: | 53.62 | 5.62  | 11.72 | 8.95  |
| Found:  | 53.74 | 5.33  | 11.68 | 9.21  | ii) NMR spectrum ($CDCl_3$+DMSO-$d_6$)
δ(ppm): 1.28 (6H, s), 2.84 (3H, s), 3.51 (2H, s), 6.24–8.40 (7H, m), 9.12 (1H, broad s)
iii) Mass spectrum (m/z): 349 (M+)

EXAMPLE 48

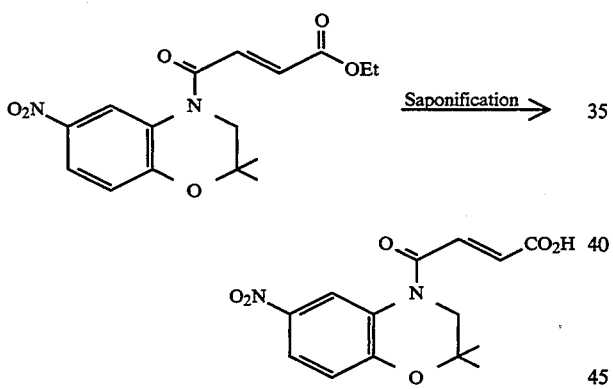

In 2 ml of ethanol was dissolved 0.5 g of ethyl trans-4-(3,4-dihydro-2,2-dimethyl-6-nitro-2H-1,4-benzoxazin-4-yl)-4-oxo-2-butenoate followed by addition of 1.5ml of an aqueous solution of 0.06 g of sodium hydroxide. The mixture was stirred at room temperature for 2 hours. The ethanol was distilled off under reduced pressure and the residue was adjusted to pH 4 with 1N hydrochloric acid. The resulting precipitate was recovered by filtration and washed with water and ethanol to give 0.31 g of trans-4-(3,4-dihydro-2,2-dimethyl-6-nitro-2H-1,4-benzoxazin-4-yl)-4-oxo-2-butenoic acid.
This compound has the following physicochemical properties.
i) Melting point: 222°–226° C.
ii) Elemental analysis (for $C_{14}H_{14}N_2O_6$)

|         | C (%) | H (%) | N (%) |
|---------|-------|-------|-------|
| Calcd.: | 54.90 | 4.61  | 9.15  |
| Found:  | 54.90 | 4.70  | 9.08  | iii) NMR spectrum (DMSO-$d_6$)
δ(ppm): 1.32 (6H, s), 3.86 (2H, s); 6.70 (1H, d), 7.08 (1H, d), 7.48 (1H, d), 7.96 (1H, dd), 8.4–8.8 (1H, broad s)

EXAMPLE 49

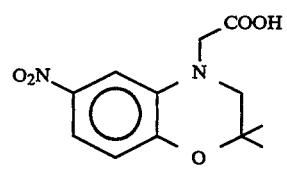

The following compound was synthesized in substantially the same manner as in Example 48.
(3,4-Dihydro-2,2-dimethyl-6-nitro-2H-1,4-benzoxazin-4-yl)acetic acid
Physicochemical properties:
i) Melting point: 162°–164° C. (decompn.) (hexane-ethyl acetate)
ii) Elemental analysis (for $C_{12}H_{14}N_2O_3$)

|         | C (%) | H (%) | N (%) |
|---------|-------|-------|-------|
| Calcd.: | 54.13 | 5.30  | 10.52 |
| Found:  | 53.95 | 5.22  | 10.58 | iii) NMR spectrum (DMSO-d6)
δ(ppm): 1.29 (6H, 3.24 (2H, s), 4.22 (2H, s), 6.83 (1H, d), 7.34 (1H, d), 7.50 (1H, dd), 12.84 (1H, broad s).
iii) Mass spectrum (m/z): 267 (M++I). (Fab(pos.)

EXAMPLE 50

To 1.00 g of ethyl (3,4-dihydro-2,2-dimethyl-6-nitro-2H-1,4-benzoxazin-4-yl)acetate was added 5 ml of methylamine (40% in methanol) and the mixture was stirred at 100° C. for 1 hour. The reaction mixture was then concentrated under reduced pressure to give crude 2-(3,4-dihydro-2,2-dimethyl-6-nitro-2H-1,4-benzoxazin-4-yl)-N-methylacetamide. This product was washed with n-hexane-ethyl acetate to obtain 950 mg of crude crystals. Recrystallization from ethyl acetate-n-hexane gave 866 mg of the desired compound.
This compound has the following physicochemical properties.
i) Melting point: 127°–128° C.
ii) Elemental analysis (for $C_{13}H_{17}N_3O$)

|         | C (%) | H (%) | N (%) |
|---------|-------|-------|-------|
| Calcd.: | 55.91 | 6.14  | 15.05 |

| | C (%) | H (%) | N (%) |
|---|---|---|---|
| Found: | 55.93 | 6.11 | 15.16 | iii) NMR spectrum (CDCl$_3$)

δ(ppm): 1.40 (6H, s), 2.86 (3H, d), 3.18 (2H, s), 3.93 (2H, s), 6.18 (1H, broad s), 6.82 (1H, d), 7.42 (1H, d), 7.66 (1H, dd)

EXAMPLE 51 TO 55

Using the ester compounds synthesized by Process 4, the following compounds were obtained in otherwise the same manner as Example 50,

| | C (%) | H (%) | N (%) |
|---|---|---|---|
| Calcd.: | 64.85 | 6.61 | 16.20 |
| Found: | 64.85 | 6.59 | 16.29 | iii) NMR spectrum (CDCl$_3$)

δ(ppm): 1.39 (6H, s), 2.87 (3H, d), 3.17 (2H, 3.85 (2H, s), 6.75–6.86 (2H, m), 7.05 (1H, dd)

EXAMPLE 52

2-(3,4-Dihydro-2,2-dimethyl-6-nitro-2H-1,4-benzoxazin-4-yl)-N-ethylacetamide.

Physicochemical properties:

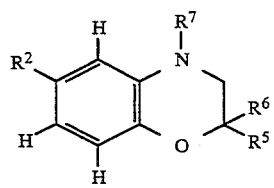

| Example No. | R$^2$ | R$^5$ | R$^6$ | R$^7$ | Starting Compound |
|---|---|---|---|---|---|
| 51 | CN | CH$_3$ | CH$_3$ | —CH$_2$CONHCH$_3$ | NC-[ring]-N(CH$_2$COOC$_2$H$_5$), H$_2$NCH$_3$ |
| 52 | NO$_2$ | CH$_3$ | CH$_3$ | —CH$_2$CONHC$_2$H$_5$ | O$_2$N-[ring]-N(CH$_2$COOC$_2$H$_5$), H$_2$NC$_2$H$_5$ |
| 53 | NO$_2$ | CH$_3$ | CH$_3$ | —CH$_2$CONHCH$_2$CH$_2$OH | O$_2$N-[ring]-N(CH$_2$COOC$_2$H$_5$), H$_2$NCH$_2$CH$_2$OH |
| 54 | NO$_2$ | CH$_3$ | CH$_3$ | —CH(CH$_3$)—CONHCH$_3$ | O$_2$N-[ring]-N(CH(CH$_3$)COOC$_2$H$_5$), H$_2$NCH$_3$ |
| 55 | NO$_2$ | CH$_3$ | CH$_3$ | —C(O)—CONHCH$_3$ | O$_2$N-[ring]-N(COCOOC$_2$H$_5$), H$_2$NCH$_3$ |

EXAMPLE 51

2-(6-Cyano-3,4-dihydro-2,2-dimethyl-2H-1,4-benzoxazin-4-yl)-N-methylacetamide.

Physicochemical properties:

i) Melting point: 150°–151° C.

ii) Elemental analysis (for C$_{14}$H$_{17}$N$_3$O$_2$)

i) Melting point: 115°–116° C.

ii) Elemental analysis (for C$_{14}$H$_{19}$N$_3$O$_4$)

| | C (%) | H (%) | N (%) |
|---|---|---|---|
| Calcd.: | 57.33 | 6.53 | 14.33 |
| Found: | 57.24 | 6.57 | 14.34 | iii) NMR spectrum (CDCl$_3$)

δ(ppm): 1.12 (3H, t), 1.40 (6H, s), 3.19 (2H, s), 3.34 (2H, m), 3.91 (2H, s), 6.17 (1H, broad s), 6.82 (1H, d), 7.44 (1H, d), 7.66 (1H, dd)

EXAMPLE 53

2-(3,4-Dihydro-2,2-dimethyl-6-nitro-2H-1,4-benzoxazin-4-yl)-N-(2-hydroxyethyl)acetamide.
Physicochemical properties:
i) Melting point: 146°-147° C.
ii) Elemental analysis (for $C_{14}H_{19}N_3O_5$)

|         | C (%) | H (%) | N (%) |
|---------|-------|-------|-------|
| Calcd.: | 54.36 | 6.19  | 13.58 |
| Found:  | 54.29 | 6.21  | 13.49 | iii) NMR spectrum (CDCl₃)
δ(ppm): 1.40 i6H, s), 1.64 (1H, broad s), 3.19 (2H, s), 3.34–3.82 (4H, m), 3.93 (2H, s), 6.72 (1H, broad s), 6.81 (1H, d), 7.43 (1H, d), 7.64 (1H, dd)

EXAMPLE 54

2-(3,4-Dihydro-2,2-dimethyl-6-nitro-2H-1,4-benzoxazin-4-yl)-N-methylpropionamide.
Physicochemical properties:
i) Melting point: 181°-182° C.
ii) Elemental analysis (for $C_{14}H_{19}N_3O_4$)

|         | C (%) | H (%) | N (%) |
|---------|-------|-------|-------|
| Calcd.: | 57.33 | 6.53  | 14.33 |
| Found:  | 57.27 | 6.54  | 14.34 | iii) NMR spectrum (CDCl₃)
δ(ppm): 1.38 (6H, s), 1.45 (3H, d), 2.86 (3H, d), 3.05 (2H, s), 4.43 (1H, q), 6.14 (1H, broad s), 6.83 (1H, dd), 7.50–7.75 (2H, m)

EXAMPLE 55

2-(3,4-Dihydro-2,2-dimethyl-6-nitro-2H-1,4-benzoxazin-4-yl)-N-methyl-2-oxoacetamide.
Physicochemical properties:
i) Melting point: 129°-130° C.
Elemental analysis (for $C_{13}H_{15}N_3O_5$)

|         | C (%) | H (%) | N (%) |
|---------|-------|-------|-------|
| Calcd.: | 53.24 | 5.16  | 14.33 |
| Found:  | 53.04 | 5.05  | 14.25 | iii) NMR spectrum (CDCl₃)
δ(ppm): 1.39 (6H, s), 2.95 (3H, d), 4.28 (1H, broad s), 6.93 (1H, d), 7.99 (1H, dd), 9.87 (1H, broad s)

EXAMPLE 56

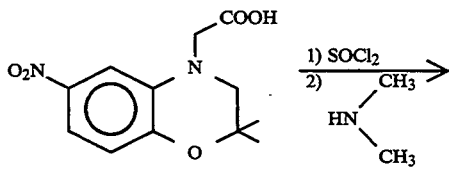

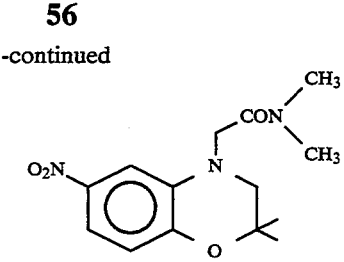

In 6 ml of chloroform were dissolved 1.0 g of (3,4-dihydro-2,2-dimethyl-6-nitro-2H-1,4-benzoxazin-4-yl)acetic acid and 1.34 g of thionyl chloride followed by addition of 2 drops of pyridine. The mixture was refluxed for 5 hours, at the end of which time it was concentrated under reduced pressure to give the acid chloride as a crude product.

The above crude acid chloride was dissolved in 5 ml of chloroform and the solution was added dropwise to a mixed solution of 0.93 g of dimethylamine hydrochloride and 1.15 g of triethylamine in 20 ml of chloroform with ice-cooling. The mixture was then stirred at room temperature for 4 hours and concentrated. The residue was subjected to silica gel chromatography using hexane-ethyl acetate (3:1–1:3) as the eluent to give 0.46 g of 2-(3,4-dihydro-2,2-dimethyl-6-nitro-2H-1,4-benzoxazin-4-yl)-N,N-dimethylacetamide, which was then recrystallized from ethyl acetate-hexane. This compound was found to have the following physicochemical properties.
i) Melting point: 179°-180° C.
ii) Elemental analysis (for $C_{14}H_{19}N_3O_4$)

|         | C (%) | H (%) | N (%) |
|---------|-------|-------|-------|
| Calcd.: | 57.33 | 6.53  | 14.33 |
| Found:  | 57.26 | 6.48  | 14.28 | iii) NMR spectrum (CDCl₃)
δ(ppm): 1.38 (6H, s), 2.99 (3H, s), 3.12 (3H, s), 3.23 (2H, s), 4.18 (2H, s), 6.79 (1H, d), 7.31 (1H, d), 7.60 (1H, dd)
iv) Mass spectrum (m/z): 293 (M+)

EXAMPLE 57-58

The following compounds were synthesized in substantially the same manner as in Example 56.

EXAMPLE 57

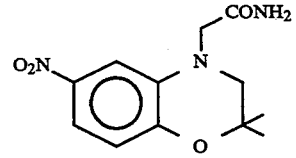

2-(3,4-Dihydro-2,2-dimethyl-6-nitro-2H-1,4-benzoxazin-4-yl)acetamide.
Physicochemical properties:
i) Melting point: 183°-184° C.
ii) Elemental analysis (for $C_{12}H_{15}N_3O_4$)

|         | C (%) | H (%) | N (%) |
|---------|-------|-------|-------|
| Calcd.: | 54.33 | 5.70  | 15.84 |
| Found:  | 54.34 | 5.68  | 15.84 | iii) NMR spectrum (CDCl₃)

δ(ppm): 1.40 (6H, s), 3.20 (2H, s), 3.93 (2H, s), 6.07 (2H, broad d), 6.81 (1H, d), 7.44 (1H, d), 7.64 (1H, dd)

EXAMPLE 58

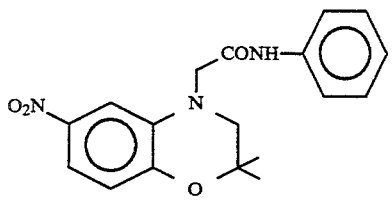

2-(3,4-Dihydro-2,2-dimethyl-6-nitro-2H-1,4-benzoxazin-4-yl)-N-phenylacetamide
Physicochemical properties:
i) Melting point: 185°–187° C.
Elemental analysis (for C₁₈H₁₉N₃O₄)

|  | C (%) | H (%) | N (%) |
|---|---|---|---|
| Calcd.: | 63.33 | 5.61 | 12.31 |
| Found: | 63.15 | 5.70 | 12.15 | iii) NMR spectrum (CDCl₃)

δ(ppm): 1.46 (6H, s), 3.24 (2H, s), 4.03 (2H, s), 6.81–7.80 (8H, m)., 9.10 (1H, broad s)

EXAMPLE 59

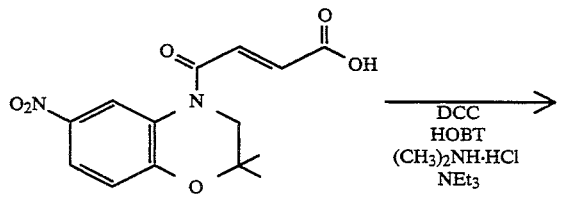

In 10 ml of tetrahydrofuran were dissolved 0.4 g of 4-(3,4-dihydro-2,2-dimethyl-6-nitro-2H-1,4-benzoxazin-4-yl)-oxo-2-butenoic acid, 0.3 g of dicyclohexylcarbodiimide and 0.26 g of 1-hydroxybenzotriazole. To this solution was added 2 ml of a mixed solution of 0.1 g of dimethylamine hydrochloride and 0.13 g of triethylamine in 2 ml of tetrahydrofuran with ice-cooling. The mixture was stirred at room temperature for 3 days, after which the precipitate was filtrated off and the solvent was distilled off under reduced pressure. The residue was dissolved in ethyl acetate and the solution was washed with aqueous potassium carbonate solution and water and dried over anhydrous magnesium sulfate. The solvent was then distilled off under reduced pressure and the residue was purified by silica gel column chromatography. The resulting crude crystals were washed with ethyl acetate-hexane to give 0.26 g of 4-(3,4-dihydro-2,2-dimethyl-6-nitro-H-1,4-benzoxazin-4-yl)-N,N-dimethyl-4-oxo-2-butenamide.

This compound has the following physicochemical properties.
i) Melting point: 179°–182° C.
ii) Elemental analysis (for C₁₆H₁₉N₃O₅)

|  | C (%) | H (%) | N (%) |
|---|---|---|---|
| Calcd.: | 57.65 | 5.75 | 12.61 |
| Found: | 57.55 | 5.96 | 12.21 | iii) NMR spectrum (CDCl₃)

δ(ppm): 1,36 (6H, s), 3.04 (3H, s), 3.20 (3H, s), 3.80 (2H, s), 6.94 (1H, d), 7.36 (1H, d), 7.60 (mH, d) 7.98 (1H, dd).

EXAMPLE 60–62

The following compounds were synthesized in substantially the same manner as in Example 59.

EXAMPLE 60

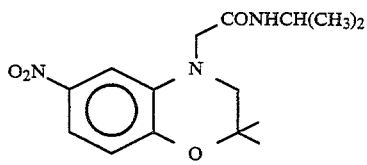

2-(3,4-Dihydro-2,2-dimethyl-6-nitro-2H-1,4-benzoxazin-4-yl)-N-isopropylacetamide.
Physicochemical properties:

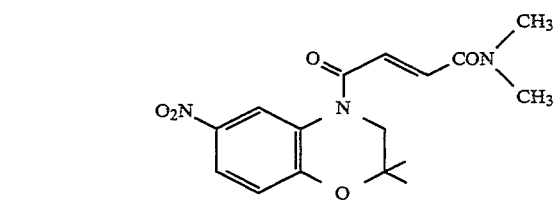

i) Melting point: 156°–156.5° C.
ii) Elemental analysis (for C₁₄H₁₇N₃O₂)

|  | C (%) | H (%) | N (%) |
|---|---|---|---|
| Calcd.: | 58.62 | 6.89 | 13.67 |
| Found: | 58.58 | 6.96 | 13.63 | iii) NMR spectrum (CDCl₃)

δ(ppm): 1.13 (6H, d), 1.40 (6H, s), 3.17 (2H, 3.86 (2H, s), 4.09 (1H, m), 6.81 (1H, 7.43 (1H, d), 7.65 (1H, dd)

iv) Mass spectrum (m/z): 293 (M⁺)

EXAMPLE 61

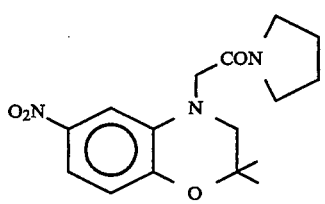

3,4-Dihydro-2,2-dimethyl-6-nitro-4-[(1-pyrrolydinyl-carbonyl)methyl]-2H-1,4-benzoxazine.
Physicochemical properties:
i) Melting point 165°–166° C.
ii) Elemental analysis (for $C_{16}H_{21}N_3O_4$)

|  | C (%) | H (%) | N (%) |
|---|---|---|---|
| Calcd.: | 60.18 | 6.63 | 13.16 |
| Found: | 60.17 | 6.68 | 13.10 | iii) NMR spectrum (CDCl$_3$)
δ(ppm): 1.38 (6H, s), 1.70–2.24 (4H, 3.27 (2H, s), 3.34–3.66 (4H, m), 4.08 (2H, s), 6.79 (1H, d), 7.33 (1H, d), 7.59 (1H, dd)

EXAMPLE 62

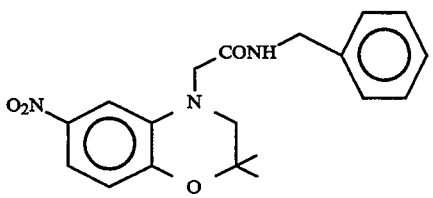

N-Benzyl-2-(3,4-dihydro-2,2-dimethyl-6-nitro-2H-1,4-benzoxazin-4-yl)acetamide.
Physicochemical properties:
i) Melting point: 133°–135° C.
ii) Elemental analysis (for $C_{19}H_{21}N_3O_4$)

|  | C (%) | H (%) | N (%) |
|---|---|---|---|
| Calcd.: | 64.21 | 5.96 | 11.82 |
| Found: | 64.17 | 6.08 | 11.88 | iii) NMR spectrum (CDCl$_3$)
δ(ppm): 1.35 (6H,s), 3.19 (2H, s), 3.98 (2H, s), 4.50 (2H, d), 6.55 (1H, broad t), 6.81 (1H, d), 7.26 (5H, s), 7.48 (1H, d), 7.66 (1H, dd)

EXAMPLE 63

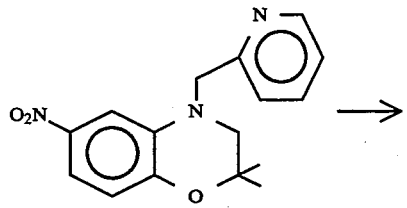

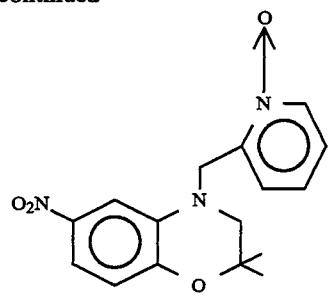

In 4 ml of methylene chloride was dissolved 0.33 g of 3,4-dihydro-2,2-dimethyl-6-nitro-4-(2-pyridylmethyl)-2H-1,4-benzoxazine followed by addition of 0.26 g of m-chloroperbenzoic acid, and the mixture was stirred at room temperature overnight. This reaction mixture was diluted with aqueous sodium hydrogen carbonate solution and extracted with methylene chloride. The organic layer was dried over anhydrous magnesium sulfate and filtered. The filtrate was concentrated under reduced pressure to give crude crystals of 2-(3,4-dihydro-2,2-dimethyl-6-nitro-2H-1,4-benzoxazin-4-yl)methylpyridine N-oxide. Recrystallization from ethanol-chloroform gave 0.2 g of the object compound. This compound was found to have the following physicochemical properties.
i) Melting point: 139°–140° C.
ii) Elemental analysis (for $C_{16}H_{17}N_3O_4$)

|  | C (%) | H (%) | N (%) |
|---|---|---|---|
| Calcd.: | 60.94 | 5.43 | 13.33 |
| Found: | 60.69 | 5.47 | 13.18 | iii) NMR spectrum (CDCl$_3$)
δ(ppm): 1.41 (6H, s), 3.27 (2H, s), 4.78 (2H, s), 6.83 (1H, d), 7.12–7.34 (4H, m), 7.61 (1H, dd), 8.24–8.42 (mH, m)

EXAMPLE 64

The following compound was synthesized in substantially the same manner as in Example 63.

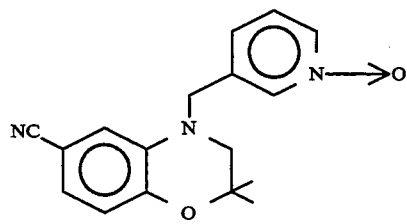

3-(6-Cyano-3,4-dihydro-2,2-dimethyl-2H-1,4-benzoxazin-4-yl)methylpyridine N-oxide.
Physicochemical properties:
i) Melting point: 144°–147° C.
ii) Elemental analysis (for $C_{17}H_{17}N_3O_2$)

|  | C (%) | H (%) | N (%) |
|---|---|---|---|
| Calcd.: | 69.14 | 5.80 | 14.23 |
| Found: | 69.33 | 5.82 | 14.23 | iii) NMR spectrum (CDCl$_3$)

δ(ppm): 1.37 (6H, s), 3.11 (2H, s), 4.42 (2H, s), 6.70–7.36 (5H, m), 8.08–8.18 (2H, m)

EXAMPLE 65

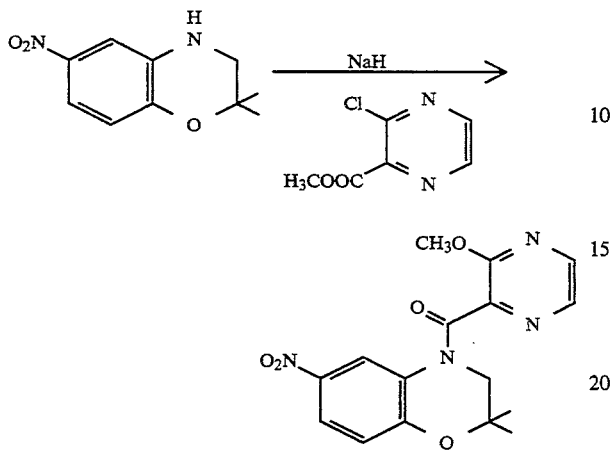

In 40 ml of N,N-dimethylformamide was dissolved 3.33 g of 3,4-dihydro-2,2-dimethyl-6-nitro-2H-1,4-benzoxazine followed by addition of 0.77 g of sodium hydride. The mixture was stirred at room temperature for 30 minutes and ice-cooled. Then, 6 ml of a solution of 2.76 g of methyl 2-chloropyrazine-3-carboxylate in N,N-dimethylformamide was added dropwise at a temperature not exceeding 5° C. The reaction mixture was then stirred at room temperature for 3.5 hours, at the end of which time it was poured in ice-water and extracted with ethyl acetate. The extract was washed with water and dried over anhydrous magnesium sulfate. The solvent was then distilled off under reduced pressure and the residue was purified by silica gel column chromatography. The resulting crude crystals were recrystallized from ethanol to give 1.27 g of 3,4-dihydro-2,2-dimethyl-4-(2-methoxy-3-pyrazinyl)carbonyl-6-nitro-2H-1,4-benzoxazine. This compound was found to have the following physicochemical properties.

i) Melting point: 183°–186° C.
ii) Elemental analysis (for $C_{16}H_{16}N_4O_5$)

|  | C (%) | H (%) | N (%) |
|---|---|---|---|
| Calcd.: | 55.81 | 4.68 | 16.27 |
| Found: | 55.96 | 4.55 | 16.09 | iii) NMR spectrum (CDCl$_3$)
δ(ppm): 1.4–1.6 (9H, broad s), 3.90 (2H, s), 6.90 (1H, d), 7.8–8.0 (1H, broad s), 8.1–8.2 (2H, m)

EXAMPLE 66

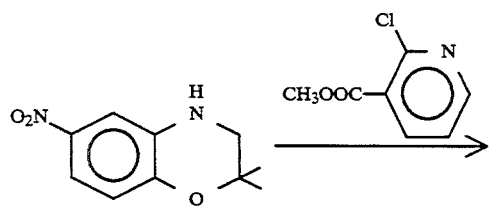

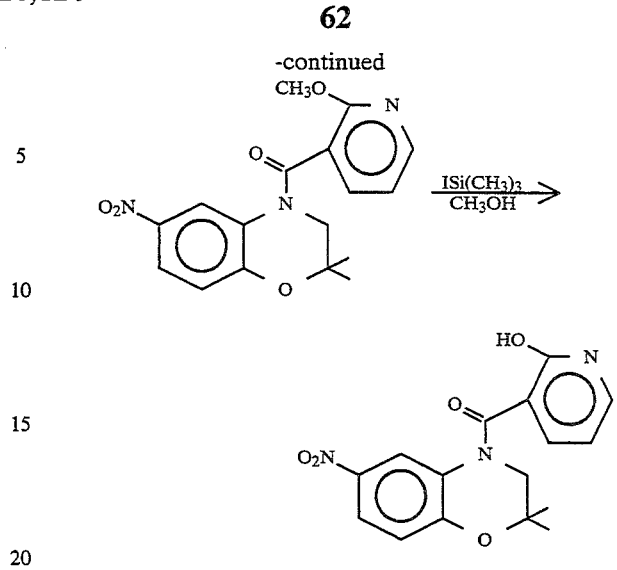

(1) The same procedure as Example 65 was followed to give 3,4-dihydro-4-[(2-methoxypyridin-3-yl)carbonyl]-2,2-dimethyl-6-nitro-2H-1,4-benzoxazine.

This compound has the following physicochemical properties.

i) Melting point: 179°–182° C.
ii) Elemental analysis (for $C_{17}H_{17}N_3O_5$)

|  | C (%) | H (%) | N (%) |
|---|---|---|---|
| Calcd.: | 59.47 | 4.99 | 12.24 |
| Found: | 59.50 | 5.08 | 12.01 | iii) NMR spectrum (CDCl$_3$)
δ(ppm): 1.45 (6H, s), 3.1–4.0 (5H, m), 6.90–7.26 (3H, m), 7.85–7.98 (2H, m), 8.29 (1H, dd)

(2) In 6 ml of carbon tetrachloride was dissolved 0.4 g of 3,4-dihydro-4-[(2-methoxypyridin-3-yl)carbonyl]-2,2-dimethyl-6-nitro-2H-1,4-benzoxazine followed by dropwise addition of 0.26 g of trimethylsilyl iodide. The mixture was heated at 50° C. for 2 hours and, then, cooled. The reaction mixture was diluted with water and extracted with chloroform. The organic layer was dried over anhydrous magnesium sulfate and filtered, the filtrate was concentrated under reduced pressure, and methanol was added to the concentrate for crystallization., Recrystallization from ethyl acetate gave 0.31 g of 3,4-dihydro-4-[(2-hydroxypyridin-3-yl)carbonyl]-2,2-dimethyl-6-nitro-2H-1,4-benzoxazine.

This compound has the following physicochemical properties.

i) Melting point: 183°–184° C.
ii) Elemental analysis (for $C_{16}H_{15}N_3O_5 \cdot 0.8CH_3COOC_2H_5$)

|  | C (%) | H (%) | N (%) |
|---|---|---|---|
| Calcd.: | 57.68 | 5.40 | 10.51 |
| Found: | 57.66 | 5.40 | 10.56 | iii) NMR spectrum (CDCl$_3$)
δ(ppm): 1.41 (6H, s), 3.70 (2H, broad s), 6.34 (1H, m), 6.94 (1H, d), 7.40–7.96 (3H, m), 8.61 (1H, m)

EXAMPLE 67

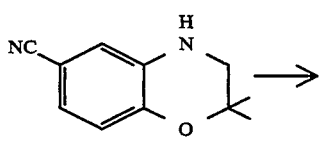

↓

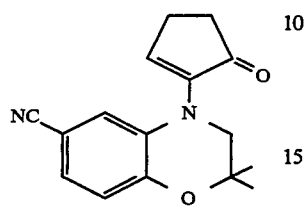

To 2.53 g of cyclopentanone were added 20 ml of carbon tetrachloride, 5.34 g of N-bromosuccinimide and a catalytic amount of dibenzoyl peroxide and the mixture was refluxed under heating for 3 hours. After cooling, the reaction mixture was filtered and the filtrate was concentrated under reduced pressure. The concentrate and 2.43 g of triethylamine were added to a solution of 0.38 g of 6-Cyano-3,4-dihydro-2,2-dimethyl-2H-1,4-benzoxazine in 5 ml of tetrahydrofuran and the mixture was stirred at room temperature overnight. The reaction mixture was then concentrated under reduced pressure, diluted with water and extracted with ethyl acetate. The organic layer was separated, dried over anhydrous magnesium sulfate and concentrated under reduced pressure. The residue was chromatographed on a silica gel column (eluent: hexane-ethyl acetate=10:1 –4:1) to give 0.3 g of crude 6-cyano-3,4-dihydro-2,2-dimethyl-4-(5-oxo-1-cyclopenten-1-yl)-2H-1,4-benzoxazine. Recrystallization from ethanol-hexane gave 0.16 g of pure product. This compound has the following physicochemical properties.
i) Melting point: 124°-126° C.
ii) Elemental analysis (for $C_{16}H_{16}N_2O_2$)

|         | C (%) | H (%) | N (%) |
|---------|-------|-------|-------|
| Calcd.: | 71.62 | 6.01  | 10.44 |
| Found:  | 71.52 | 5.99  | 10.30 | iii) NMR spectrum (CDCl3)
δ(ppm): 1.33 (6H, s), 2.50-2.77 (4H, m), 3.42 (2H, s), 6.84 (1H, d), 7.01-7.14 (2H, m), 7.21 (1H, t)

EXAMPLE 68-72

The following compounds were synthesized generally in the same manner as Example 67.

EXAMPLE 68

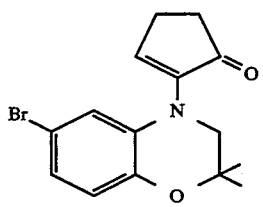

6-Bromo-3,4-dihydro-2,2-dimethyl-4-(5-oxo-1-cyclopenten-1-yl)-2H-1,4-benzoxazine.

Physicochemical properties:
i) Melting point: 110°-115° C.
ii) Elemental analysis (for $C_{15}H_{16}BrNO_2$)

|         | C (%) | H (%) | Br (%) | N (%) |
|---------|-------|-------|--------|-------|
| Calcd.: | 55.92 | 5.01  | 24.80  | 4.35  |
| Found:  | 55.61 | 5.06  | 24.49  | 4.28  | iii) NMR spectrum (CDCl3)
δ(ppm): 1.26 (6H, s), 2.4-2.8 (4H, m), 3.36 (2H, S), 6.59 (1H, d), 6.74 (1H, d), 6.87 (1H, dd), 7.11 (mH, t)

EXAMPLE 69

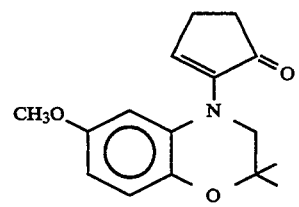

3,4-Dihydro-6-methoxy-2,2-dimethyl-4-(5-oxo-1-cyclopenten-1-yl)-2H-1,4-benzoxazine.
Physicochemical properties:
i) Melting point: 95°-97° C.
ii) Elemental analysis (for $C_{16}H_{19}NO_3$)

|         | C (%) | H (%) | N (%) |
|---------|-------|-------|-------|
| Calcd.: | 70.31 | 7.01  | 5.12  |
| Found:  | 70.17 | 6.90  | 4.92  | iii) NMR spectrum (CDCl3)
δ(ppm): 1.28 (6H, s), 2.44-2.70 (4H, m), 3.43 (2H, s), 3.69 (3H, s), 6.36 (1H, dd), 6.47 (1H, d), 6.72 (1H, d), 7.17 (1H, t)

EXAMPLE 70

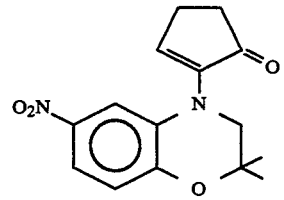

3,4-Dihydro-2,21-dimethyl-6-nitro-4-(5-oxo-1-cyclopenten-1-yl)-2H-1,4-benzoxazine.
Physicochemical properties:
i) Melting point: 96°-98° C.
ii) Elemental analysis (for $C_{15}H_{16}N_2O_4 \cdot 0.1H_2O$)

|         | C (%) | H (%) | N (%) |
|---------|-------|-------|-------|
| Calcd.: | 62.10 | 5.63  | 9.66  |
| Found:  | 62.11 | 5.64  | 9.43  | iii) NMR spectrum (CDCl3)
δ(ppm): 2.33 (6H, s), 2.51-2.59 (2H, m), 2.64-2.75 (2H, m), 3.44 (2H, s), 6.83 (1H, dd), 7.24 (1H, t), 7.61-7.22 (2H, m)

EXAMPLE 71

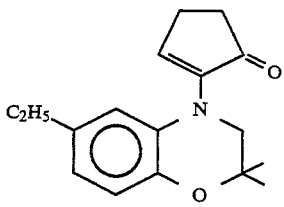

6-Ethyl-3,4-dihydro-2,2-dimethyl-4-(5-oxo-1-cyclopenten-1-yl)-2H-1,4-benzoxazine.
Physicochemical properties:
i) Melting point: 68°-70° C.
ii) Elemental analysis (for $C_{17}H_{21}NO_2$)

|  | C (%) | H (%) | N (%) |
|---|---|---|---|
| Calcd.: | 75.25 | 7.80 | 5.16 |
| Found: | 75.30 | 7.95 | 5.17 | iii) NMR spectrum (CDCl$_3$)
δ(ppm): 1.11 (3H, t), 1.27 (6H, s), 2.54–2.72 (6H, m), 3.44 (2H, s), 6.55–6.82 (3H, m), 7.06–7.17 (1H, t)

EXAMPLE 72

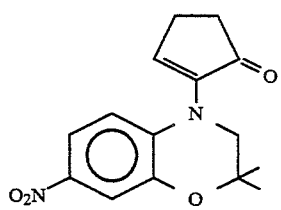

3,4-Dihydro-2,2-dimethyl-7-nitro-4-(5-oxo-1-cyclopenten-1-yl)-2H-1,4-benzoxazine.
Physicochemical properties:
i) Melting point: 88°-89° C.
ii) Elemental analysis (for $C_{15}H_{16}N_2O_4$)

|  | C (%) | H (%) | N (%) |
|---|---|---|---|
| Calcd.: | 62.49 | 5.59 | 9.72 |
| Found: | 62.21 | 5.61 | 9.60 | iii) NMR spectrum (CDCl$_3$)
δ(ppm): 1.35 (6H, s), 2.50–2.64 (2H, m), 2.68–2.79 (2H, m), 3.41 (2H, 6.68 (1H, s), 7.35 (1H, t), 7.60–7.74 (2H, m)

EXAMPLE 73

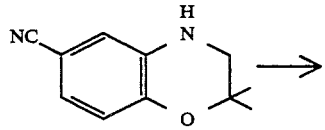

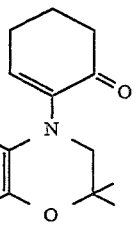

In 15 ml of toluene were dissolved 0.5 g of 6-cyano-3,4-dihydro-2,2-dimethyl-2H-1,4-benzoxazine, 0.33 g of cyclohexane-1,2-dione and a catalytic amount of p-toluenesulfonic acid and using a Dean-Stark trap, the solution was refluxed under heating for 4 hours. After cooling, the reaction mixture was washed with saturated aqueous sodium hydrogen carbonate solution and aqueous sodium chloride solution and dried over anhydrous magnesium sulfate and the solvent was distilled off under reduced pressure. The residue was purified by silica gel column chromatography and the resulting crude crystals were washed with ethanol to give 0.5 g of 6-cyano-3,4-dihydro-2,2-dimethyl-4-(6-oxo-1-cyclohexen-1-yl)-2H-1,4-benzoxazine.
This compound has the following physicochemical properties.
i) Melting point: 166°-170° C.
ii) Elemental analysis (for $C_{17}H_{18}N_2O_2$)

|  | C (%) | H (%) | N (%) |
|---|---|---|---|
| Calcd.: | 72.32 | 6.43 | 9.92 |
| Found: | 72.36 | 6.38 | 9.83 | iii) NMR spectrum (CDCl$_3$)
δ(ppm): 1.34 (6H, s), 2.0–2.2 (2H, m), 2.5–2.7 (4H, m), 2.20 (2H, s), 6.60 (1H, d), 6.76 (1H, d), 6.8–7.0 (2H, m)

EXAMPLE 74–76

The following compounds were synthesized in substantially the same manner as in Example 73.

EXAMPLE 74

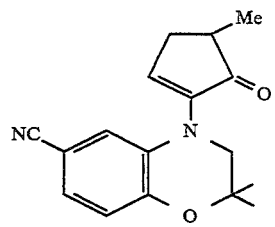

6-Cyano-3,4-dihydro-2,2-dimethyl-4-(4-methyl-5-oxo-1-cyclopenten-1-yl)-2H-1,4-benzoxazine.
Physicochemical properties:
i) Melting point: 106°-108° C.
ii) Elemental analysis (for $C_{17}H_{18}N_2O_2$)

|  | C (%) | H (%) | N (%) |
|---|---|---|---|
| Calcd.: | 72.32 | 6.43 | 9.92 |
| Found: | 72.49 | 6.50 | 9.88 | iii) NMR spectrum (CDCl$_3$)

δ(ppm): 1.26 (3H, d), 1.34 (6H, s), 2.1–3.1 (3H, m), 3.43 (2H, s), 6.8.4 (1H, d), 7.0–7.2 (3H, m)

EXAMPLE 75

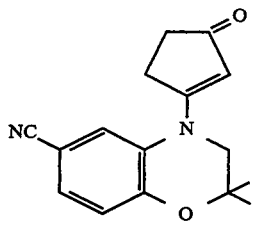

6-Cyano-3,4-dihydro-2,2-dimethyl-4-(3-oxo-1-cyclopenten-1-yl)-2H-1,4-benzoxazine.

Physicochemical properties:
i) Melting point: 180°–184° C.
ii) Elemental analysis (for $C_{16}H_{16}N_2O_2 \cdot 0.1H_2O$)

|  | C (%) | H (%) | N (%) |
|---|---|---|---|
| Calcd.: | 71.15 | 6.05 | 10.37 |
| Found: | 71.23 | 6.10 | 10.10 |

111) NMR spectrum (CDCl$_3$)
δ(ppm): 1.39 (6H, s), 2.4–2.6 (2H, m), 2.7–2.9 (2H, m), 3.55 (2H, s), 5.73 (1H, s), 6.96 (1H, d), 7.34 (1H, dd), 7.68 (1H, d)

EXAMPLE 76

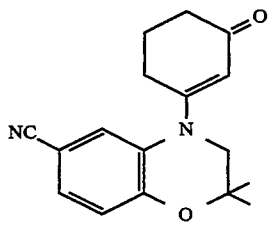

6-Cyano-3,4-dihydro-2,2-dimethyl-4-(3-oxo-1-cyclohexen-1-yl)-2H-1,4-benzoxazine.

Physicochemical properties:
i) Melting point: 147°–150° C.
ii) Elemental analysis (for $C_{17}H_{18}N_2O_2$)

|  | C (%) | H (%) | N (%) |
|---|---|---|---|
| Calcd.: | 72.32 | 6.43 | 9.92 |
| Found: | 72.40 | 6.48 | 9.91 | iii) NMR spectrum (CDCl$_3$)
δ(ppm): 1.35 (6H, s), 2.12 (2H, m), 2.44 (2H, t), 2.64 (2H, t), 3.48 (2H, s), 5.75 (1H, s), 6.93 (1H, d), 7.23 (1H, d), 7.36 (1H, dd)

EXAMPLE 77

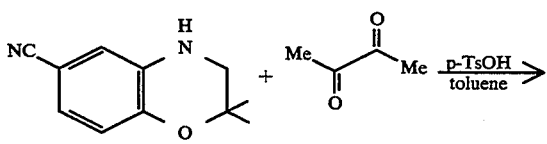

-continued

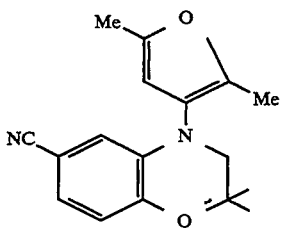

In 2 ml of toluene were dissolved 0.5 g of 6-cyano-3,4-dihydro-2,2-dimethyl-2H-1,4-benzoxazine, 1.2 ml of 2,3-butanedione and a catalytic amount of p-toluenesulfonic acid and the mixture was stirred at 100° C. for 2 days. The solvent was then distilled off under reduced pressure and the residue was re-dissolved in toluene, washed with saturated aqueous sodium hydrogen carbonate solution and saturated aqueous sodium chloride solution, and dried over anhydrous magnesium sulfate. The solvent was then distilled off and the residue was purified by silica gel column chromatography to give 0.15 g of 6-cyano-3,4-dihydro-2,2-dimethyl-4-(2,5-dimethyl-3-furyl)-2H-1,4-benzoxazine.

Physicochemical properties:
i) Melting point: 130°–132° C.
ii) Elemental analysis (for $C_7H_{18}N_2O_2$)

|  | C (%) | H (%) | N (%) |
|---|---|---|---|
| Calcd.: | 72.32 | 6.43 | 9.92 |
| Found: | 72.35 | 6.49 | 9.93 | iii) NMR spectrum (CDCl$_3$)
δ(ppm): 1.36 (6H, s), 2.12 (3H, s), 2.24 (3H, s), 3.20 (2H, s), 5.80 (1H, s), 6.70 (1H, d), 6.76 (1H, d), 6.94 (1H, dd)

EXAMPLE 78–79

The following compounds were synthesized in substantially the same manner as in Example 73.

EXAMPLE 78

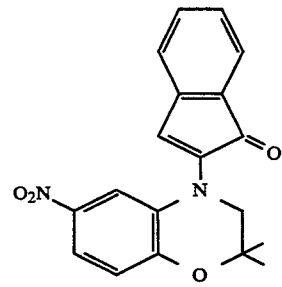

3,4-Dihydro-2,2-dimethyl-6-nitro-4-(1-oxinden-2-yl)-2H-1,4-benzoxazine.

Physicochemical properties:
i) Melting point: 161°–165° C.
ii) Elemental analysis (for $C_{19}H_{16}N_2O_4$)

|  | C (%) | H (%) | N (%) |
|---|---|---|---|
| Calcd.: | 67.85 | 4.79 | 8.33 |
| Found: | 67.89 | 4.90 | 8.22 | iii) NMR spectrum (CDCl₃)

δ(ppm): 1.37 (6H, s), 3.66 (2H, s), 6.8–7.4 (6H, m), 7.76 (1H, dd), 8.04 (1H, d)

EXAMPLE 79

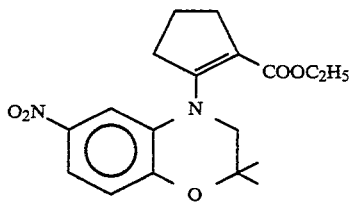

4-(2-Ethoxycarbonylcyclopenten-1-yl)-3,4-dihydro-2,2-dimethyl-6-nitro-2H-1,4-benzoxazine.

Physicochemical properties:
i) Melting point: 157°–158° C.
ii) Elemental analysis (for $C_{18}H_{22}N_2O_5 \cdot 0.5H_2O$)

|  | C (%) | H (%) | N (%) |
|---|---|---|---|
| Calcd.: | 60.83 | 6.52 | 7.88 |
| Found: | 61.03 | 6.26 | 7.71 | iii NMR spectrum (CDCl₃)

δ(ppm): 1.20 (3H, t), 1.35 (6H, s), 1.76–2.09 (2H, m), 2.64–2.84 (4H, m), 3.41 (2H, s), 4.11 (2H, q), 6.83 (1H, d), 7.59–7.77 (2H, m)

EXAMPLE 80

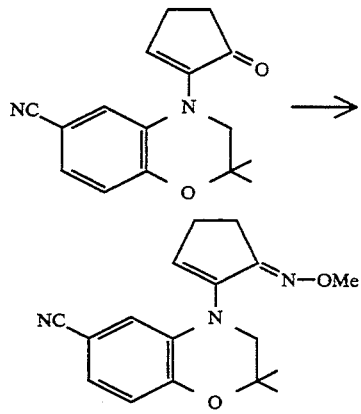

In 3 ml of pyridine was dissolved 0.3 g of 6-cyano-3,4-dihydro-2,2-dimethyl-4-(5-oxo-1-cyclopenten-1-yl)-2H-1,4-benzoxazine followed by addition of 0.26 g of methoxyamine hydrochloride. The mixture was stirred at room temperature overnight and the solvent was then distilled off under reduced pressure. The residue was poured in water and extracted with ethyl acetate. The extract was washed with water and dried over anhydrous magnesium sulfate and the solvent was distilled Off under reduced pressure. Finally the residue was washed with ethanol-ether to give 0.26 g of 6-cyano-3,4-dihydro-4-(5-methoxyimino-1-cyclopenten-1-yl)-2,2-dimethyl-2H-1,4-benzoxazine.

This compound has the following physicochemical properties.

i) Melting point: 138°–141° C.
ii) Elemental analysis (for $C_{17}H_{19}N_3O_2$)

|  | C (%) | H (%) | N (%) |
|---|---|---|---|
| Calcd.: | 68.67 | 6.44 | 14.13 |
| Found: | 68.40 | 6.60 | 13.95 | iii) NMR spectrum (CDCl₃)

δ(ppm): 1.32 (6H, s), 2.4–2.8 (4H, m), 3.38 (2H, s), 3.8.4 (3H, s), 6.26 (1H, t), 6.78 (1H, d), 6.98 (1H, dd), 7.14 (1H, d)

EXAMPLE 81

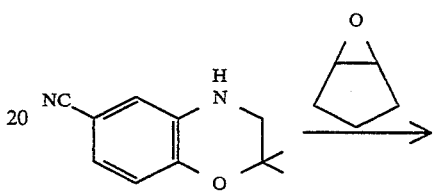

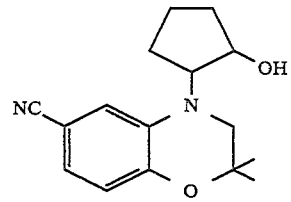

In 20 ml of N,N-dimethylformamide was dissolved 1.0 g of 6-cyano-3,4-dihydro-2,2-dimethyl-2H-1,4-benzoxazine followed by addition of 0.24 g of sodium hydride. The mixture was stirred at 70° C. for 1 hour and after cooling to room temperature, 0.5 ml of cyclopentene oxide was added. The mixture was stirred at 70° C. for 3 hours. The reaction mixture was then allowed to cool, diluted with water and extracted with ethyl acetate. The extract was washed with water and aqueous sodium chloride solution and dried over anhydrous magnesium sulfate and the solvent was distilled off under reduced pressure. The residue was purified by silica gel column chromatography and the resulting crude crystals were recrystallized from ethyl acetate-hexane to give 0.53 g of 6-cyano-3,4-dihydro-4-(2-hydroxycyclopentan-1-yl)-2,2-dimethyl-2H-1,4-benzoxazine.

Physicochemical properties:
i) Melting point: 95°–97° C.
Elemental analysis (for $C_{16}H_{20}N_2O_2$)

|  | C (%) | H (%) | N (%) |
|---|---|---|---|
| Calcd.: | 70.56 | 7.40 | 10.29 |
| Found: | 70.40 | 7.46 | 10.23 | iii) NMR spectrum (CDCl₃)

δ(ppm): 1.30 (6H, s), 1.4–2.2 (6H, m), 2.94 (2H, s), 3.8–4.3 (2H, m), 6.72 (1H, d, J=8.5 Hz), 6.92 (1H, dd, J=2.5, 8.5 Hz), 7.06 (1H, dd, J=2.5, 8.5 Hz)

EXAMPLE 82

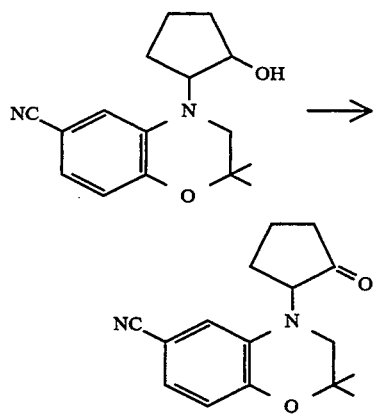

In 5 ml of methylene chloride was dissolved 0.2 ml of oxalyl chloride and at a constant temperature between −50° C. and −60° C., a solution prepared by dissolving 0.34 ml of dimethyl sulfoxide in 1 ml of methylene chloride was added dropwise. The mixture was stirred for 2 minutes, after which a solution of 0.54 g of 6-cyano-3,4-dihydro-2,2-dimethyl-4-( 2-hydroxycyclopentan-1-yl)-2H-1,4-benzoxazine in 2 ml of methylene chloride was added dropwise. The mixture was further stirred for 15 minutes and 0.7 ml of triethylamine was added. The mixture was stirred for an additional 5 minutes, after which it was allowed to return to room temperature. The reaction mixture was diluted with 10 ml of water and extracted with methylene chloride. The extract was washed with aqueous sodium chloride solution and dried over anhydrous magnesium sulfate and the solvent was distilled off under reduced pressure. The residue was recovered by filtration, washed with ethanol and recrystallized from ethyl acetate to give 0.28 g of 6-cyano-3,4-dihydro-2,2-dimethyl-4(2-oxocyclopentyl)-2H-1,4-benzoxazine.

Physicochemical properties:
i) Melting point: 172°–175° C.
ii) Elemental analysis (for $C_{16}H_{18}N_2O_2$)

|  | C (%) | H (%) | N (%) |
|---|---|---|---|
| Calcd.: | 71.09 | 6.71 | 10.36 |
| Found: | 71.01 | 6.82 | 10.29 | iii) NMR spectrum (CDCl$_3$)
δ(ppm): 1.32(3H, s), 1.36 (3H, s), 1.7–2.6 (6H, m), 2.86 (2H, dd, J=3.5, 11.5 Hz), 4.0–4.3 (1H, broad s), 6.74 (1H, d, J=8.5 Hz), 6.80 (1H, d, J=2.5 Hz), 6.94 (1H, dd, J=2.5, 8.5 Hz)

EXAMPLE 83

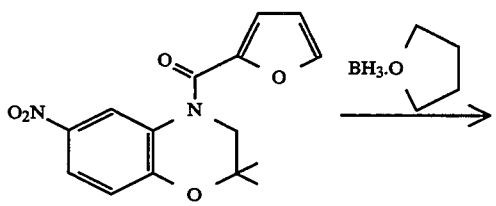

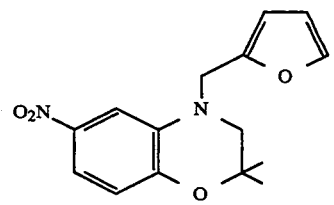

To 9 ml of a solution of borane-tetrahydrofuran complex in tetrahydrofuran (1M) was added 1.30 g of 4-(2-furoyl)-3,4-dihydro-2,2-dimethyl-6-nitro-2H-1,4-benzoxazine with ice-cooling. The mixture was then refluxed under heating with stirring for 2.5 hours. To this mixture was added 1.1 ml of methanol and after another hour of refluxing, the reaction mixture was poured in ice-water and extracted with ethyl acetate. The organic layer waswashed with water and dried over anhydrous magnesium sulfate and the solvent was distilled off. The residue was chromatographed on a silica gel column and elution was carried out with hexane-toluene (2:1). The crude crystals from the eluate were recrystallized from 3 ml of ethanol to give 546 mg of 4-furfuryl-3,41dihydro-2,2-ethyl-6-nitro-2H-1,4-benzoxazine.

This compound has the following physicochemical properties.
i) Melting point: 94°–97° C.
ii) Elemental analysis (for $C_{15}H_{16}N_2O_4$)

|  | C (%) | H (%) | N (%) |
|---|---|---|---|
| Calcd.: | 62.49 | 5.59 | 9.72 |
| Found: | 62.44 | 5.51 | 9.76 | iii) NMR spectrum (CDCl$_3$)
δ(ppm): 1.35 (6H, s), 3.13 (2H, s), 4.50 (2H, s), 6.3–6.4 (2H, m), 6.77 (1H, d), 3.36 (1H, t), 7.58 (1H, dd), 7.71 (1H, d)

EXAMPLE 84

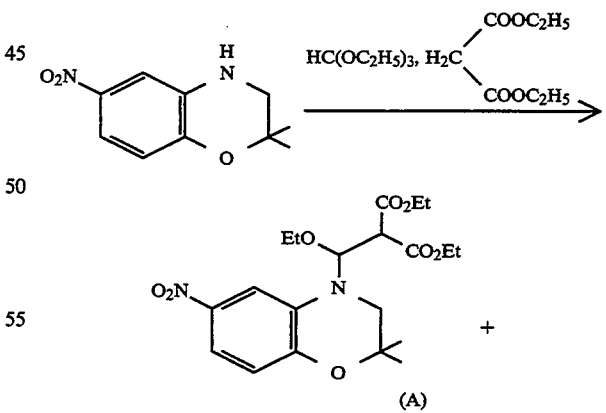

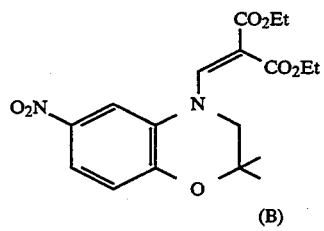

A mixture of 2.08 g of 3,4-dihydro-2,2-dimethyl-6-nitro-2H-1,4-benzoxazine, 2.96 g of ethyl orthoformate and 2.40 g of ethyl malonate was stirred in a sealed tube at 140° C. for 12 hours. After cooling, the solvent was distilled off and the residue was purified by silica gel column chromatography to give 0.33 g of diethyl 2-[1-(3,4-dihydro-2,2-dimethyl-6-nitro-2H-1,4-benzoxazin-4-yl)ethoxymethyl]malonate (compound A) and 0.31 g of diethyl 2-(3,4-dihydro-2,2-dimethyl-6-nitro-2H-1,4-benzoxazin-4-yl)methylene malonate (compound B).

Compound A
i) Melting point: 71°–74° C.
ii) Elemental analysis (for $C_{20}H_{28}N_2O_8$)

|        | C (%) | H (%) | N (%) |
|--------|-------|-------|-------|
| Calcd.:| 56.60 | 6.65  | 6.60  |
| Found: | 56.46 | 6.61  | 6.46  | iii) NMR spectrum (CDCl$_3$)
δ(ppm): 1.1–1.5 (15H, m), 3.29 (2H, s), 3.72 (2H, q), 4.28 (4H, q), 6.95 (1H, d), 7.9–8.1 (3H, m)

Compound B
i) Melting point: 89°–91° C.
ii) Elemental analysis (for $C_{20}H_{22}N_2O_7$)

|        | C (%) | H (%) | N (%) |
|--------|-------|-------|-------|
| Calcd.:| 57.14 | 5.86  | 7.40  |
| Found: | 56.93 | 5.80  | 7.27  | iii) NMR spectrum. (CDCl$_3$)
δ(ppm): 1.2–1.6 (12H, m), 3.36 (2H, s), 4.28 (4H, q), 6.95 (1H, d), 7.9–8.0 (3H, m)

EXAMPLE 85

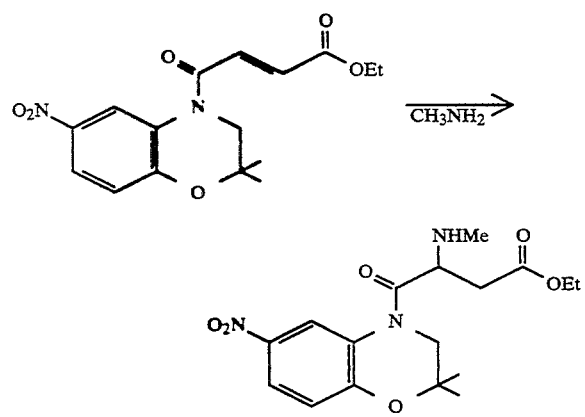

In 3 ml of methylene chloride was dissolved 0.5 g of ethyl 4-(3,4-dihydro-2,2-dimethyl-6-nitro-2H-1,4-benzoxazin-4-yl)-4-oxo-2-butenoate followed by addition of 0.116 g of methylamine in methanol. The mixture was stirred at room temperature for 4 days, at the end of which time the solvent was distilled off under reduced pressure. The residue was purified by silica gel column chromatography and the resulting crude crystals were washed with ethanol-hexane to give 0.2 g of ethyl 4-(3,4-dihydro-2,2-dimethyl-6-nitro-2H-1,4-benzoxazin-4-yl)-3-methylamino-4-oxobutanoate.

This compound has the following physicochemical properties.
i) Melting point: 75°–77° C.

ii) Elemental analysis ($C_{17}H_{23}N_3O_6$)

|        | C (%) | H (%) | N (%) |
|--------|-------|-------|-------|
| Calcd.:| 55.88 | 6.34  | 11.50 |
| Found: | 55.68 | 6.30  | 11.47 | iii) NMR spectrum (CDCl$_3$)
δ(ppm): 1.28 (3H, t), 1.36 (6H, s), 2.42 (3H, s), 3.02 (2H, d), 3.6–3.8 (3H, m), 4.20 (2H, q), 6.90 (1H, d), 7.94 (1H, dd), 8.3–8.5 (1H, broad s)

EXAMPLE 86

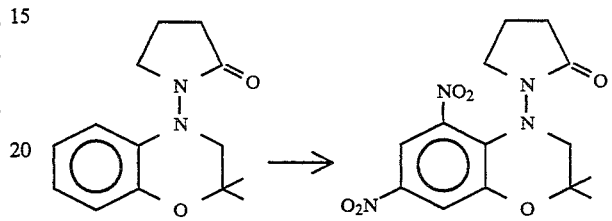

In 5.2 ml of acetonitrile was dissolved 0.35 g of 3,4-dihydro-2,2-dimethyl-4-(2-oxo-1-pyrrolidinyl)-2H-1,4-benzoxazine followed by gradual addition of 0.22 g of nitronium tetrafluoroborate. The mixture was stirred for 30 minutes and, then, poured in ice-water and extracted with ethyl acetate. The organic layer was dried and concentrated under reduced pressure and the residue was chromatographed on a silica gel column. The crude crystals obtained from the eluate were recrystallized from chloroform-ether to give 0.07 g of 3,4-dihydro-2,2-dimethyl-5,7-dinitro-4-(2-oxo-1-pyrrolidinyl)-2H-1,4-benzoxazine.

This compound has the following physicochemical properties.
i) Melting point: 189°–191° C.
ii Elemental analysis ($C_{14}H_{16}N_4O_6$)

|        | C (%) | H (%) | N (%) |
|--------|-------|-------|-------|
| Calcd.:| 50.00 | 4.80  | 16.66 |
| Found: | 49.40 | 4.76  | 16.07 | iii NMR spectrum (CDCl$_3$)
δ(ppm): 1.44 (3H, s), 1.46 (3H, s), 1.92–2.44 (4H, m), 3.18–3.61 (4H, m), 7.76 (1H, d), 7.90 (1H, d)

EXAMPLE A

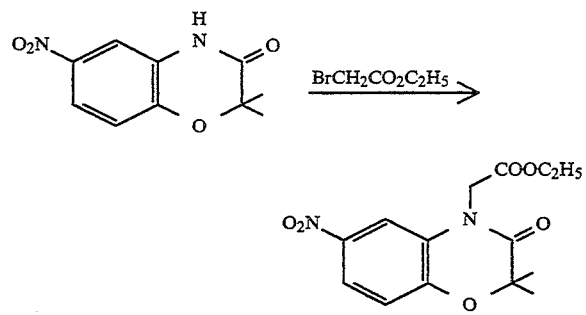

A mixture of 6.66 g of 3,4-dihydro-2,2-dimethyl-6-nitro-3-oxo-2H-1,4-benzoxazine, 5.51 g of ethyl bromoacetate, 4.5.6 g of potassium carbonate and 20 ml of acetonitrile was refluxed under heating for 2.5 hours.

Then, 10 ml of N,N-dimethylformamide was added and the mixture was stirred at 80° C. for 2 hours. To this mixture was added 2–80 g of ethyl bromoacetate. After an hour of stirring at 80° C., 2.28 g of potassium carbonate was added and the mixture was further stirred at 80° C. for 1 hour. The reaction mixture was then concentrated under reduced pressure and the residue was chromatographed on a silica gel column, elution being carried out with hexane-ethyl acetate (10:.1). The crystals from the eluate were recrystallized from ethyl acetate-hexane to give 7.4 g of ethyl (3,4-dihydro-2,2-dimethyl-6-nitro-3-oxo-2H$_{1,4}$-benzoxazin-4-yl)acetate. This compound has the following physicochemical properties.

i) Melting point: 67°–68° C.
ii) Elemental analysis (for $C_{14}H_{16}N_2O_6$)

|  | C (%) | H (%) | N (%) |
|---|---|---|---|
| Calcd.: | 54.54 | 5.23 | 9.09 |
| Found: | 54.49 | 5.24 | 9.06 | iii) NMR spectrum (CDCl$_3$)
δ(ppm): 1.32 (3H, t), 1.59 (6H, s), 4.28 (2H, q), 4.69 (2H, s), 7.08 (1H, d), 7.62 (1H, d), 7.97 (1H, dd)

EXAMPLE

The same procedure as Example A was followed to give the following compound.

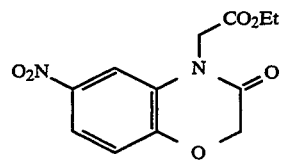

Ethyl (3,4-dihydro-6-nitro-3-oxo-2H-1,4-benzoxazin-4-yl)acetate
Physicochemical properties:
i) Melting point: 102°–103° C.
ii) Elemental analysis (for $C_{12}H_{12}N_2O_6$)

|  | C (%) | H (%) | N (%) |
|---|---|---|---|
| Calcd.: | 51.43 | 4.32 | 10.00 |
| Found: | 51.52 | 4.28 | 10.07 | iii) NMR spectrum (CDCl$_3$)
δ(ppm): 1.32 (3H, t), 4.28 (2H, q), 4.68 (2H, s), 4.78 (2H, s), 7.08 (1H, d), 7.62 (1H, d), 7.94 (1H, dd)

EXAMPLE C

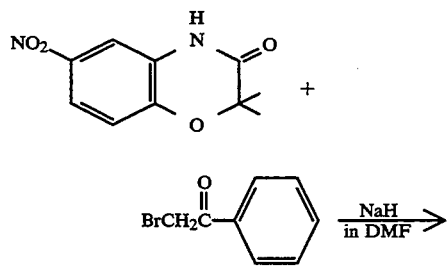

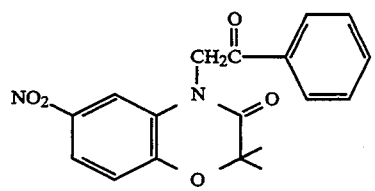

In an argon gas stream, 2.0 g of 3,4-dihydro-2,2-dimethyl-6-nitro-3-oxo-2H-1,4-benzoxazine was added gradually to 0.4 g of 60% sodium hydride in oil in 40 ml of dry N,N-dimethylformamide. The mixture was stirred at room temperature for 1 hour and 2.68 g of phenacyl bromide was added. The mixture was stirred at room temperature for 1 hour, after which the solvent was distilled off under reduced pressure. The residue was diluted with 50 ml of water and extracted with ethyl acetate. The extract was dried over anhydrous magnesium sulfate and concentrated under reduced pressure. The residue was chromatographed on a silica gel column and elution was carried out with methylene chloride-ethyl acetate. Recrystallization from ethyl acetate-ether gave 2.04 g of 3,4-dihydro-2,2-dimethyl-6-nitro-3-oxo-4-phenacyl-2H-1,4-benzoxazine.

Physicochemical properties:
i) Elemental analysis ($C_{18}H_{16}N_2O_5$)

|  | C (%) | H (%) | N (%) |
|---|---|---|---|
| Calcd.: | 63.53 | 4.74 | 8.23 |
| Found: | 63.61 | 4.72 | 8.05 | ii) Mass spectrum (EI): m/z 340 (M+)

EXAMPLE D-F

The same procedure as Example C was followed to give the following compounds.

EXAMPLE D

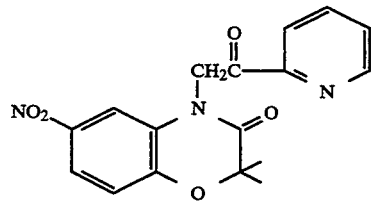

3,4-Dihydro-2,2-dimethyl-6-nitro-3-oxo-4-[(2-pyridylcarbonyl)methyl]-2H-1,4-benzoxazine
Physicochemical properties:
i) Melting point: 177°–178° C.
ii) Elemental analysis ($C_{17}H_{15}N_3O_5$)

|  | C (%) | H (%) | N (%) |
|---|---|---|---|
| Calcd.: | 59.82 | 4.43 | 12.31 |
| Found: | 59.87 | 4.45 | 12.21 | iii) Mass spectrum (EI): m/z 341 (M+)

EXAMPLE E

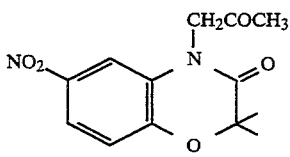

4-Acetonyl-3,4-dihydro-2,2-dimethyl-6-nitro-3-oxo-2H-1,4-benzoxazine
Physicochemical properties:
i) Melting point: 136°–137° C.
ii) Elemental analysis ($C_{13}H_{14}N_2O_5$)

|  | C (%) | H (%) | N (%) |
|---|---|---|---|
| Calcd.: | 56.11 | 5.07 | 10.07 |
| Found: | 56.11 | 5.03 | 10.04 | iii) Mass spectrum (EI): m/z 278 (M+)

EXAMPLE F

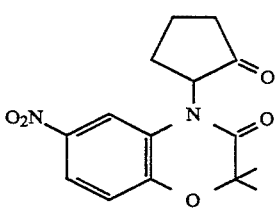

3,4-Dihydro-2,2-dimethyl-6-nitro-4-(2-oxocyclopentyl)-2H-1,4-benzoxazin-3-one
Physicochemical properties:
i) Melting point: 141°–142° C.
ii) Mass spectrum (EI): m/z 304 (M+)
iii) NMR spectrum ($CDCl_3$)
δ(ppm): 1.47 (3H, s), 1.59 (3H, s), 1.80–2.96 (6H, m], 4.26 (1H, t) 7.08 (1H, d), 7.79 (1H, d), 7.96 (1H, dd)

EXAMPLE G

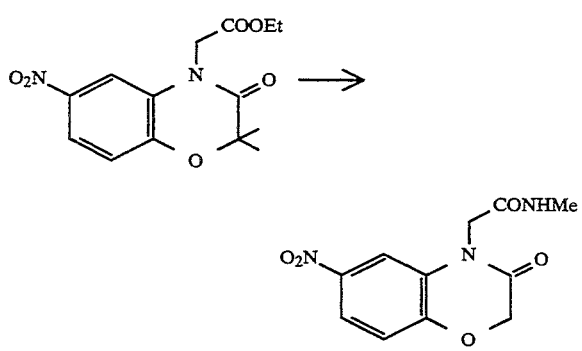

In 1.5 ml of methylene chloride were dissolved 0.5 g of ethyl (3,4-dihydro-6-nitro-3-oxo-2H-1,4-benzoxazin-4-yl)acetate and 0.16 g of 40% methylamine-methanol and the mixture was allowed to stand at room temperature for 3 days. The solvent was then distilled off and the residue was recrystallized from methylene chloride-hexane to give 0.2 g of 2-(3,4-dihydro-6-nitro-3-oxo-2H-1,4-benzoxazin-4-yl)-N-methylacetamide. This compound has the following physicochemical properties.
i) Melting point: 180°–185° C.
ii) Elemental analysis ($C_{11}H_{11}N_3O_5.0.1H_2O$)

|  | C (%) | H (%) | N (%) |
|---|---|---|---|
| Calcd.: | 49.48 | 4.23 | 15.74 |
| Found: | 49.32 | 4.25 | 15.73 | iii) NMR spectrum ($CDCl_3$)
δ(ppm): 2.82 (3H, d), 4;56 (2H, s), 4.78 (2H, s), 5.9–6.1 (1H, broad s), 7.06 (1H, d), 7.94 (1H, dd), 7.98 (1H, d)

EXAMPLE H

The same procedure as Example G was followed to give the following compound.

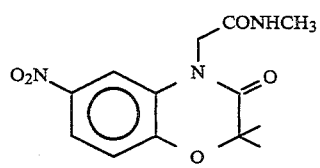

2-(3,4-Dihydro-2,2-dimethyl-6-nitro-3-oxo-2H-1,4-benzoxazin-4-yl)-N-methylacetamide
Physicochemical properties:
i) Melting point: 212°–214° C.
ii) Elemental analysis ($C_{13}H_{15}N_3O_5$)

|  | C (%) | H (%) | N (%) |
|---|---|---|---|
| Calcd.: | 53.24 | 5.16 | 14.33 |
| Found: | 53.06 | 5.10 | 14.35 | iii) NMR spectrum ($CDCl_3$)
δ(ppm): 1.56 (6H, s), 2.86 (3H, d), 4.54 (2H, 5.86 (1H, broad s), 7.06 (1H, d), 7.86–7.98 (2H, m)

The following compounds were also synthesized in a manner similar to Example 41 and the preceding examples.

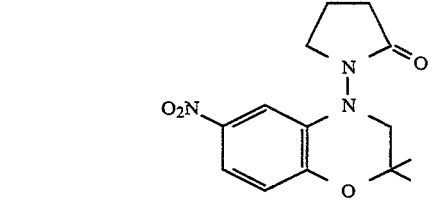

3,4-Dihydro-2,2-dimethyl-4-(2-oxo-1-piperidyl)-6-nitro-2H-1,4-benzoxazine
Physicochemical properties:
i) Melting point: 166°–168° C.
ii) Elemental analysis (for $C_{15}H_{19}N_3O_4$)

|  | C (%) | H (%) | N (%) |
|---|---|---|---|
| Calcd.: | 59.01 | 6.27 | 13.76 |
| Found: | 58.89 | 6.32 | 13.73 | iii) NMR spectrum (DMSO-$d_6$)
δ(ppm): 1.33 (3H, s), 1.40 (3H, s), 1.7–2.1 (2H, m), 2.4–2.6 (4H, m), 3.3–3.7 (4H, m), 6.92 (1H d), 7.28 (1H, Cl), 7–59 (1H, d),

EXAMPLE 88

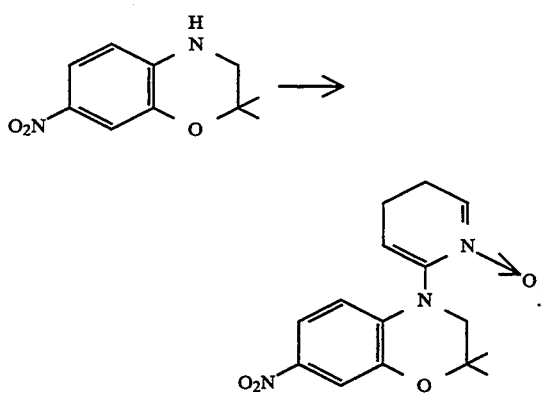

In 14 ml of N,N-dimethylformamide was suspended 0.38 g of sodium hydride (60% in oil) followed by addition of 1.00 g of 3,4-dihydro-2,2-dimethyl-7-nitro-2H-1,4-benzoxazine. Then, 1.01 g of 2-bromopyridine N-oxide hydrochloride was added with ice-cooling and the mixture was stirred at 70° C. for 16 hours. The reaction mixture was poured in ice-water and extracted with ethyl acetate. The organic layer was washed with aqueous sodium chloride solution and dried over anhydrous magnesium sulfate, and the solvent was distilled off. The residue was subjected to silica gel column chromatography and elution was carried out with chloroform-acetone (3:1) to give 0.34 g of 2-(3,4-dihydro-2,2-dimethyl-7-nitro-2H-1,4-benzoxazin-4-yl)pyridine N-oxide as oil. Then, a solution of hydrochloric acid in ethanol (prepared from 1 ml of concentrated hydrochloric acid and 5 ml of ethanol) was added thereto and the solvent was distilled off. The resulting residue wad recrystallized from acetone to give 182 mg of 2-(3,4-dihydro-2,2-dimethyl-7-nitro-2H-1,4-benzoxazin-4-yl)pyridine N-oxide hydrochloride.

This compound has the following physicochemical properties.

i) Melting point: 146°–191° C.
ii) Elemental analysis (for $C_{15}H_{15}N_3O \cdot HCl$)

|  | C (%) | H (%) | N (%) | Cl (%) |
|---|---|---|---|---|
| Calcd.: | 53.34 | 4.77 | 12.44 | 10.50 |
| Found: | 52.63 | 4.68 | 12.25 | 10.42 | iii) NMR spectrum (DMSO-$d_6$)
δ(ppm): 1.36 (6H, s), 3.70 (2H, s), 6.45 (1H, m), 7-3–7.8 (5H, m), 8.46 (1H, dd), 9.49 (1H, br s)

EXAMPLE 89

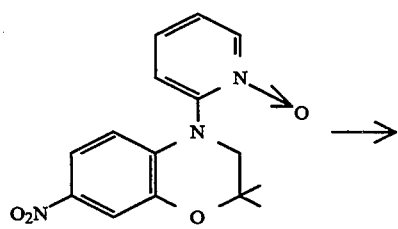

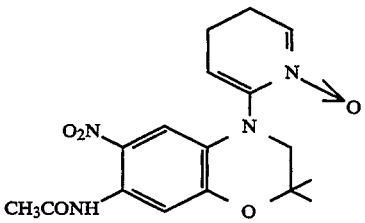

(1) To a mixture of 8.05 g of 2-(3,4-dihydro-2,2-dimethyl-7-nitro-2H-1,4-benzoxazin-4-yl)pyridine N-oxide, 28.50 g of ammonium chloride, 140 ml of methanol and 140 ml of water was added 34.94 g of zinc dust with ice-cooling, and the mixture was stirred at 5° C. for 14 hours. The insolubles were filtered off, and the filtrate was concentrated and extracted with ethyl acetate. The organic layer was dried over anhydrous magnesium sulfate and the solvent was distilled off to give 7.32 g of crude 2-(7-amino-3,4-dihydro-2,2-dimethyl-2H-1,4-benzoxazin-4-yl)pyridine N-oxide. (2) In 30 ml of methylene chloride was dissolved 6.72 g of 2-(7-amino-3,4-dihydro-2,2-dimethyl-2H-1,4-benzoxazin-4-yl)pyridine N-oxide obtained in (1) above followed by addition of 2.6 ml of acetic anhydride with ice-cooling, and the mixture was stirred at room temperature for 4 hours. To the reaction mixture was added 20 ml of methanol to decompose excess acetic anhydride, and the solvent was distilled off to give 8–40 g of crude 2-(7-acetamido-3,4-dihydro-2,2-dimethyl-2H-1,4-benzoxazin-4-yl)pyridine N-oxide. (3) In 35 ml of acetic acid was dissolved 8.76 g of 2-(7-acetamido-3,4-dihydro-2,2-dimethyl-2H-1,4-benzoxazin-4-yl)pyridine N-oxide obtained in (2) above followed by dropwise addition of a solution of nitric acid in acetic acid (prepared from 1.49 ml of fuming nitric acid and 16 ml of acetic acid) with ice-cooling, and the mixture was stirred at room temperature for 1 hour. The reaction mixture was poured into ice-water and extracted with ethyl acetate. The organic layer was washed with water and dried over anhydrous magnesium sulfate, and the solvent was distilled off. The residue was subjected to silica gel column chromatography and elution was carried out with chloroform-acetone (1:1) to obtain crystals. Recrystallization from 40 ml of ethanol gave 5.10 g of 2-(7-acetamido-3,4-dihydro-2,2-dimethyl-6-nitro-2H-1,4-benzoxazin-4-yl)pyridine N-oxide.

This compound has the following physicochemical properties.

i) Melting point: 140°–144°
ii) Elemental analysis (for $C_{17}H_{18}N_4O \cdot 0.5C_2H_5OH$)

|  | C (%) | H (%) | N (%) |
|---|---|---|---|
| Calcd.: | 56.98 | 5.06 | 15.63 |
| Found: | 56.69 | 5.51 | 14.70 | iii) NMR spectrum (CDCl$_3$)
δ(ppm): 1.42 (6H, s), 2.26 (3H, s), 3.68 (2H, s), 7.0–7.4 (3H, m), 7.48 (1H, s), 8.2–8.4 (1H, m), 8.32 (1H, s), 10.41 (1H, br s)

EXAMPLE 90

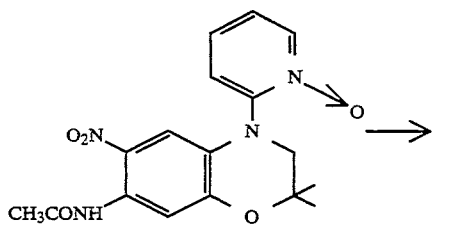

↓

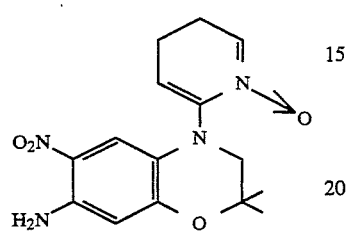

In 6 ml of ethanol was suspended 0.50 g of 2-(7-acetamido-3,4-dihydro-2,2-dimethyl-6-nitro-2H-1,4-benzoxazin-4-yl)pyridine-N-oxide followed by addition of 6 ml of 5 N hydrochloric acid, and the mixture was stirred at 100° C. for 2 hours. The reaction mixture was poured into ice-water, neutralized with excess sodium hydrogen carbonate, and extracted with chloroform. The organic layer was dried over anhydrous magnesium sulfate and the solvent was distilled off. The resulting residue was recrystallized from ethanol to give 359 mg of 2-(7-amino-3,4-dihydro-2,2-dimethyl-6-nitro-2H-1,4-benzoxazin-4-yl)pyridine N-oxide.

This compound has the following physicochemical properties.

i) Melting point: 285°–289° C. (decompn.)
ii) Elemental analysis (for $C_{15}H_{16}N_4O_4$)

|   | C (%) | H (%) | N (%) |
|---|---|---|---|
| Calcd.: | 56.96 | 5.10 | 17.71 |
| Found: | 56.80 | 5.15 | 17.50 | iii) NMR spectrum (DMSO-$d_6$)

δ(ppm): 1.35 (6H, s), 3.63 (2H, s), 6.42 (1H, s), 6.85 (1H, s), 7.1–7.3 (3H, m), 7.39 (1H, dd), 7.56 (1H, d), S.33 (1H, d)

FORMULATION EXAMPLE 1

| Compound of Example 1 | 0.1 mg |
|---|---|
| Lactose | 63 mg |
| Corn starch | 16 mg |
| Magnesium stearate | 0.9 mg |
|  | 80 mg |

The compound of Example 1, lactose and corn starch are evenly mixed and wet-granulated using corn starch as the binder. Then, magnesium stearate is added and the composition is compression-molded to give tablets.

FORMULATION EXAMPLE 2

The following ingredients are filled into ampules and, after sealing by fusion, sterilized at 115° C. for 30 minutes.

| Composition (per milliliter) | |
|---|---|
| The compound of Example 1 | 50 μg |
| Sodium chloride | 9 mg |
| Distilled water for injection | To make 1 ml |

While the invention has been described in detail and with reference to specific embodiments thereof, it will be apparent to one skilled in the art that the various changes and modifications can be made therein without departing from the spirit and scope thereof.

What is claimed is:

1. A compound of the formula (I):

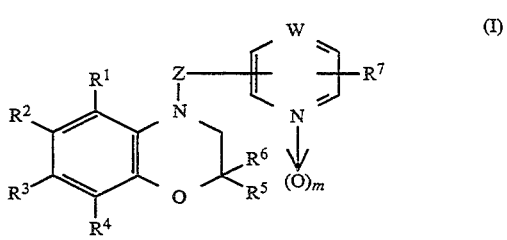

wherein m is 0 or 1;

$R^1$, $R^2$, $R^3$ and $R^4$ which may be the same or different, each independently represents a hydrogen atom, a halogen atom, a lower alkyl group, a halo-substituted lower alkyl group, a lower alkoxy group, a cyano group, a nitro group, an amino group, a lower alkanoylamino group, a lower alkylsulfonylamino group, a lower alkylsulfonyl group, or an arylsulfonyl group;

$R^5$ and $R^6$ which may be the same or different, each independently represents a hydrogen atom or a lower alkyl group;

W is —CH— or —N—;

Z is a direct bond, —C(O)—, a lower alkylene group or a hydroxy-lower alkylene group;

$R^7$ is hydrogen or one or more substituents selected from the group consisting of halogen, lower alkyl, hydroxy, lower alkoxy, oxo, carbamoyl and a mono- or di-lower-alkylamino carbonyl; with the proviso that when Z is an unsubstituted lower alkylene group, then $R^5$ and $R^6$ are not both hydrogen atoms, or a pharmaceutically acceptable salt thereof.

2. A pharmaceutical composition comprised of the compound of claim 1 or a pharmaceutically acceptable salt thereof, and a pharmaceutically acceptable carrier.

3. A method of activating potassium channels in a patient which comprises administering a therapeutically effective amount of a pharmaceutical composition as claimed in claim 2 to said patient.

4. A benzoxazine compound selected from the group consisting of 2-(3,4-dihydro-2,2-dimethyl-6-nitro-2H-1,4-benzoxazin-4-yl)pyridine N-oxide, 2-(6-cyano-3,4-dihydro-2,2-dimethyl-2H-1,4-benzoxazin-4-yl)pyridine N-oxide and 2-(3,4-dihydro-2,2-dimethyl-6-nitro-2H-1,4-benzoxazin-4-yl)-6-methylpyridine N-oxide.

5. A compound as claimed in claim 4, said compound being 2-(3,4-dihydro-2,2-dimethyl-6-nitro-2H-1,4-benzoxazin-4-yl)pyridine N-oxide.

6. A compound as claimed in claim 4, said compound being 2-(6-cyano-3,4-dihydro-2,2-dimethyl-2H-1,4-benzoxazin-4-yl)pyridine N-oxide.

7. A compound as claimed in claim 4, said compound being 2-(3,4-dihydro-2,2-dimethyl-6-nitro-2H-1,4-benzoxazin-4-yl)-6-methylpyridine N-oxide.

8. A compound of the formula (II):

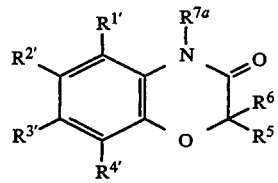

(II)

wherein $R^{1'}$, $R^{2'}$, $R^{3'}$ and $R^{4'}$, which may be the same or different, each independently represents a hydrogen atom, a halogen atom, a cyano group, or a nitro group;

$R^5$ and $R^6$, which may be the same or different, each independently represents a hydrogen atom or a lower alkyl group;

$R^{7a}$ represents a member selected from the group consisting of a 2-oxo-cyclopentyl group, a 5-oxo-1-cyclopenten-1-yl group, an acetonyl group and a phenacyl group, on a pharmaceutically acceptable salt thereof.

9. A compound of the formula (III):

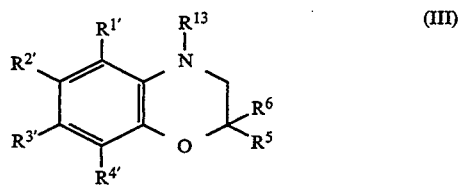

(III)

wherein $R^{1'}$, $R^{2'}$, $R^{3'}$ and $R^{4'}$, which may be the same or different, each independently represents a hydrogen atom, a halogen atom, a cyano group, or a nitro group;

$R^5$ and $R^6$, which may be the same or different, each independently represents a hydrogen atom or a lower alkyl group; and $R^{13}$ represents a nitroso group or an amino group with the proviso that when $R^{13}$ is an amino group, $R^5$ and $R^6$ are not both hydrogen atoms and a pharmaceutically acceptable salt thereof.

* * * * *